(12) United States Patent
Morris et al.

(10) Patent No.: US 9,936,701 B2
(45) Date of Patent: Apr. 10, 2018

(54) HERBICIDAL COMPOUNDS

(71) Applicants: Syngenta Participations AG, Basel (CH); Syngenta Limited, Guildford, Surrey (GB)

(72) Inventors: James Alan Morris, Bracknell (GB); Shuji Hachisu, Bracknell (GB); William Guy Whittingham, Bracknell (GB); Anne Jaqueline Dalencon, Bracknell (GB); Jutta Elisabeth Boehmer, Bracknell (GB); Mangala Phadte, Corlim Ilhas (IN); Ravindra Sonawane, Corlim Ilhas (IN); Adrian Longstaff, Bracknell (GB); Alan John Dowling, Bracknell (GB); Timothy Robert Desson, Bracknell (GB); Sitaram Pal, Corlim Ilhas (IN); Janice Black, Bracknell (GB); Swarnendu Sasmal, Corlim Ilhas (IN); Guruprasad Narashimh Sawant, Corlim Ilhas (IN); Srinivas Reddy Purumandla, Corlim Ilhas (IN); Sujit Kumar Ghorai, Corlim Ilhas (IN)

(73) Assignees: Syngenta Limited, Guildford, Surrey (GB); Syngenta Participations AG, Basel (CH)

( * ) Notice: Subject to any disclaimer, the term of this patent is extended or adjusted under 35 U.S.C. 154(b) by 0 days.

(21) Appl. No.: 14/889,948

(22) PCT Filed: May 1, 2014

(86) PCT No.: PCT/EP2014/058950
§ 371 (c)(1),
(2) Date: Nov. 9, 2015

(87) PCT Pub. No.: WO2014/180740
PCT Pub. Date: Nov. 13, 2014

(65) Prior Publication Data
US 2016/0066574 A1 Mar. 10, 2016

(30) Foreign Application Priority Data
May 8, 2013 (IN) .......................... 1378/DEL/2013

(51) Int. Cl.
| | | |
|---|---|---|
| *A01N 43/80* | (2006.01) | |
| *A01N 47/06* | (2006.01) | |
| *C07D 413/04* | (2006.01) | |
| *C07D 413/14* | (2006.01) | |

(52) U.S. Cl.
CPC ............. *A01N 43/80* (2013.01); *A01N 47/06* (2013.01); *C07D 413/04* (2013.01); *C07D 413/14* (2013.01)

(58) Field of Classification Search
None
See application file for complete search history.

(56) References Cited

FOREIGN PATENT DOCUMENTS

| | | |
|---|---|---|
| EP | 0297378 A2 | 6/1988 |
| EP | 0339390 A1 | 4/1989 |

OTHER PUBLICATIONS

Internation Search Report of International Application PCT/EP2014/058950 dated Jul. 28, 2014.

*Primary Examiner* — Hasan Ahmed
*Assistant Examiner* — Frank Choi
(74) *Attorney, Agent, or Firm* — James Cueva

(57) ABSTRACT

The invention relates to pyrrolone compounds of the formula (I) wherein X, $R^b$, $R^c$, $R^1$, $R^2$ and $R^3$ are as defined in the specification. Furthermore, the present invention relates to processes and intermediates for making compounds of formula (I), to herbicidal compositions comprising these compounds and to methods of using these compounds to control plant growth.

20 Claims, No Drawings

HERBICIDAL COMPOUNDS

RELATED APPLICATION INFORMATION

This application is a 371 of International Application No. PCT/EP2014/058950, filed May 1, 2014, which claims priority to India Application No. 1378/DEL/2013, filed May 8, 2013, the contents of which are incorporated herein by reference herein.

The present invention relates to certain substituted pyrrolone derivatives, to processes for their preparation, herbicidal compositions comprising them, and their use in controlling plants or inhibiting plant growth.

Herbicidal pyrrolones of the formula

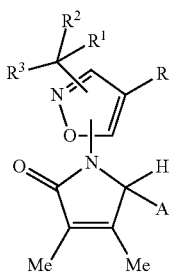

wherein A is e.g. OH, R is H, halogen, alkyl, haloalkyl, or alkoxyl, $R^1$ to $R^3$ are each H, halogen, alkyl, haloalkyl, alkyoxyalkyl, or $R^2$ and $R^3$ together form a 3 to 7 membered ring; are disclosed in EP0297378A2.

A problem that remains is the provision of alternative herbicidal pyrrolones.

A further problem that remains is the provision of herbicidal compounds having improved potency relative to known compounds.

A further problem that remains is the provision of herbicidal compounds having an improved spectrum of activity relative to known compounds.

A further problem that remains is the provision of herbicidal compounds having enhanced selectivity relative to known compounds.

These and other problems of the art are addressed by the present invention.

SUMMARY OF THE INVENTION

In a first aspect, the invention provides compounds of the formula (I)

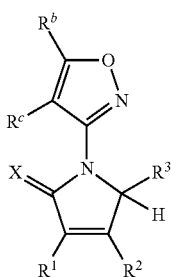

(I)

wherein
X is selected from S and O;
$R^b$ is selected from hydrogen, formyl, hydroxyl, halogen, nitro, cyano, $C_1$-$C_8$ alkyl, $C_1$-$C_6$ cyanoalkyl, $C_1$-$C_6$ haloalkyl, $C_1$-$C_6$ hydroxyalkyl, $C_2$-$C_6$ alkenyloxy $C_1$-$C_6$ alkyl, $C_1$-$C_6$ alkylthio, $C_1$-$C_6$ alkoxy, $C_1$-$C_6$ alkoxy $C_1$-$C_6$ alkyl, $C_1$-$C_6$ alkthio $C_1$-$C_6$ alkyl, $C_1$-$C_6$ cyanoalkoxy, $C_1$-$C_6$ haloalkoxy, $C_1$-$C_6$ alkoxy $C_1$-$C_6$ alkoxy, $C_2$-$C_8$ alkenyl, $C_2$-$C_8$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, tri $C_1$-$C_6$ alkylsilyl $C_2$-$C_6$ alkynyl, $C_1$-$C_6$ alkylamido, a group $R^5R^6N$—, a group $R^5C(O)N(R^6)$—, a group $R^5S(C_2)N(R^6)$—, a group $R^5R^6NSO_2$—, a group $R^5R^6NC(O)$ $C_1$-$C_6$ alkyl, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryl $C_1$-$C_3$ alkyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heterocyclyl group optionally substituted by from 1 to 3 groups independently selected from $C_1$-$C_4$ alkyl, a $C_3$-$C_6$ cycloalkyl group optionally substituted with from 1 to 3 groups independently selected from halogen, cyano, $C_1$-$C_6$ alkoxy and $C_1$-$C_6$ alkyl and a $C_3$-$C_6$ cycloalkenyl group optionally substituted with from 1 to 3 groups independently selected from halogen, cyano, $C_1$-$C_6$ alkoxy and $C_1$-$C_6$ alkyl;

$R^c$ is selected from hydrogen, halogen, cyano, $C_1$-$C_6$ alkyl and $C_1$-$C_6$ haloalkyl;

or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

$R^1$ is halogen and $R^2$ is $C_1$-$C_3$ alkyl, $C_1$-$C_3$ alkoxy or —$NR^{10}R^{11}$ or $R^1$ is $C_1$-$C_3$ alkoxy and $R^2$ is halogen, $C_1$-$C_3$ alkyl, $C_1$-$C_3$ alkoxy, or $R^1$ is $C_1$-$C_3$ alkyl and $R^2$ is $C_1$-$C_3$ alkoxy;

$R^3$ is selected from halogen, hydroxyl, or any one of the following groups

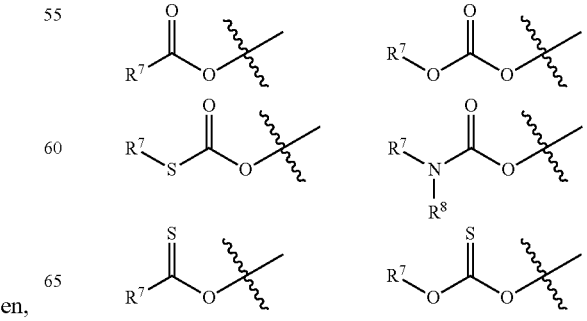

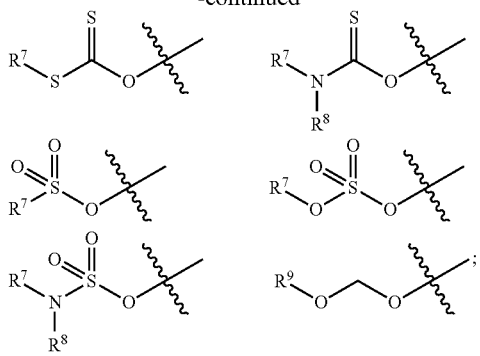

R$^5$ and R$^6$ are independently selected from hydrogen, C$_1$-C$_6$ alkyl, C$_1$-C$_6$ haloalkyl, C$_2$-C$_6$ alkenyl, C$_2$-C$_6$ alkynyl, or R$^5$ and R$^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and C$_1$-C$_6$ alkyl;

R$^7$ and R$^8$ are independently selected from hydrogen, C$_1$-C$_6$ alkyl, C$_1$-C$_6$ haloalkyl, C$_2$-C$_6$ alkenyl, C$_2$-C$_6$ alkynyl, a C$_5$-C$_{10}$ heteroaryl group which can be mono- or bicyclic comprising from 1 to 4 heteroatoms independently selected from N, O and S and optionally substituted with 1 to 3 groups independently selected from halogen, C$_1$-C$_3$ alkyl, C$_1$-C$_3$ haloalkyl and C$_1$-C$_3$ alkoxy, a C$_6$-C$_{10}$ aryl group optionally substituted with 1 to 3 groups independently selected from halogen, nitro, cyano, C$_1$-C$_3$ alkyl, C$_1$-C$_3$ alkoxy, C$_1$-C$_3$ haloalkyl and C$_1$-C$_3$ haloalkoxy, or R$^7$ and R$^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen or C$_1$-C$_6$ alkyl;

R$^9$ is selected from C$_1$-C$_6$ alkyl or benzyl optionally substituted with 1 to 3 groups independently selected from halogen, nitro, cyano, C$_1$-C$_3$ alkyl, C$_1$-C$_3$ alkoxy, C$_1$-C$_3$ haloalkyl and C$_1$-C$_3$ haloalkoxy;

R$^{10}$ is selected from H, C$_1$-C$_6$ alkyl, C$_1$-C$_6$ alkoxy-C$_1$-C$_6$ alkyl, C$_3$-C$_6$ cycloalkyl, C$_3$-C$_6$ cycloalkyl-C$_1$-C$_6$ alkyl, C$_2$-C$_6$ alkenyl and C$_2$-C$_6$ alkynyl;

R$^{11}$ is selected from H and C$_1$-C$_6$ alkyl, or an N-oxide or salt form thereof.

In a second aspect, the invention provides herbicidal compositions comprising a compound of the invention together with at least one agriculturally acceptable adjuvant or diluent.

In a third aspect, the invention provides the use of a compound or a composition of the invention for use as a herbicide.

In a fourth aspect, the invention provides a method of controlling weeds in crops of useful plants, comprising applying to said weeds or to the locus of said weeds, or to said useful crop plants, a compound or a composition of the invention.

In a fifth aspect, the invention relates to processes useful in the preparation of compounds of the invention.

In a sixth aspect, the invention relates to intermediates useful in the preparation of compounds of the invention.

DETAILED DESCRIPTION

In particularly preferred embodiments of the invention, the preferred groups for X, R$^b$, R$^c$, R$^1$, R$^2$ and R$^3$, in any combination thereof, are as set out below.

Preferably, X is O.

Preferably, R$^b$ is selected from C$_1$-C$_8$ alkyl, C$_1$-C$_6$ haloalkyl, C$_2$-C$_8$ alkenyl, C$_1$-C$_6$ cyanoalkyl, C$_1$-C$_6$ alkoxy, C$_1$-C$_6$ hydroxyalkyl, C$_2$-C$_6$ alkenyloxy C$_1$-C$_6$ alkyl, a group R$^5$R$^6$NC(O) C$_1$-C$_6$ alkyl, C$_1$-C$_6$ alkoxy C$_1$-C$_6$ alkyl and C$_3$-C$_6$ cycloalkyl optionally substituted by from 1 to 3 groups independently selected from cyano, C$_1$-C$_3$ alkyl and C$_1$-C$_3$ alkoxy.

More preferably, R$^b$ is selected from C$_1$-C$_8$ alkyl, C$_1$-C$_6$ haloalkyl, C$_2$-C$_8$ alkenyl, C$_1$-C$_6$ cyanoalkyl, C$_1$-C$_6$ alkoxy C$_1$-C$_6$ alkyl and C$_3$-C$_6$ cycloalkyl optionally substituted by from 1 to 3 groups independently selected from cyano and C$_1$-C$_3$ alkyl.

Even more preferably, R$^b$ is selected from C$_1$-C$_6$ alkyl, C$_2$-C$_8$ alkenyl, C$_1$-C$_6$ cyanoalkyl, C$_1$-C$_6$ alkoxy C$_1$-C$_6$ alkyl and C$_3$-C$_6$ cycloalkyl optionally substituted by from 1 to 3 groups independently selected from cyano and C$_1$-C$_3$ alkyl.

Even more preferably R$^b$ is selected from methyl, ethyl, iso-propyl, (2-methyl)-prop-1-yl, (1-methyl)-prop-1-yl, tert-butyl, (1,1-dimethyl)-prop-1-yl, (1,1-dimethyl)-but-1-yl, (1-methyl-1-ethyl)-prop-1-yl, (1,1-dimethyl)-prop-2-en-1-yl, (1,1-dimethyl)-but-3-en-1-yl, (1,1-dimethyl-2-methoxy)-prop-1-yl, cyclobutyl, cyclopropyl, (1-methyl)cycloprop-1-yl, (1-methyl-1-cyano)-eth-1-yl, (1-methyl-1-ethyl-2-cyano)-prop-1-yl and (1,1-dimethyl-2-cyano)-prop-1-yl.

Most preferably, R$^b$ is selected from iso-propyl, tert-butyl, (1-methyl)-prop-1-yl, (1-methyl-1-ethyl)-prop-1-yl, (1,1-dimethyl)-prop-2-en-1-yl, (1,1-dimethyl)-but-3-en-1-yl, (1-methyl-1-cyano)-eth-1-yl, (1-methyl-1-ethyl-2-cyano)-prop-1-yl and (1,1-dimethyl-2-cyano)-prop-1-yl.

Preferably, R$^c$ is selected from hydrogen, halogen, cyano and C$_1$-C$_3$ alkyl. More preferably R$^c$ is selected from hydrogen, fluorine, chlorine, bromine, methyl and cyano. Most preferably, R$^c$ is selected from hydrogen, fluorine and cyano.

In a preferred embodiment, the isoxazole ring is a 5-iso-propylisoxazol-3-yl ring.

In another preferred embodiment, the isoxazole ring is a 5-tert-butylisoxazol-3-yl ring.

In another preferred embodiment, the isoxazole ring is a 5-tert-butyl-4-fluoro-isoxazol-3-yl ring.

In another preferred embodiment, the isoxazole ring is a 5-tert-butyl-4-cyano-isoxazol-3-yl ring.

In another preferred embodiment, the isoxazole ring is a 5-(1-cyano-1-methyl-ethyl)isoxazol-3-yl ring.

In another preferred embodiment, the isoxazole ring is a 5-(1,1-dimethylpropyl)isoxazol-3-yl ring.

In another preferred embodiment, the isoxazole ring is a 5-(1,1-dimethylallyl)isoxazol-3-yl ring.

In another preferred embodiment, the isoxazole ring is a 5-(1,1-dimethylbut-3-enyl)isoxazol-3-yl ring.

Preferably, R$^1$ is selected from methyl, ethyl, n-propyl, chloro, bromo, iodo, methoxy and ethoxy. More preferably, R$^1$ is selected from methyl, chloro, bromo, methoxy and ethoxy. Most preferably, R$^1$ is selected from methyl, chloro, bromo and methoxy.

Preferably, R$^2$ is selected from methyl, ethyl, n-propyl, methoxy, ethoxy, N-allylamino, N-propargylamino and amino. More preferably, R$^2$ is selected from methyl, methoxy, N-allylamino, N-propargylamino and amino. Most preferably, R$^2$ is methyl.

More preferably, $R^1$ is chloro and $R^2$ is methyl, $R^1$ is bromo and $R^2$ is methyl or $R^1$ is methoxy and $R^2$ is methyl. Most preferably, $R^1$ is methoxy and $R^2$ is methyl.

In one embodiment, $R^1$ is halogen and $R^2$ is $C_1$-$C_3$ alkyl. Preferably, $R^1$ is chloro and $R^2$ is methyl or $R^1$ is bromo and $R^2$ is methyl.

In another embodiment, $R^1$ is halogen and $R^2$ is $C_1$-$C_3$ alkoxy. Preferably, $R^1$ is chloro and $R^2$ is methoxy or $R^1$ is bromo and $R^2$ is methoxy.

In another embodiment, $R^1$ is halogen and $R^2$ is —$NR^{10}R^{11}$, $R^{10}$ and $R^{11}$ may be as defined above. Preferably, $R^{10}$ is selected from H, $C_1$-$C_6$ alkyl, $C_2$-$C_6$ alkenyl and $C_2$-$C_6$ alkynyl. More preferably, $R^{10}$ is selected from H, methyl, allyl and propargyl. Preferably, $R^{11}$ is selected from H and $C_1$-$C_6$ alkyl. More preferably, $R^{11}$ is selected from H and methyl. Preferably, $R^1$ is chloro and $R^2$ is amino, $R^1$ is chloro and $R^2$ is N-allylamino, $R^1$ is chloro and $R^2$ is N-propargylamino, $R^1$ is bromo and $R^2$ is amino, $R^1$ is bromo and $R^2$ is N-allylamino or $R^1$ is bromo and $R^2$ is N-propargylamino.

In another embodiment, $R^1$ is $C_1$-$C_3$ alkoxy and $R^2$ is $C_1$-$C_3$ alkyl. Preferably, $R^1$ is methoxy and $R^2$ is methyl.

In another embodiment, $R^1$ is $C_1$-$C_3$ alkoxy and $R^2$ is $C_1$-$C_3$ alkoxy. Preferably, $R^1$ is methoxy and $R^2$ is methoxy.

In another embodiment, $R^1$ is $C_1$-$C_3$ alkoxy and $R^2$ is halogen. Preferably, $R^1$ is methoxy and $R^2$ is chloro or $R^1$ is methoxy and $R^2$ is bromo.

In another embodiment, $R^1$ is $C_1$-$C_3$ alkyl and $R^2$ is $C_1$-$C_3$ alkoxy. Preferably, $R^1$ is methyl and $R^2$ is methoxy.

Preferably, $R^3$ is selected from halogen, hydroxyl, or any of the following groups

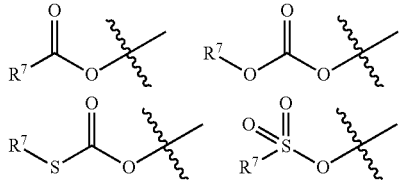

$R^7$ may be as defined above but preferably, $R^7$ is selected from $C_1$-$C_6$ alkyl, $C_1$-$C_6$ haloalkyl, $C_2$-$C_6$ alkenyl, $C_2$-$C_6$ alkynyl, a $C_5$-$C_{10}$ monocyclic heteroaryl group comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy and a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

More preferably, $R^3$ is selected from hydroxyl, halogen, $C_1$-$C_6$ alkylcarbonyloxy, $C_1$-$C_6$ alkoxycarbonyloxy and aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

Even more preferably, $R^3$ is selected from hydroxyl and halogen. Most preferably, $R^3$ is hydroxyl.

The compounds of formula (I) may exist as different geometric isomers, or in different tautomeric forms. This invention covers all such isomers and tautomers, and mixtures thereof in all proportions, as well as isotopic forms such as deuterated compounds.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and agrochemically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Alkyl, as used herein refers to an aliphatic hydrocarbon chain and includes straight and branched chains e. g. of 1 to 8 carbon atoms such as methyl, ethyl, n-propyl, isopropyl, n-butyl, isobutyl, sec-butyl, t-butyl, n-pentyl, isopentyl, neopentyl, n-hexyl, and isohexyl.

Alkenyl, as used herein, refers to an aliphatic hydrocarbon chain having at least one double bond, and preferably one double bond, and includes straight and branched chains e. g. of 2 to 8 carbon atoms such as ethenyl(vinyl), prop-1-enyl, prop-2-enyl(allyl), isopropenyl, but-1-enyl, but-2-enyl, but-3-enyl, 2-methypropenyl.

Alkynyl, as used herein, refers to an aliphatic hydrocarbon chain having at least one triple bond, and preferably one triple bond, and includes straight and branched chains e. g. of 2 to 8 carbon atoms such as ethynyl, prop-1-ynyl, prop-2-ynyl(propargyl) but-1-ynyl, but-2-ynyl and but-3-ynyl.

Cycloalkyl, as used herein, refers to a cyclic, saturated hydrocarbon group having from 3 to 6 ring carbon atoms. Examples of cycloalkyl groups are cyclopropyl, cyclobutyl, cyclopentyl and cyclohexyl.

Cycloalkenyl, as used herein, refers to a cyclic, partially unsaturated hydrocarbon group having from 3 to 6 ring carbon atoms.

Alkoxy as used herein refers to the group —OR, wherein R is alkyl as defined above. Examples of alkoxy groups include methoxy, ethoxy, n-propoxy, isopropoxy, n-butoxy, isobutoxy, sec-butoxy, t-butoxy, n-pentoxy, isopentoxy, neopentoxy, n-hexyloxy, and isohexyloxy.

Alkenyloxy refers to the group —OR, wherein R is alkenyl as defined above. Examples of alkenyloxy groups are ethenyloxy, propenyloxy, isopropenyloxy, but-1-enyloxy, but-2-enyloxy, but-3-enyloxy, 2-methypropenyloxy etc.

Alkynyloxy refers to the group —OR, wherein R is alkynyl is as defined above. Examples of alkynyloxy groups are ethynyloxy, propynyloxy, but-1-ynyloxy, but-2-ynyloxy and but-3-ynyloxy.

Alkoxyalkyl as used herein refers to the group —ROR, wherein each R is, independently, an alkyl group as defined above.

Alkoxyalkenyl as used herein refers to the group —ROR', wherein R is an alkyl group as defined above and R' is an alkenyl group as defined above.

Alkoxyalkynyl as used herein refers to the group —ROR', wherein R is an alkyl group as defined above and R' is an alkynyl group as defined above.

Alkoxyalkoxy, as used herein, refers to the group —OROR, wherein each R is, independently, an alkyl group as defined above.

Cyanoalkyl as used herein refers to an alkyl group substituted with one or more cyano groups.

Cyanoalkenyl as used herein refers to an alkenyl group substituted with one or more cyano groups.

Cyanoalkynyl as used herein refers to an alkynyl group substituted with one or more cyano groups.

Cyanocycloalkyl as used herein refers to an cycloalkyl group substituted with one or more cyano groups.

Cyanoalkoxy as used herein refers to the group —OR, wherein R is cyanoalkyl as defined above.

Halogen, halide and halo refer to iodine, bromine, chlorine and fluorine.

Haloalkyl as used herein refers to an alkyl group as defined above wherein at least one hydrogen atom has been replaced with a halogen atom as defined above. Examples of haloalkyl groups include chloromethyl, dichloromethyl, trichloromethyl, fluoromethyl, difluoromethyl and trifluoromethyl. Preferred haloalkyl groups are fluoroalkyl groups {i.e. haloalkyl groups, containing fluorine as the only halogen). More highly preferred haloalkyl groups are perfluoroalkyl groups, i.e. alkyl groups wherein all the hydrogen atoms are replaced with fluorine atoms.

Haloalkenyl as used herein refers to an alkenyl group as defined above wherein at least one hydrogen atom has been replaced with a halogen atom as defined above.

Haloalkynyl as used herein refers to an alkynyl group as defined above wherein at least one hydrogen atom has been replaced with a halogen atom as defined above.

Haloalkoxy as used herein refers to the group —OR, wherein R is haloalkyl as defined above.

Haloalkenyloxy as used herein refers to the group —OR, wherein R is haloalkenyl as defined above.

Haloalkynyloxy as used herein refers to the group —OR, wherein R is haloalkynyl as defined above.

Alkylthio as used herein refers to the group —SR, wherein R is an alkyl group as defined above. Alkylthio groups include, but are not limited to, methylthio, ethylthio, propylthio, tert-butylthio, and the like.

Alkylthioalkyl as used herein refers to the group —RSR, wherein each R is, independently, an alkyl group as defined above.

Haloalkylthio as used herein refers to the group —SR, wherein R is a haloalkyl group as defined above.

Alkylsulfinyl as used herein refers to the group —S(O)R, wherein R is an alkyl group as defined above.

Alkylsulfonyl as used herein refers to the group —S(O)$_2$R, wherein R is an alkyl group as defined above.

Haloalkylsulfinyl as used herein refers to the group —S(O)R, wherein R is a haloalkyl group as defined above.

Haloalkylsulfonyl as used herein refers to the group —S(O)$_2$R, wherein R is a haloalkyl group as defined above.

Alkylsulfonyloxy, as used herein refers to the group —OSO$_2$R, wherein R is an alkyl group as defined above.

Alkylcarbonyl, as used herein refers to the group —COR, wherein R is an alkyl group as defined above. Examples of alkylcarbonyl groups include ethanoyl, propanoyl, n-butanoyl, etc.

Alkenylcarbonyl, as used herein refers to the group —COR, wherein R is an alkenyl group as defined above.

Alkynylcarbonyl, as used herein refers to the group —COR, wherein R is an alkynyl group as defined above.

Haloalkylcarbonyl, as used herein refers to the group —COR, wherein R is a haloalkyl group as defined above.

Haloalkenylcarbonyl, as used herein refers to the group —COR, wherein R is a haloalkenyl group as defined above.

Haloalkynylcarbonyl, as used herein refers to the group —COR, wherein R is a haloalkynyl group as defined above.

Alkoxycarbonyloxy as used herein, refers to the group —OC(O)OR, wherein R is an alkyl group as defined above.

Examples of alkoxycarbonyloxy groups are methoxycarbonyloxy, ethoxycarbonyloxy, propoxycarbonyloxy, but-1-oxycarbonyloxy, but-2-oxycarbonyloxy and but-3-oxycarbonyloxy.

Trialkylsilylalkynyl, as used herein, refers to the group —RSi(R')$_3$, wherein R is an alkynyl group as defined above and each R' is, independently, selected from an alkyl group as defined above.

Formyl, as used herein, refers to the group —C(O)H.

Hydroxy or hydroxyl, as used herein, refers to the group —OH.

Nitro, as used herein, refers to the group —NO$_2$.

Cyano, as used herein, refers to the group —CN.

Aryl, as used herein, refers to an unsaturated aromatic carbocyclic group of from 6 to 10 carbon atoms having a single ring (e. g., phenyl) or multiple condensed (fused) rings, at least one of which is aromatic (e.g., indanyl, naphthyl). Preferred aryl groups include phenyl, naphthyl and the like. Most preferably, an aryl group is a phenyl group.

Aryloxy, as used herein, refers to the group —O-aryl, wherein aryl is as defined above. Preferred aryloxy groups include phenoxy, naphthyloxy and the like.

Aryloxycarbonyloxy, as used herein, refers to the group —OC(O)O-aryl wherein aryl is a as defined above.

Benzyl, as used herein, refers to the group —CH$_2$C$_6$H$_5$.

Benzyloxy, as used herein, refers to the group —OCH$_2$C$_6$H$_5$.

Heterocyclyl, as used herein, refers to a non-aromatic ring system containing 3 to 10 ring atoms, at least one ring heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyrrolidinyl, imidazolinyl, pyrazolidinyl, piperidyl, piperazinyl, quinuclidinyl, morpholinyl, together with unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

Heteroaryl, as used herein, refers to a ring system containing 5 to 10 ring atoms, 1 to 4 ring heteroatoms and consisting either of a single aromatic ring or of two or more fused rings, at least one of which is aromatic. Preferably, single rings will contain up to three and bicyclic systems up to four heteroatoms which will preferably be independently chosen from nitrogen, oxygen and sulfur. Examples of such groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. Examples of bicyclic groups are benzothiophenyl, benzimidazolyl, benzothiadiazolyl, quinolinyl, cinnolinyl, quinoxalinyl and pyrazolo[1,5-a]pyrimidinyl.

'Saturated ring', as used herein, refers to a ring system in which the atoms in the ring are linked by single bonds.

'Partially unsaturated ring', as used herein, refers to a ring system in which at least two atoms in the ring are linked by a double bond. Partially unsaturated ring systems do not include aromatic rings.

"Optionally substituted" as used herein means the group referred to can be substituted at one or more positions by any one or any combination of the radicals listed thereafter. For most groups, one or more hydrogen atoms are replaced by the radicals listed thereafter. For halogenated groups, for example, haloalkyl groups, one or more halogen atoms are replaced by the radicals listed thereafter.

Suitable salts include those derived from alkali or alkaline earth metals and those derived from ammonia and amines. Preferred cations include sodium, potassium, magnesium, and ammonium cations of the formula $N^+(R^{19}R^{20}R^{21}R^{22})$ wherein $R^{19}$, $R^{20}$, $R^{21}$ and $R^{22}$ are independently selected from hydrogen, $C_1$-$C_6$ alkyl and $C_1$-$C_6$ hydroxyalkyl. Salts of the compounds of formula (I) can be prepared by treatment of compounds of formula (I) with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of formula (I) because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

In another aspect the present invention provides intermediates useful in the preparation of compounds of the invention.

In one embodiment, there are provided intermediates of the formula (III)

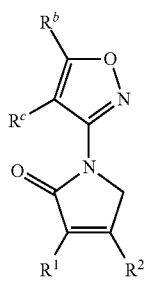

(III)

wherein $R^b$, $R^c$, $R^1$ and $R^2$ are as defined above. These intermediates can also display herbicidal activity.

In another embodiment, there are provided intermediates of the formula (IV)

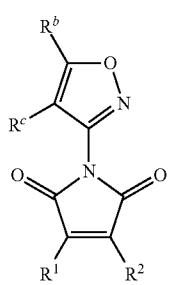

(IV)

wherein $R^b$, $R^c$, $R^1$ and $R^2$ are as defined above.

Compounds of the invention may be prepared by techniques known to the person skilled in the art of organic chemistry. General methods for the production of compounds of formula (I) are described below. Unless otherwise stated in the text, the substituents X, A, $R^1$, $R^2$, $R^3$, $R^b$ and $R^c$ are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallization, distillation and filtration.

For example, compounds of formula (I) wherein $R^3$ is a hydroxyl group may be prepared by reaction of substituted maleic anhydride (V) with amine (VI), wherein A is an optionally substituted isoxazole ring, in acetic acid to give maleimide (IV), and subsequent reduction with e.g. sodium borohydride to give compound (VII) (compound (I) wherein $R^3$ is hydroxyl), together with regioisomer (VIII) as a side-product (Scheme 1). Suitable conditions for achieving these transformations are disclosed in CH633678. Maleic anhydrides (V) can be prepared by literature methods (Journal of the Chemical Society, Perkin Transactions 1: Organic and Bio-Organic Chemistry (1972-1999), 1982, p. 215-222, EP1426365 A1, 2004, Journal of Organic Chemistry, 1998, vol. 63, 8, p. 2646-2655).

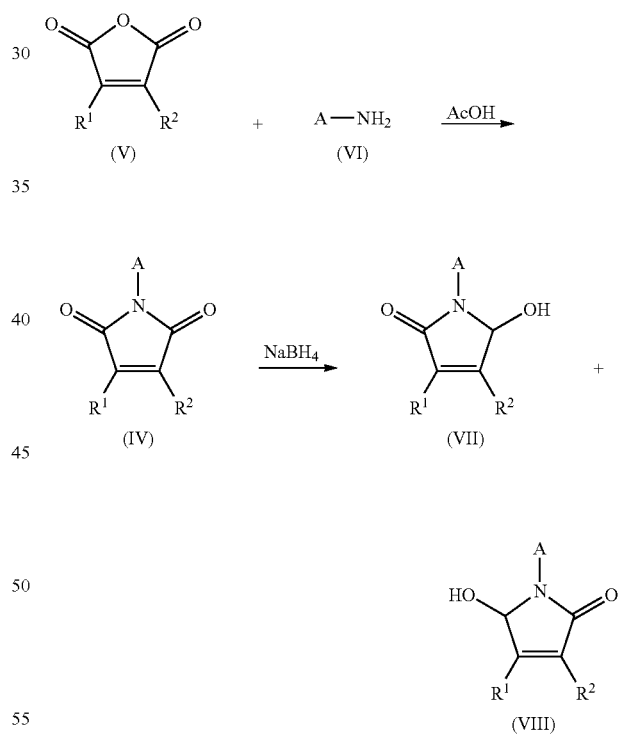

Scheme 1

Alternatively compounds of formula (VII) wherein $R^3$ is a hydroxyl group may be prepared by reaction of intermediates (IX) wherein $R^3$ is an appropriate leaving group, such as halogen or hydroxy (which in turn can be prepared as described in scheme 14) with the appropriate amino isoxazole (VI), in a suitable solvent, such as toluene to afford intermediate (X). Heating (X) in a suitable anhydride, such as propionic anhydride and a solvent such as toluene affords (XI). Heating (XI) in an acetic acid/water solution affords the desired final compounds (VII) (Scheme 2).

Scheme 2

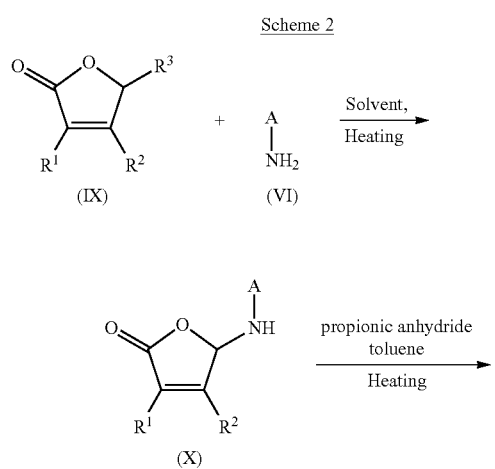

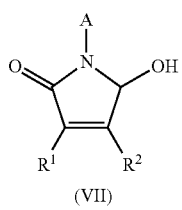

Alternatively, compounds of formula (VII), wherein $R^1$, $R^2$ and A are as described above can be prepared by acylating the appropriate amino isoxazole (VI) with compound (XIII) to give intermediate (XIV). (XIV) can then be converted by a Horner-Wadsworth-Emmons (HWE) olefination to give the intermediates (XVI) and (XVII) and cyclization under acidic conditions then leads to the desired product as shown in Scheme 3. Suitable conditions for achieving these transformations are disclosed e.g. in Tetrahedron Letters, 2008, vol. 49, p. 4029-4032.

Scheme 3

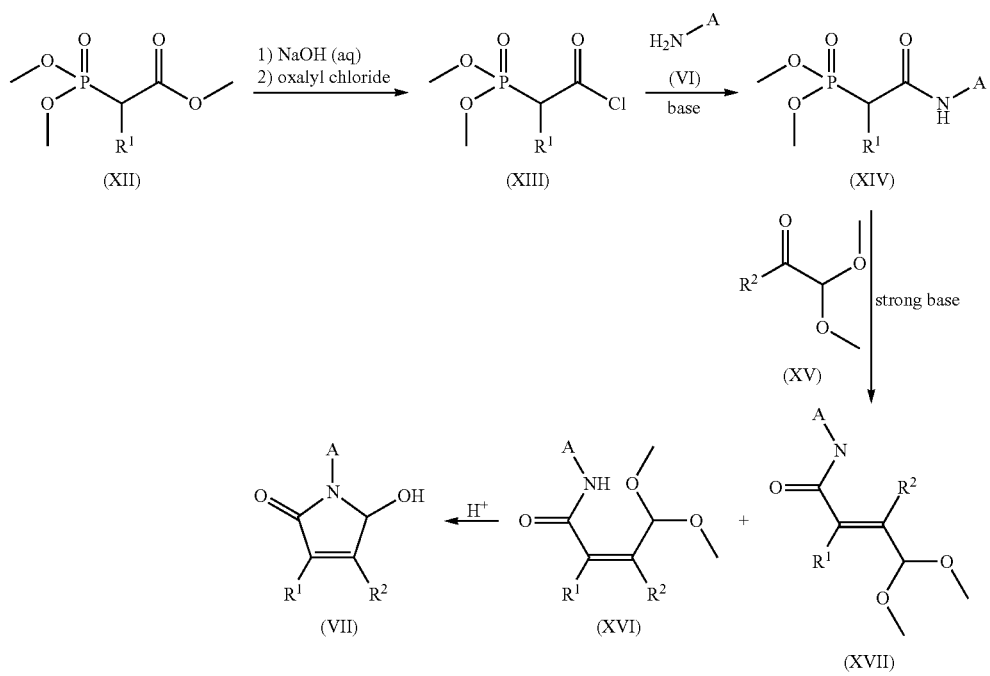

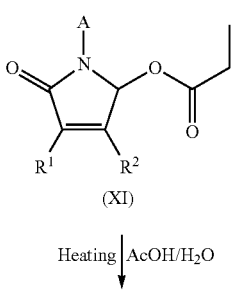

Alternatively, compounds of formula (I) wherein $R^1$ is alkoxy may be prepared by reaction of substituted isoxazole amine (VI), formaldehyde and an α-keto acid (XLVIII), in a suitable solvent and optionally in the presence of acid to give 2-hydroxy lactam (XVIII). Similar processes are described, e.g. in Clarke et al., JACS, 1933, 55, 4571-4587). Subsequent alkylation followed by halogenation, e.g. bromination and hydrolysis gives compounds of formula (VII) (scheme 4). Alternatively, intermediate (XIX) can be treated with suitable oxidants to lead to the desired products (VII) directly, or can be converted to compounds (XX), e.g. by treating with manganese triacetate in glacial acetic acid followed by hydrolysis to give compounds of formula (VII) (scheme 4). Suitable conditions for effecting these transformations are set out for example in J. March, Advanced Organic Chemistry, 4th ed. Wiley, New York, 1992; Canadian Journal of chemistry 1976, p. 3830 and references cited therein.

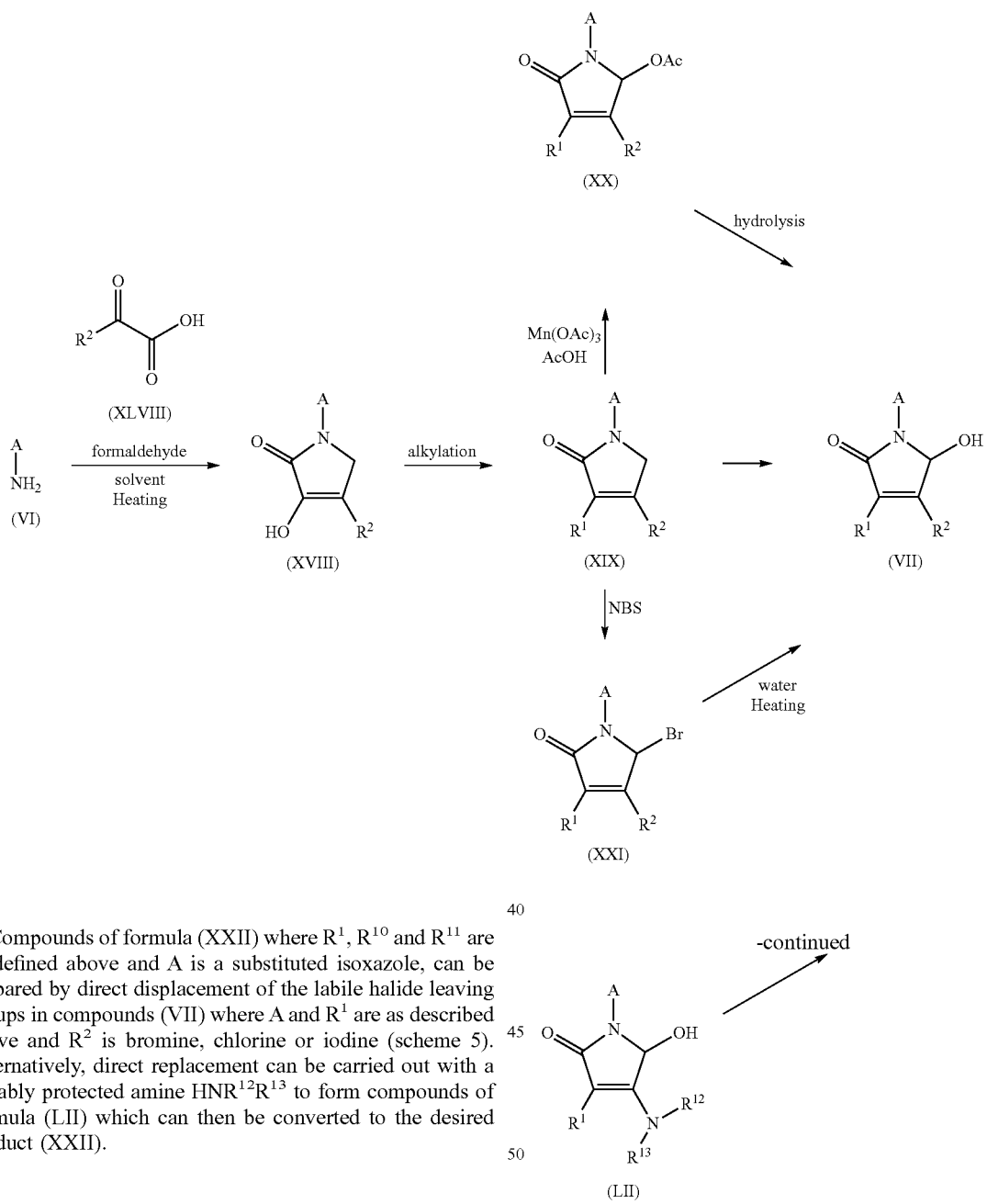

Compounds of formula (XXII) where $R^1$, $R^{10}$ and $R^{11}$ are as defined above and A is a substituted isoxazole, can be prepared by direct displacement of the labile halide leaving groups in compounds (VII) where A and $R^1$ are as described above and $R^2$ is bromine, chlorine or iodine (scheme 5). Alternatively, direct replacement can be carried out with a suitably protected amine $HNR^{12}R^{13}$ to form compounds of formula (LII) which can then be converted to the desired product (XXII).

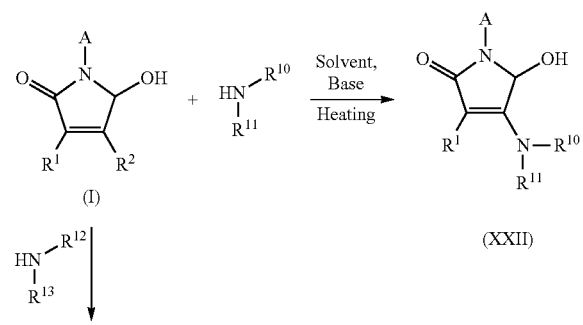

The relevant amino isoxazoles (XXIV) can be prepared by methods well known in the art, described e.g. in Gilchrist, T. L., Heterocyclic Chemistry (1992), $2^{nd}$ Ed, Longman Scientifc & Technical and John Wiley & Sons. Scheme 6 shows one example whereby a substituted oxonitrile (XXIII) is treated with hydroxyl amine under appropriate conditions of pH and temperature which is described, for example, in Takase et al Heterocycles 1991, 32(6), 1153-1158, to afford the desired isoxazole amine product (XXIV) (scheme 6). This method is particularly applicable for cases in which $R^b$ is sterically demanding.

Scheme 6

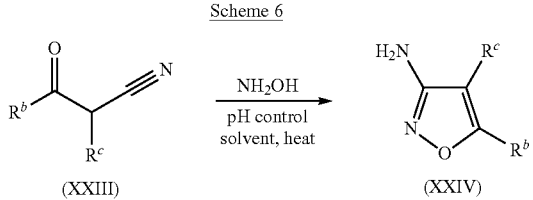

Depending on $R^b$, in order to influence the yield and regiochemical outcome of the condensation reaction, the substituted oxonitrile (XXIII) may be productively replaced in the forgoing scheme by oxo-protected derivatives, such as a ketal derivative (XXV, $R^d$=lower alkyl or taken together, an alkylene derivative to form a ketal ring). These derivatives are prepared from the corresponding (XXIII) under standard conditions for example as described in Chan et al. Synthesis 1983 203-205.

Compounds (XXVI) where $R^b$ is as defined above may be halogenated (i) under standard conditions to access intermediates (XXVII) where X is chlorine, bromine or iodine. (XXVI) can also be alkylated (ii) to form (XXIV), where Rc is methyl or ethyl (Scheme 7). These transformations are known in the literature and described, for example in WO2007100295 and Tetrahedron Letters, 2008, 49, 1, p. 189.

Scheme 7

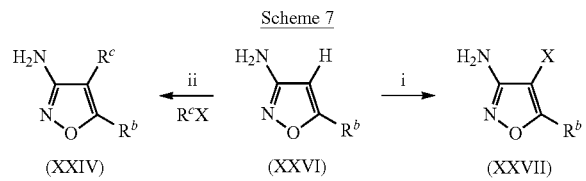

Compounds of formula (XXVIII) may be transformed to the corresponding carboxylic acid (XXX) or carboxylic amide (XXIX) under standard conditions (scheme 8). Suitable conditions for effecting these transformations will be known to those skilled in the art, and are set out for example in J. March, Advanced Organic Chemistry, 4th ed. Wiley, New York, 1992, and references cited therein.

Scheme 8

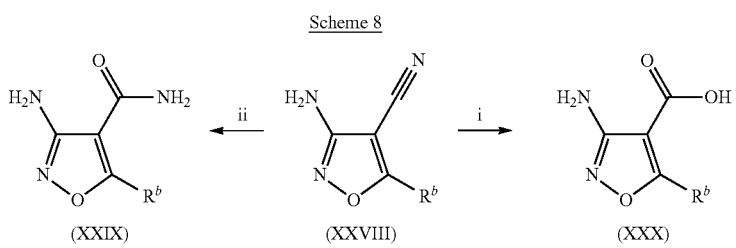

3-amino-4-nitrile substituted isoxazoles (XXVIII) may be prepared as shown in Scheme 9, as reported in the literature DE 2249163 A1

Scheme 9

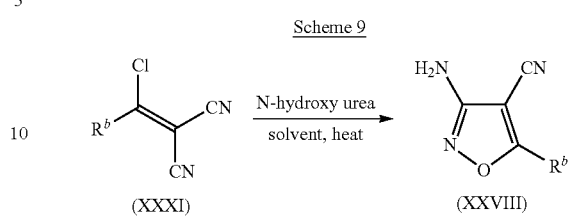

Nitrile vinyl chlorides (XXXI) can be prepared from the corresponding β-ketonitrile (XXXII) and a suitable chlorination reagent such as $PCl_5$ or $POCl_3$, in a suitable solvent, such as dichloromethane as shown in Scheme 10.

Scheme 10

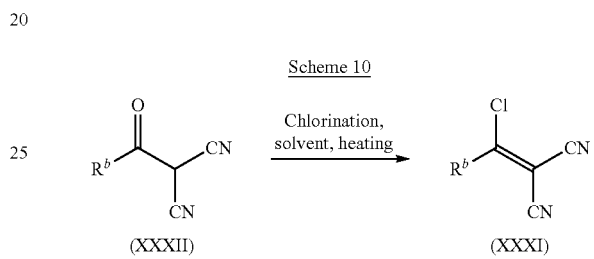

Scheme 11 illustrates preparation of the requisite 3-oxonitriles (XXIII) by reaction of an $R^b$ containing carboxylic ester (XXXIII) with an alkali metal salt of acetonitrile (XXXIV) (see for example U.S. Pat. No. 4,728,743).

Scheme 11

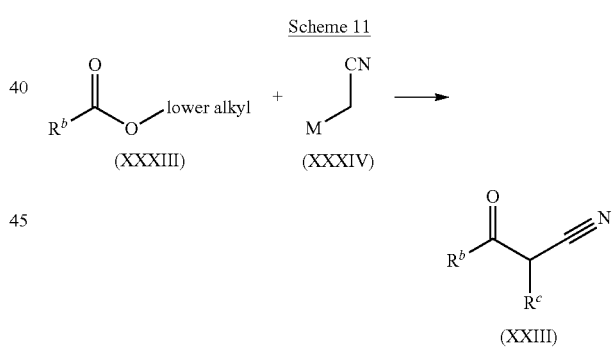

Alternatively, compounds of formula XXXII may be prepared by reaction of $R^b$ containing acid chloride (XXXV)

and an alkali metal salt of malononitrile (XXXVI) (scheme 12, see, for example DE 2249163 A1).

Scheme 12

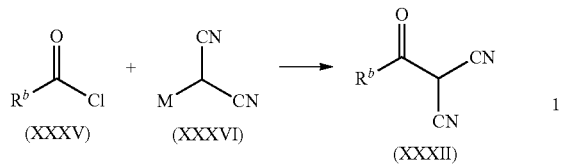

Compounds of formula (V) where $R^1$ is halogen, such as bromine, chlorine or iodine can be prepared by reacting the appropriate alkyl magnesium halide Grignard with Dimethyl acetylene dicarboxylate (scheme 13) by methods well known in the art and described in literature (Organic Letters, 2005, vol 7, 4, p. 605).

Scheme 13

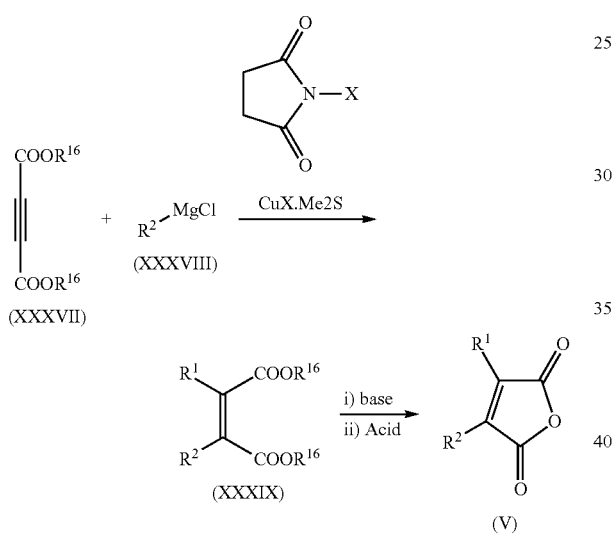

Compounds of formula (IX) where $R^1$ is halogen, such as bromine, chlorine or iodine may be prepared as shown in Scheme 14, as reported in the literature (Journal of Organic Chemistry, 1981, vol. 46, 8, p. 4889-4894; Journal of Organic Chemistry, 1990, vol. 55, 8, p. 2847-2855).

Scheme 14

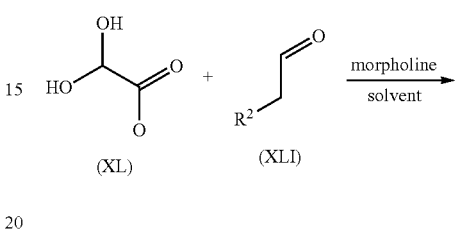

Compound (VII) may be halogenated (i), alkylated (ii), acylated (iii), sulfonylated (iv) or alkoxyacylated (v), under standard conditions to access other compounds having different values of $R^3$ (Scheme 15)

(Scheme 15)

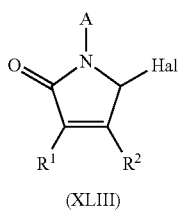

(XLIII)

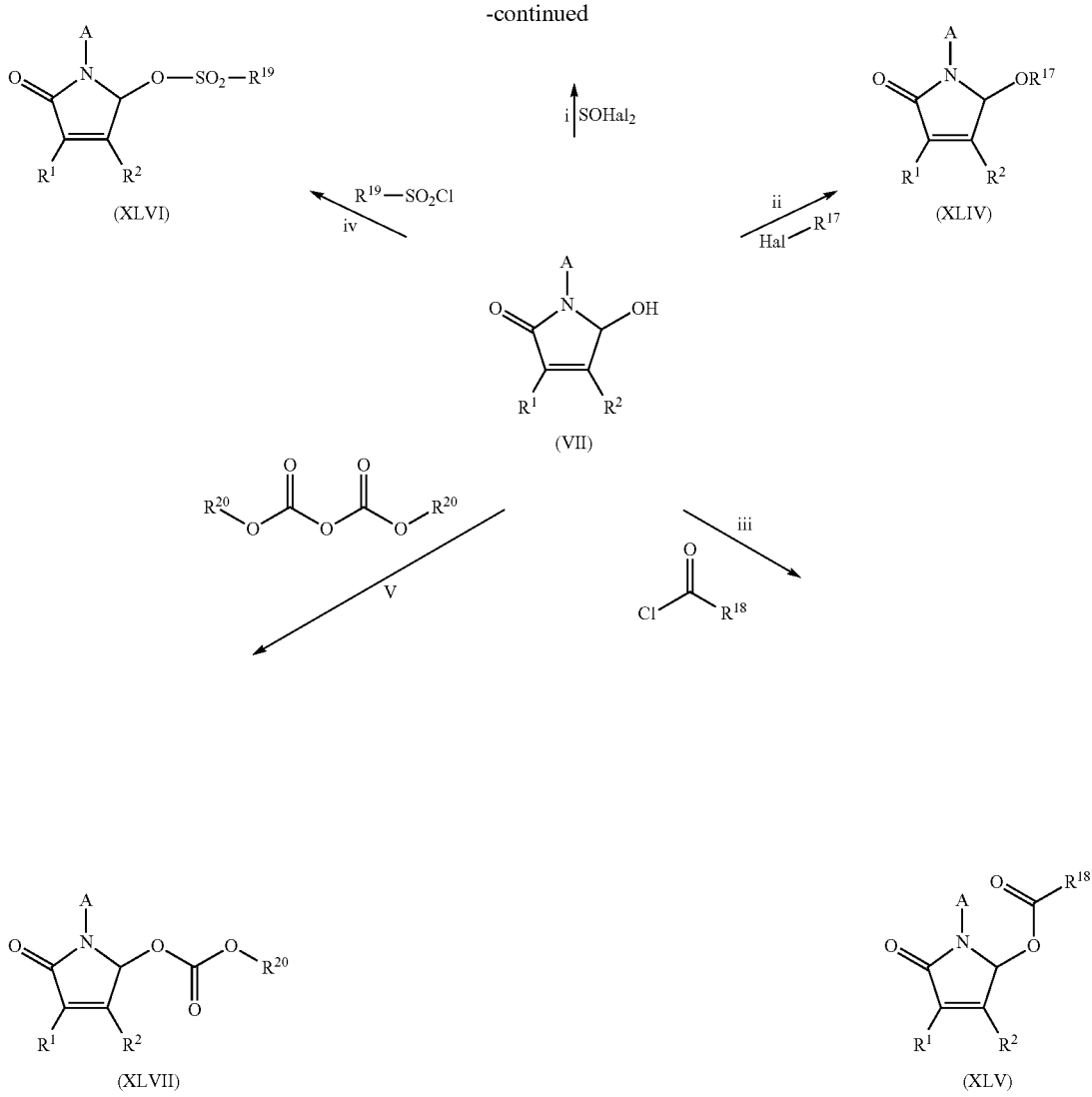

wherein $R^1$ and $R^2$ are as defined above, A is an optionally substituted isoxazole ring, Hal is halogen as defined above, $R^{17}$ is selected from $C_1$-$C_6$ alkyl, $C_2$-$C_6$ alkenyl, $C_2$-$C_6$ alkynyl; $R^{18}$ is selected from H and $C_1$-$C_5$ alkyl, $R^{19}$ is selected from $C_1$-$C_6$ alkyl and $C_6$-$C_{10}$ aryl optionally substituted with 1 to 3 groups independently selected from halogen, $C_1$-$C_3$ alkyl, and $C_1$-$C_3$ alkoxy and $R^{20}$ is selected from $C_1$-$C_5$ alkyl.

Suitable conditions for effecting transformations i to v will be known to those skilled in the art, and are set out for example in J. March, Advanced Organic Chemistry, 4th ed. Wiley, New York, 1992, and references cited therein.

Substituents $R^b$ and $R^c$ of formula (I) may be introduced via the isoxazole amine, as described e.g. in schemes 6-9, or may be introduced at any other stage of the synthesis, using standard functional group transformations (FTG). E.g. compounds of structure (LI), wherein $R^b$, $R^c$, $R^1$, $R^2$ are as described above and Q is —$CH_2$— or —C(=O)—, can be prepared from suitable precursors (XLVIII), either via (XLIX) or (L) as shown in scheme 16. (XLVIII) is accessible as outlined e.g. in scheme 1 (for Q is —C(=O)—) or scheme 4 (for —$CH_2$—). Compounds of formula (LI) can be further converted to target molecules, as outlined e.g. in scheme 1 (for Q is —C(=O)—) or scheme 4 (for —$CH_2$—).

(Scheme 16)

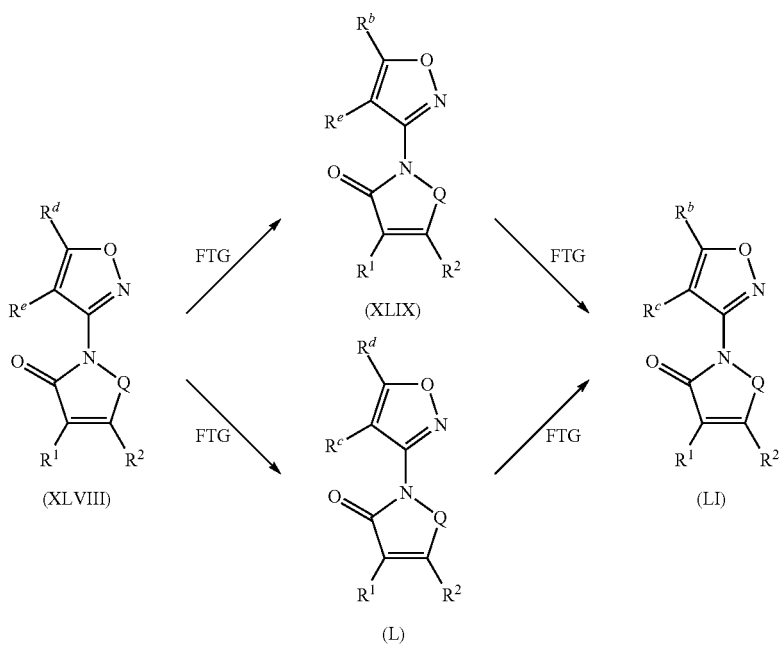

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. Therefore, the invention also relates to a herbicidal composition which comprises a herbicidally effective amount of a compound of formula (I) in addition to formulation adjuvants. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilizers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydro-furfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallization inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyloxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkyl pyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):

Emulsifiable Concentrates:
active ingredient: 1 to 95%, preferably 60 to 90
surface-active agent: 1 to 30%, preferably 5 to 20
liquid carrier: 1 to 80%, preferably 1 to 35

Dusts:
active ingredient: 0.1 to 10%, preferably 0.1 to 5
solid carrier: 99.9 to 90%, preferably 99.9 to 99

Suspension Concentrates:
active ingredient: 5 to 75%, preferably 10 to 50%
water: 94 to 24%, preferably 88 to 30
surface-active agent: 1 to 40%, preferably 2 to 30

Wettable Powders:
active ingredient: 0.5 to 90%, preferably 1 to 80
surface-active agent: 0.5 to 20%, preferably 1 to 15
solid carrier: 5 to 95%, preferably 15 to 90

Granules:
active ingredient: 0.1 to 30%, preferably 0.1 to 15
solid carrier: 99.5 to 70%, preferably 97 to 85

The following Examples further illustrate, but do not limit, the invention.

Formulation Examples for Herbicides of Formula (I) (%=% by Weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |

-continued

| F8. Suspension concentrates | a) | b) | c) | d) |
|---|---|---|---|---|
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention also provides a method of controlling plants which comprises applying to the plants or to the locus thereof a herbicidally effective amount of a compound of formula (I).

The invention also provides a method of inhibiting plant growth which comprises applying to the plants or to the locus thereof a herbicidally effective amount of a compound of formula (I).

The invention also provides a method of controlling weeds in crops of useful plants, comprising applying to said weeds or to the locus of said weeds, or to said useful plants or to the locus of said useful plants, a compound or a composition of the invention.

The invention also provides a method of selectively controlling grasses and/or weeds in crops of useful plants which comprises applying to the useful plants or locus thereof or to the area of cultivation a herbicidally effective amount of a compound of formula (I).

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation and includes not only areas where weeds may already be growing, but also areas where weeds have yet to emerge, and also to areas under cultivation with respect to crops of useful plants. "Areas under cultivation" include land on which the crop plants are already growing and land intended for cultivation with such crop plants. The term "weeds" as used herein means any undesired plant, and thus includes not only agronomically important weeds as described below, but also volunteer crop plants.

The compounds of the invention can be applied before or after planting of the crops, before weeds emerge (pre-emergence application) or after weeds emerge (post-emergence application), and are particularly effective when applied post-emergence to the weeds.

Crops of useful plants in which the composition according to the invention can be used include, but are not limited to, perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals, switchgrass, turf and vegetables, especially cereals, maize and soy beans.

The grasses and weeds to be controlled may be both monocotyledonous species, for example *Agrostis, Alopecurus, Avena, Brachiaria, Bromus, Cenchrus, Cyperus, Digitaria, Echinochloa, Eriochloa, Lolium, Monochoria, Panicum, Poa, Rottboellia, Sagittaria, Scirpus, Setaria, Sida* and *Sorghum*, and dicotyledonous species, for example *Abutilon, Amaranthus, Chenopodium, Chrysanthemum, Euphorbia, Galium, Ipomoea, Kochia, Nasturtium, Polygonum, Sida, Sinapis, Solanum, Stellaria, Veronica, Viola* and *Xanthium*.

Crops are to be understood as also including those crops which have been rendered tolerant to herbicides or classes of herbicides (e.g. auxins or ALS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, respectively.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NM (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Any method of application to weeds/crop of useful plant, or locus thereof, which is routinely used in agriculture may be used, for example application by spray or broadcast method typically after suitable dilution of a compound of formula (I) (whether said compound is formulated and/or in combination with one or more further active ingredients and/or safeners, as described herein).

The compounds of formula (I) according to the invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth, form yet further aspects of the invention. For the avoidance of doubt, mixtures of invention also include mixtures of two or more different compounds of formula (I). In particular, the present invention also relates to a composition of the invention which comprises at least one further herbicide in addition to the compound of formula (I).

When a compound of formula (I) is combined with at least one additional herbicide, the following mixtures of the compound of formula (I) are preferred. Compound of formula (I)+acetochlor, compound of formula (I)+acifluorfen, compound of formula (I)+acifluorfen-sodium, compound of formula (I)+aclonifen, compound of formula (I)+acrolein, compound of formula (I)+alachlor, compound of formula (I)+alloxydim, compound of formula (I)+allyl alcohol, compound of formula (I)+ametryn, compound of formula (I)+amicarbazone, compound of formula (I)+amidosulfuron, compound of formula (I)+aminocyclopyrachlor, compound of formula (I)+aminopyralid, compound of formula (I)+amitrole, compound of formula (I)+ammonium sulfamate, compound of formula (I)+anilofos, compound of formula (I)+asulam, compound of formula (I)+atrazine, compound of formula (I)+aviglycine, compound of formula (I)+azafenidin, compound of formula (I)+azimsulfuron, compound of formula (I)+BCPC, compound of formula (I)+beflubutamid, compound of formula (I)+benazolin, compound of formula (I)+bencarbazone, compound of formula (I)+benfluralin, compound of formula (I)+benfuresate, compound of formula (I)+bensulfuron, compound of formula (I)+bensulfuron-methyl, compound of formula (I)+bensulide, compound of formula (I)+bentazone, compound of formula (I)+benzfendizone, compound of formula (I)+benzobicyclon, compound of formula (I)+benzofenap, compound of formula (I)+bicyclopyrone, compound of formula (I)+bifenox, compound of formula (I)+bilanafos, compound of formula (I)+bispyribac, compound of formula (I)+bispyribac-sodium, compound of formula (I)+borax, compound of formula (I)+bromacil, compound of formula (I)+bromobutide, compound of formula (I)+bromophenoxim, compound of formula (I)+bromoxynil, compound of formula (I)+butachlor, compound of formula (I)+butafenacil, compound of formula (I)+butamifos, compound of formula (I)+butralin, compound of formula (I)+butroxydim, compound of formula (I)+butylate, compound of formula (I)+cacodylic acid, compound of formula (I)+calcium chlorate, compound of formula (I)+cafenstrole, compound of formula (I)+carbetamide, compound of formula (I)+carfentrazone, compound of formula (I)+carfentrazone-ethyl, compound of formula (I)+CDEA, compound of formula (I)+CEPC, compound of formula (I)+chlorflurenol, compound of formula (I)+chlorflurenol-methyl, compound of formula (I)+chloridazon, compound of formula (I)+chlorimuron, compound of formula (I)+chlorimuron-ethyl, compound of formula (I)+chloroacetic acid, compound of formula (I)+chlorotoluron, compound of formula (I)+chlorpropham, compound of formula (I)+chlorsulfuron, compound of formula (I)+chlorthal, compound of formula (I)+chlorthal-dimethyl, compound of formula (I)+cinidon-ethyl, compound of formula (I)+cinmethylin, compound of formula (I)+cinosulfuron, compound of formula (I)+cisanilide, compound of formula (I)+clethodim, compound of formula (I)+clodinafop, compound of formula (I)+clodinafop-propargyl, compound of formula (I)+clomazone, compound of formula (I)+clomeprop, compound of formula (I)+clopyralid, compound of formula (I)+cloransulam, compound of formula (I)+cloransulam-methyl, compound of formula (I)+CMA, compound of formula (I)+4-CPB, compound of formula (I)+CPMF, compound of formula (I)+4-CPP, compound of formula (I)+CPPC, compound of formula (I)+cresol, compound of formula (I)+cumyluron, compound of formula (I)+cyanamide, compound of formula (I)+cyanazine, compound of formula (I)+cycloate, compound of formula (I)+cyclosulfamuron, compound of formula (I)+cycloxydim, compound of formula (I)+cyhalofop, compound of formula (I)+cyhalofop-butyl, compound of formula (I)+2,4-D, compound of formula (I)+3,4-DA, compound of formula (I)+daimuron, compound of formula (I)+dalapon, compound of formula (I)+dazomet, compound of formula (I)+2,4-DB, compound of formula (I)+3,4-DB, compound of formula (I)+2,4-DEB, compound of formula (I)+desmedipham, compound of formula (I)+desmetryn, compound of formula (I)+dicamba, compound of formula (I)+dichlobenil, compound of formula (I)+ortho-dichlorobenzene, compound of formula (I)+para-dichlorobenzene, compound of formula (I)+dichlorprop, compound of formula (I)+dichlorprop-P, compound of formula (I)+diclofop, compound of formula (I)+diclofop-methyl, compound of formula (I)+diclosulam, compound of formula (I)+difenzoquat, compound of formula (I)+difenzoquat metilsulfate, compound of formula (I)+diflufenican, compound of formula (I)+diflufenzopyr, compound of formula (I)+dimefuron, compound of formula (I)+dimepiperate, compound of formula (I)+dimethachlor, compound of formula (I)+dimethametryn, compound of formula (I)+dimethenamid, compound of formula (I)+dimethenamid-P, compound of formula (I)+dimethipin, compound of formula (I)+dimethylarsinic acid, compound of formula (I)+dinitramine, compound of formula (I)+dinoterb, compound of formula (I)+diphenamid, compound of formula (I)+dipropetryn, compound of formula (I)+diquat, compound of formula (I)+diquat dibromide, compound of formula (I)+dithiopyr, compound of formula (I)+diuron, compound of formula (I)+DNOC, compound of formula (I)+3,4-DP, compound of formula (I)+DSMA, compound of formula (I)+EBEP, compound of formula (I)+endothal, compound of formula (I)+EPTC, compound of formula (I)+esprocarb, compound of formula (I)+ethalfluralin, compound of formula (I)+ethametsulfuron, compound of formula (I)+ethametsulfuron-methyl, compound of formula (I)+ethephon, compound of formula (I)+ethofumesate, compound of formula (I)+ethoxyfen, compound of formula (I)+ethoxysulfuron, compound of formula (I)+etobenzanid, compound of formula (I)+fenoxaprop, compound of formula (I)+fenoxaprop-P, compound of formula (I)+fenoxaprop-ethyl, compound of formula (I)+fenoxaprop-P-ethyl, compound of formula (I)+fentrazamide, compound of formula (I)+ferrous sulfate, compound of formula (I)+flamprop-M, compound of formula (I)+flazasulfuron, compound of formula (I)+florasulam, compound of formula (I)+fluazifop, compound of formula (I)+fluazifop-butyl, compound of formula (I)+fluazifop-P, compound of formula (I)+fluazifop-P-butyl, formula (I)+fluazolate, compound of formula (I)+flucarbazone, compound of formula (I)+flucarbazone-sodium, compound of formula (I)+flucetosulfuron, compound of formula (I)+fluchloralin, compound of formula (I)+flufenacet, compound of formula (I)+flufenpyr, compound of formula (I)+flufenpyr-ethyl, formula (I)+flumetralin, compound of formula (I)+flumetsulam, compound of formula (I)+flumiclorac, compound of formula (I)+flumiclorac-pentyl, compound of formula (I)+flumioxazin, formula (I)+flumipropin, compound of formula (I)+fluometuron, compound of formula (I)+fluoroglycofen, compound of formula (I)+fluoroglycofen-ethyl, formula (I)+fluoxaprop, compound of formula (I)+flupoxam, compound of formula (I)+flupropacil, compound of formula (I)+flupropanate, compound of formula (I)+flupyrsulfuron, compound of formula (I)+flupyrsulfuron-methyl-sodium, compound of formula (I)+flurenol, compound of formula (I)+fluridone, compound of formula (I)+flurochloridone, compound of formula (I)+fluroxypyr, compound of formula (I)+flurtamone, compound of formula (I)+fluthiacet, compound of formula (I)+fluthiacet-methyl, compound of formula (I)+fomesafen, compound of formula (I)+foramsulfuron, compound of formula (I)+fosamine, compound of formula (I)+glufosinate, compound of formula (I)+glufosinate-ammonium, compound of formula (I)+glyphosate, compound of formula (I)+halauxifen, compound of formula (I)+halauxifen-methyl, compound of formula (I)+halosulfuron, compound of formula (I)+halosulfuron-methyl, compound of formula (I)+haloxyfop, compound of formula (I)+haloxyfop-P, compound of formula (I)+HC-252, compound of formula (I)+hexazinone, compound of formula (I)+imazamethabenz, compound of formula (I)+imazamethabenz-methyl, compound of formula (I)+imazamox, compound of formula (I)+imazapic, compound of formula (I)+imazapyr, compound of formula (I)+imazaquin, compound of formula (I)+imazethapyr, compound of formula (I)+imazosulfuron, compound of formula (I)+indanofan, compound of formula (I) and indaziflam, compound of formula (I)+iodomethane, compound of formula (I)+iodosulfuron, compound of formula (I)+iodosulfuron-methyl-sodium, compound of formula (I)+ioxynil, compound of formula (I) and ipfencarbazone, compound of formula (I)+isoproturon, compound of formula (I)+isouron, compound of formula (I)+isoxaben, compound of formula (I)+isoxachlortole, compound of formula (I)+isoxaflutole, compound of formula (I)+isoxapyrifop, compound of formula (I)+karbutilate, compound of formula (I)+lactofen, compound of formula (I)+lenacil, compound of formula (I)+linuron, compound of formula (I)+MAA, compound of formula (I)+MAMA, compound of formula (I)+MCPA, compound of formula (I)+MCPA-thioethyl, compound of formula (I)+MCPB, compound of formula (I)+mecoprop, compound of formula (I)+mecoprop-P, compound of formula (I)+mefenacet, compound of formula (I)+mefluidide, compound of formula (I)+mesosulfuron, compound of formula (I)+mesosulfuron-methyl, compound of formula (I)+mesotrione, compound of formula (I)+metam, compound of formula (I)+metamifop, compound of formula (I)+metamitron, compound of formula (I)+metazachlor, compound of formula (I)+metazosulfuron, compound of formula (I)+methabenzthiazuron, formula (I)+methazole, a compound of formula (I) and methiozolin, compound of formula (I)+methylarsonic acid, compound of formula (I)+methyldymron, compound of formula (I)+methyl isothiocyanate, compound of formula (I)+metobenzuron, compound of formula (I)+metobromuron, compound of formula (I)+metolachlor, compound of formula (I)+S-metolachlor, compound of formula (I)+metosulam, compound of formula (I)+metoxuron, compound of formula (I)+metribuzin, compound of formula (I)+metsulfuron, compound of formula (I)+metsulfuron-methyl, compound of formula (I)+MK-616, compound of formula (I)+molinate, compound of formula (I)+monolinuron, compound of formula (I)+monosulfuron, compound of formula (I)+monosulfuron-ester, compound of formula (I)+MSMA, compound of formula (I)+naproanilide, compound of formula (I)+napropamide, compound of formula (I)+naptalam, formula (I)+NDA-402989, compound of formula (I)+neburon, compound of formula (I)+nicosulfuron, compound of formula (I)+nipyraclofen, compound of formula (I)+n-methyl glyphosate, compound of formula (I)+nonanoic acid, compound of formula (I)+norflurazon, compound of formula (I)+oleic acid (fatty acids), compound of formula (I)+orbencarb, compound of formula (I)+orthosulfamuron, compound of formula (I)+oryzalin, compound of formula (I)+oxadiargyl, compound of formula (I)+oxadiazon, compound of formula (I)+oxasulfuron, compound of formula (I)+oxaziclomefone, compound of formula (I)+oxyfluorfen, compound of formula (I)+paraquat, compound of formula (I)+paraquat dichloride, compound of formula (I)+pebulate, compound of formula (I)+pendimethalin, compound of formula (I)+penoxsulam, compound of formula (I)+pentachlorophenol, compound of formula (I)+pentanochlor, compound of formula (I)+pentoxazone, compound of formula (I)+pethoxamid, compound of formula (I)+petrolium oils, compound of formula (I)+phenmedipham, compound of formula (I)+phenmedipham-ethyl, compound of formula (I)+picloram, compound of formula (I)+picolinafen, compound of formula (I)+pinoxaden, compound of formula (I)+piperophos, compound of formula (I)+potassium arsenite, compound of formula (I)+potassium azide, compound of formula (I)+pretilachlor, compound of formula (I)+primisulfuron, compound of formula (I)+primisulfuron-methyl, compound of formula (I)+prodiamine, compound of formula (I)+profluazol, compound of formula (I)+profoxydim, compound of formula (I)+prohexadione-calcium, compound of formula (I)+prometon, compound of formula (I)+prometryn, compound of formula (I)+propachlor, compound of formula (I)+propanil, compound of formula (I)+propaquizafop, compound of formula (I)+propazine, compound of formula (I)+propham, compound of formula (I)+propisochlor, compound of formula (I)+propoxycarbazone, compound of formula (I)+propoxycarbazone-sodium, compound of formula (I)+propyzamide, compound of formula (I)+prosulfocarb, compound of formula (I)+prosulfuron, compound of formula (I)+pyraclonil, compound of formula (I)+pyraflufen, compound of formula (I)+pyraflufen-ethyl, formula (I)+pyrasulfotole, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyributicarb, compound of formula (I)+pyridafol, compound of formula (I)+pyridate, compound of formula (I)+pyriftalid, compound of formula (I)+pyriminobac, compound of formula (I)+pyriminobac-methyl, compound of formula (I)+pyrimisulfan, compound of formula (I)+pyrithiobac, compound of formula (I)+pyrithiobac-sodium, compound of formula (I)+pyroxasulfone, compound of formula (I)+pyroxulam, compound of formula (I)+quinclorac, compound of formula (I)+quinmerac, compound of formula (I)+quinoclamine, compound of formula (I)+quizalofop, compound of formula (I)+quizalofop-P, compound of formula (I)+quizalofop-ethyl, compound of formula (I)+quizalofop-P-ethyl, compound of formula (I)+rimsulfuron, compound of formula (I)+saflufenacil, compound of formula (I)+sethoxydim, compound of formula (I)+siduron, compound of formula (I)+simazine, compound of formula (I)+simetryn, compound of formula (I)+SMA, compound of formula (I)+sodium arsenite, compound of formula (I)+sodium azide, compound of formula (I)+sodium chlorate, compound of formula (I)+sulcotrione, compound of formula (I)+sulfentrazone, compound of formula (I)+sulfometuron, compound of formula (I)+sulfometuron-methyl, compound of formula (I)+sulfosate, compound of formula (I)+sulfosulfuron, compound of formula (I)+sulfuric acid, compound of formula (I)+tar oils, compound of formula (I)+2,3,6-TBA, compound of formula (I)+TCA, compound of formula (I)+TCA-sodium, compound of formula (I)+tebutam, compound of formula (I)+tebuthiuron, compound of formula (I)+tefuryltrione, compound of formula 1+tembotrione, compound of formula (I)+tepraloxydim, compound of formula (I)+terbacil, compound of formula (I)+terbumeton, compound of formula (I)+terbuthylazine, compound of formula (I)+terbutryn, compound of formula (I)+thenylchlor, compound of formula (I)+thiazafluron, compound of formula (I)+thiazopyr, compound of formula (I)+thifensulfuron, compound of formula (I)+thiencarbazone, compound of formula (I)+thifensulfuron-methyl, compound of formula (I)+thiobencarb, compound of formula (I)+tiocarbazil, compound of formula (I)+topramezone, compound of formula (I)+tralkoxydim, compound of formula (I)+triafamone, compound of formula (I)+tri-allate, compound of formula (I)+triasulfuron, compound of formula (I)+triaziflam, compound of formula (I)+tribenuron, compound of formula (I)+tribenuron-methyl, compound of formula (I)+tricamba, compound of formula (I)+triclopyr, compound of formula (I)+trietazine, compound of formula (I)+trifloxysulfuron, compound of formula (I)+trifloxysulfuron-sodium, compound of formula (I)+trifluralin, compound of formula (I)+triflusulfuron, compound of formula (I)+triflusulfuron-methyl, compound of formula (I)+trifop, compound of formula (I)+trifop-methyl, compound of formula (I)+trihydroxytriazine, compound of formula (I)+trinexapac-ethyl, compound of formula (I)+tritosulfuron, compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula (I)+2-[[8-chloro-3,4-dihydro-4-(4-methoxyphenyl)-3-oxo-2-quinoxalinyl]carbonyl]-1,3-cyclohexanedione and the compound of formula (I)+VX-573.

In particular, the following mixtures are important:

mixtures of a compound of formula (I) with an acetanilide (e.g. compound of formula (I)+acetochlor, compound of formula (I)+dimethenamid, compound of formula (I)+metolachlor, compound of formula (I)+S-metolachlor, or compound of formula (I)+pretilachlor);

mixtures of a compound of formula (I) with an HPPD inhibitor (e.g. compound of formula (I)+isoxaflutole, compound of formula (I)+mesotrione, compound of formula (I)+pyrasulfotole, compound of formula (I)+sulcotrione, compound of formula (I)+tembotrione, compound of formula (I)+topramezone, compound of formula (I)+bicyclopyrone);

mixtures of a compound of formula (I) with a triazine (e.g. compound of formula (I)+atrazine, or compound of formula (I)+terbuthylazine);

mixtures of a compound of formula (I) with a PPO inhibitor (e.g. compound of formula (I)+acifluorfen-sodium, compound of formula (I)+butafenacil, compound of formula (I)+carfentrazone-ethyl, compound of formula (I)+cinidon-ethyl, compound of formula (I)+flumioxazin, compound of formula (I)+fomesafen, compound of formula (I)+lactofen, or compound of formula (I)+SYN 523 ([3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

mixtures of a compound of formula (I) with glyphosate;

mixtures of a compound of formula (I) with glufosinate-ammonium.

Particularly preferred are mixtures of the compound of formula (I) with mesotrione, bicyclopyrone, isoxaflutole, tembotrione, topramezone, sulcotrione, pyrasulfotole, metolachlor, S-metolachlor, acetochlor, pyroxasulfone, P-dimethenamid, dimethenamid, flufenacet, pethoxamid, atrazine, terbuthylazine, bromoxynil, metribuzin, amicarbazone, bentazone, ametryn, hexazinone, diuron, tebuthiuron, glyphosate, paraquat, diquat, glufosinate, acifluorfen-sodium, butafenacil, carfentrazone-ethyl, cinidon-ethyl, flumioxazin, fomesafen, lactofen, [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester.

Whilst two-way mixtures of a compound of formula (I) and another herbicide are explicitly disclosed above, the skilled man will appreciate that the invention extends to three-way, and further multiple combinations comprising the above two-way mixtures. In particular, the invention extends to:

mixtures of a compound of formula (I) with a triazine and an HPPD inhibitor (e.g. compound of formula (I)+triazine+isoxaflutole, compound of formula (I)+triazine+mesotrione, compound of formula (I)+triazine+pyrasulfotole, compound of formula (I)+triazine+sulcotrione, compound of formula (I)+triazine+tembotrione, compound of formula (I)+triazine+topramezone, compound of formula (I)+triazine+bicyclopyrone);

mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+bicyclopyrone);

mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+bicyclopyrone);

The mixing partners of the compound of formula (I) may also be in the form of esters or salts, as mentioned e.g. in The Pesticide Manual, 14th Edition (BCPC), 2006. The reference to acifluorfen-sodium also applies to acifluorfen, the reference to dimethenamid also applies to dimethenamid-P, the reference to glufosinate-ammonium also applies to glufosinate, the reference to bensulfuron-methyl also applies to bensulfuron, the reference to cloransulam-methyl also applies to cloransulam, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further active ingredients, in particular with one or more further herbicides, can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. Where a compound of formula (I) is combined with a safener, the following combinations of the compound of formula (I) and the safener are particularly preferred. Compound of formula (I)+AD 67 (MON 4660), compound of formula (I)+benoxacor, compound of formula (I)+cloquintocet-mexyl, compound of formula (I)+cyometrinil and a compound of formula (I)+the corresponding (Z) isomer of cyometrinil, compound of formula (I)+cyprosulfamide (CAS RN 221667-31-8), compound of formula (I)+dichlormid, compound of formula (I) and dicyclonon, compound of formula (I) and dietholate, compound of formula (I)+fenchlorazole-ethyl, compound of formula (I)+fenclorim, compound of formula (I)+flurazole, compound of formula (I)+fluxofenim, compound of formula (I)+furilazole and a compound of formula (I)+the corresponding R isomer or furilazome, compound of formula (I)+isoxadifen-ethyl, compound of formula (I)+mefenpyr-diethyl, compound of formula (I) and mephenate, compound of formula (I)+oxabetrinil, compound of formula (I)+naphthalic anhydride (CAS RN 81-84-5), compound of formula (I) and TI-35, compound of formula (I)+N-isopropyl-4-(2-methoxy-benzoylsulfamoyl)-benzamide (CAS RN 221668-34-4) and a compound of formula (I)+N-(2-methoxybenzoyl)-4-[(methylaminocarbonyl)amino]benzenesulfonamide. Particularly preferred are mixtures of a compound of formula (I) with benoxacor, a compound of formula (I) with cloquintocet-mexyl, a compound of formula (I)+cyprosulfamide and a compound of formula (I) with N-(2-methoxybenzoyl)-4-[(methylaminocarbonyl)amino]benzenesulfonamide.

The safeners of the compound of formula (I) may also be in the form of esters or salts, as mentioned e.g. in The Pesticide Manual, 14th Edition (BCPC), 2006. The reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the abovementioned formulations (in which case "active ingredient" relates to the respective mixture of compound of formula (I) and any further active ingredient, in particular a further herbicide, with the safener).

It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with tembotrione and a safener.

Mixtures of a compound of formula (I) with topramezone and a safener.

Mixtures of a compound of formula (I) with bicyclopyrone and a safener.

Mixtures of a compound of formula (I) with a triazine and a safener.

Mixtures of a compound of formula (I) with a triazine and isoxaflutole and a safener.

Mixtures of a compound of formula (I) with a triazine and mesotrione and a safener.

Mixtures of a compound of formula (I) with a triazine and sulcotrione and a safener.

Mixtures of a compound of formula (I) with a triazine and tembotrione and a safener.

Mixtures of a compound of formula (I) with a triazine and topramezone and a safener.

Mixtures of a compound of formula (I) with a triazine and bicyclopyrone and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glyphosate and tembotrione and a safener.

Mixtures of a compound of formula (I) with glyphosate and topramezone and a safener.

Mixtures of a compound of formula (I) with glyphosate and bicyclopyrone and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with glufosinate-ammonium and tembotrione and a safener.

Mixtures of a compound of formula (I) with glufosinate-ammonium and topramezone and a safener.

Mixtures of a compound of formula (I) with glufosinate-ammonium and bicyclopyrone and a safener.

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Preparation Examples

The following abbreviations were used in this section: s=singlet; bs=broad singlet; d=doublet; dd=double doublet; dt=double triplet; t=triplet, tt=triple triplet, q=quartet, sept=septet; m=multiplet; RT=retention time, $MH^+$=molecular mass of the molecular cation.

1H NMR spectra were recorded at 400 MHz either on a Varian Unity Inova instrument 400 MHz or on a Bruker AVANCE—II instrument.

Preparation Examples

Example 1

Preparation of 3-(4-chloro-2-hydroxy-3-methyl-5-oxo-2H-pyrrol-1-yl)-5-isopropyl-isoxazole-4-carbonitrile (A44)

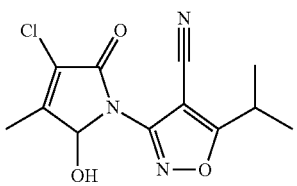 [SMILES: CC1=C(Cl)C(=O)N(c2noc(C(C)C)c2C#N)C1O]

Procedure for Synthesis of 2-(2-methylpropanoyl)propanedinitrile (Step-1)

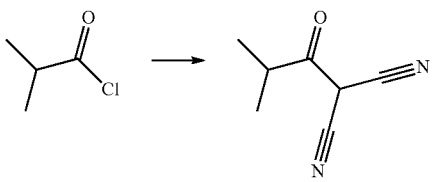

2-methyl propanoyl chloride (30.0 g, 281.55 mmol) and propanedinitrile (18.58 g, 278.4 mmol) were dissolved in toluene (300 ml) and cooled to 0° C. with stirring. To this reaction mixture, triethylamine (56.96 g, 557.3 mmol) was added and stirred for 1 h at 0° C. The reaction mixture was diluted with water (250 ml), acidified with concentrated sulphuric acid till acidic pH and extracted with ethyl acetate (500 ml×3). The organic layers were combined, washed with water (2×250 mL), dried over anhydrous sodium sulphate and concentrated under vacuum to give a crude mass. The crude mass was further purified using silica gel column chromatography to give the desired compound (34 g, 88% yield).

1H NMR (CDCl$_3$): 3.1 (m, 1H), 1.02 (d, 6H)

Procedure for Synthesis of 2-(1-chloro-2-methyl-propylidene)propanedinitrile (Step-2)

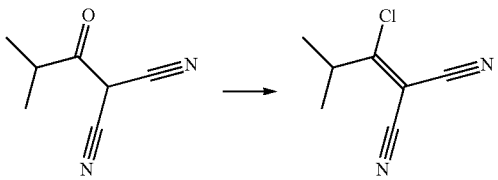

To a solution of 2-(2-methylpropanoyl)propanedinitrile (34 g, 249.72 mmol) in dichloromethane (340 ml), phosphorus pentachloride (57.2 g, 274.7 mmol) was added slowly and stirred at room temperature for 18 h. The reaction mixture was cooled to 0° C., quenched slowly with ice cold water (250 ml) and the aqueous layer was extracted with dichloromethane (400 ml×3). The combined organic layer was washed with water (200 ml×2) and then with sodium bicarbonate solution (100 ml). The organic layer was dried over sodium sulfate and concentrated under vacuum to give a crude mass. The crude mass was further purified using silica gel column chromatography to give the desired compound (29 g, 75% yield).

$^1$H NMR (CDCl$_3$): 2.86 (m, 1H), 1.05 (d, 6H)

Procedure for Synthesis of 3-amino-5-isopropyl-isoxazole-4-carbonitrile (Step-3)

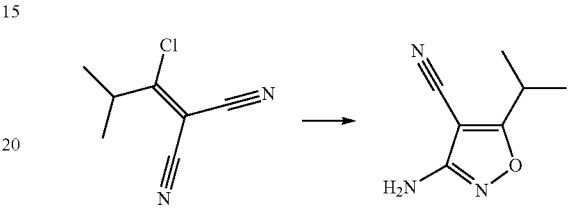

N-hydroxy urea (16.03 g, 206.3 mmol) was added to a solution of sodium hydroxide (8.25 g, 206.34 mmol) in water (87 ml) at 0° C. and stirred for 5 minutes. To this solution, 2-(1-chloro-2-methylpropylidine)propanedinitrile (29 g, 187.58 mmol) in methanol (87 ml) was added and stirred at room temperature for 18 h. The reaction mixture was then extracted with ethyl acetate (250×3 ml). The combined organic layer was washed with water (200 ml×2), dried over sodium sulfate and concentrated under vacuum to give a crude mass. The crude mass was further purified using silica gel column chromatography to give the desired compound (28.3 g, 55% yield).

$^1$H NMR (CDCl$_3$): 4.46 (br s, 2H), 3.18 (m, 1H), 1.37 (d, 6H).

Procedure for Synthesis of 3-(3-chloro-4-methyl-2,5-dioxo-pyrrol-1-yl)-5-isopropyl-isoxazole-4-carbonitrile (Step-4)

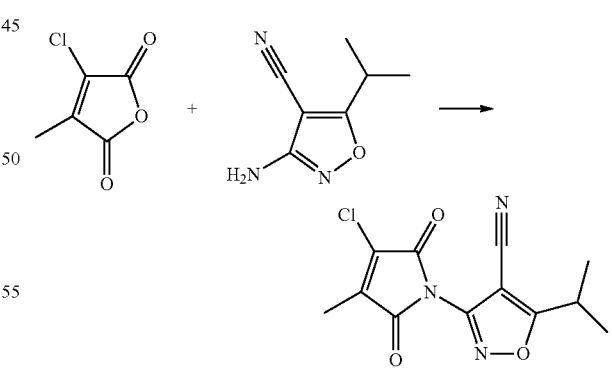

3-amino-5-isopropyl-isoxazole-4-carbonitrile amine (1.0 g, 6.66 mmol) and 3-chloro-4-methyl-furan-2,5-dione (1.06 g, 7.2 mmol) were dissolved in acetic acid (10 ml) and refluxed for 18 hours. The reaction mixture was cooled to room temperature, quenched with water (30 ml)) and extracted with ethyl acetate (60 ml×3). The combined organic layer was washed with water (50 ml×2), dried over sodium sulfate and concentrated under vacuum to give a crude mass. The crude mass was further purified using silica gel column chromatography to give the desired compound (0.73 g, 40% yield).

$^1$H NMR (CDCl$_3$): 2.2 (s, 3H), 3.4 (m, 1H), 1.3 (d, 6H).

Procedure for Synthesis of 3-(4-chloro-2-hydroxy-3-methyl-5-oxo-2H-pyrrol-1-yl)-5-isopropyl-isoxazole-4-carbonitrile (Step-5)

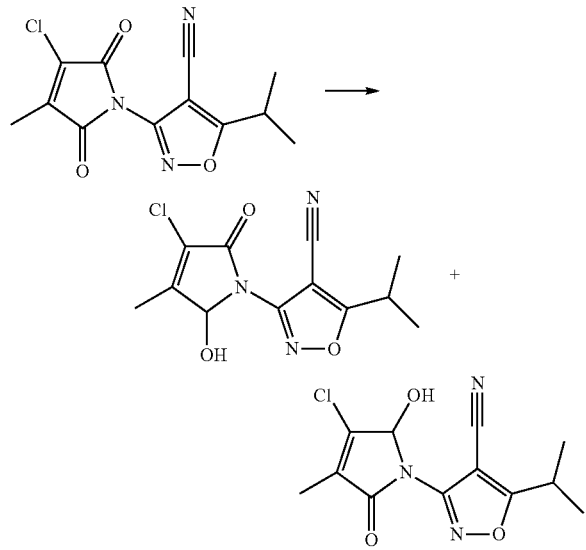

To a solution of 3-(3-chloro-4-methyl-2,5-dioxo-pyrrol-1-yl)-5-isopropyl-isoxazole-4-carbonitrile (0.73 g, 2.6 mmol) in tetrahydrofuran (7 ml) and methanol (7 ml) at −30° C., sodium borohydride (0.099, 2.6 mmol) was added and stirred for 2 hours at −30° C. The reaction mixture was quenched with dilute acetic acid till acidic pH, diluted with water (25 ml) and extracted with ethyl acetate (75 ml×3). Aqueous layer was extracted with more ethyl acetate (50 ml). The combined organic layer was washed with water (75 ml×2), dried over sodium sulfate and concentrated under vacuum to give a crude mass. The crude mass was further purified using preparative HPLC to give the desired compound A44 (0.34 g, 46% yield) along with the other isomer (0.15 g, 20% yield).

Example 2

Preparation of 1-(5-tert-butylisoxazol-3-yl)-4-chloro-2-hydroxy-3-methyl-2H-pyrrol-5-one (A2)

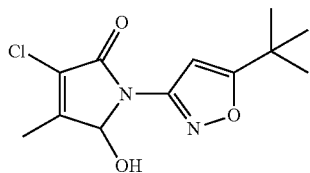 [SMILES: CC1=C(Cl)C(=O)N(c2cc(C(C)(C)C)on2)C1O]

Procedure for Synthesis of 2-ethoxy-3-methyl-2H-furan-5-one (Step 1)

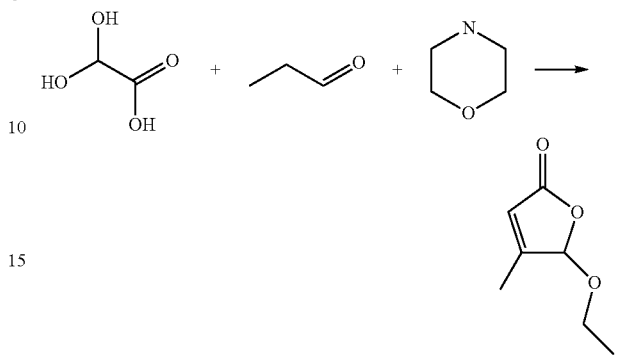

To the stirred solution of 2,2-dihydroxyacetic acid (10 g, 108.63 mmol) in ethanol (80 mL) was added morpholine (10.35 mL, 119.6 mmol) at 0° C. and stirred at same temperature for 20 min. To this solution, propanal (8.56 mL, 120 mmol) was added at 0° C. and allowed to stir at room temperature for 1 h. The reaction mixture was then refluxed for 12 h. Excess of ethanol was removed under vacuo and reaction mass was dried under the vacuum. The crude mass was taken in ethyl acetate (250 mL) and washed with water (2×50 mL); the organic layer was dried over anhydrous sodium sulfate, filtered and concentrated to obtained crude product which was then dissolved in ethanol (35.79 mL). To this ethanolic solution, 10% HCl in dioxane (70 mL) was added and refluxed for 12 h. The solvents were evaporated under vacuum. The crude mass was diluted with ethyl acetate (100 mL), hydrochloride salt formed was filtered off through celite bed and the cake was washed with ethyl acetate (250 mL). The filtrate and the washings were combined, washed with 10% aqueous sodium bicarbonate solution (50 mL×2), dried over anhydrous sodium sulfate and concentrated under vacuum. The residue was purified over silica gel column chromatography to give the desired product (4.64 g, 73% yield).

$^1$H NMR (CDCl$_3$): 5.85 (s, 1H), 5.65 (s, 1H), 3.81 (m, 2H), 2.05 (s, 3H), 1.28 (t, 3H).

Procedure for Synthesis of 4-chloro-2-hydroxy-3-methyl-2H-furan-5-one (Step 2)

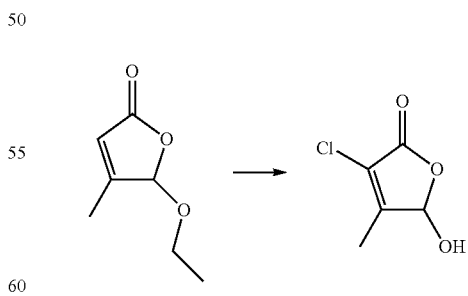

6 g of 2-ethoxy-3-methyl-2H-furan-5-one (42.20 mmol) was dissolved in dichloromethane (150 mL) and cooled to 0° C. To this cooled solution aluminium chloride (0.56 g, 4.2 mmol) was added slowly maintaining the temperature of the reaction mixture to 0° C. Chlorine gas was bubbled into the reaction mixture for 5 h at 0° C. (total weight of the chlorine approximately 12.4 g, 4 eq) and the reaction was brought into room temperature and stirred for 1 h. Excess chlorine gas was removed by bubbling nitrogen in the reaction mixture, filtered through celite bed and the filtrate was evaporated under vacuum. The crude mass was dissolved in ethyl acetate (200 mL) and washed with water (2×75 mL). The organic phase was dried over anhydrous sodium sulphate and concentrated under vacuum. This crude mass (11.5 gm) was then dissolved in tetrahydrofuran (80 mL). Sodium acetate (6.67 gm, 83.3 mmol) was added at 0° C. to this solution and stirred at room temperature for 14 hours. The reaction mixture was then filtered through celite bed and the bed was washed with ethyl acetate (2×50 mL). The filtrate and the washings were mixed and concentrated under vacuum. To this crude mass (6.6 g), 5N HCl (50 mL) was added at 0° C. and stirred at room temperature for 5 h. The reaction mixture was then extracted with ethyl acetate (3×75 mL), the combined organic phase was washed with water (2×25 mL), dried over anhydrous sodium sulphate and concentrated under vacuum to give a crude mass which was purified using silica gel column chromatography to give the desired product (4.64 g 73% yield).

$^1$H NMR (CDCl$_3$): 6.04 (d, 1H), 5.27 (br s, 1H), 2.11 (s, 3H).

Procedure for Synthesis of 1-(5-tert-butylisoxazol-3-yl)-4-chloro-2-hydroxy-3-methyl-2H-pyrrol-5-one (Step 3)

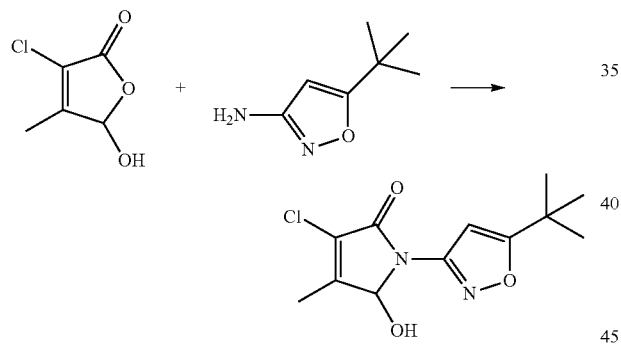

To a stirred solution of 4-chloro-2-hydroxy-3-methyl-2H-furan-5-one (1.0 g, 6.76 mmol) in toluene (8 mL) was added 3-amino-5-tert-butyl-isoxazole (0.95 g, 6.76 mmol) under nitrogen atmosphere. The reaction mixture was refluxed for 5 h. The solvent was then evaporated under vacuum to give a crude mass (2.4 g). To this crude mass, propionic anhydride (2.85 mL, 22.2 mmol) and toluene (5 mL) was added at 0° C. The reaction mixture was warmed to 140° C. and stirred at same temperature for 12 h. The solvent was then evaporated under vacuum and to the residue, acetic acid (10 ml) and water (10 mL) was added. The reaction mixture was heated to 120° C. and stirred at the same temperature for 12 h. The reaction mixture was cooled to room temperature, the solvent was evaporated under vacuum and the mass was diluted with ethyl acetate. (50 mL). The organic phase was washed with water (1×25 mL) and brine (1×25 mL), dried over anhydrous sodium sulphate and concentrated under vacuum to give a crude mass which was purified by using silica gel column chromatography to give the desired solid product A2 (1.31 g, 72% yield).

Example 3

Preparation of 1-(5-tert-butylisoxazol-3-yl)-3-chloro-2-hydroxy-4-methoxy-2H-pyrol-5-one (E1)

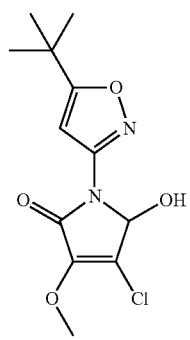 [SMILES: COC1=C(Cl)C(O)N(c2cc(C(C)(C)C)on2)C1=O]

Procedure for Synthesis of 1-(5-tert-butylisoxazol-3-yl)-3-chloro-4-hydroxy-2H-pyrrol-5-one (Step 1)

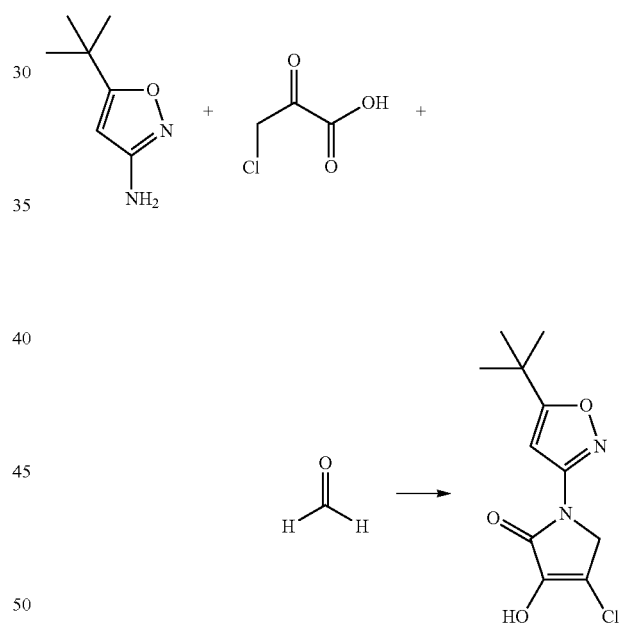

6.86 g (56 mmol) of 3-chloro-2-oxo-propanoic acid was dissolved in 40 ml acetic acid, then 3.925 g (28 mmol) of 5-tert-butylisoxazol-3-amine was added, followed by 2.08 ml (28 mmol) formaldehyde solution (aq) and 2.66 ml conc hydrochloric acid. The mixture was heated to 95° C. for 50 mins, then allowed to cool and left to stand overnight. The reaction was diluted with 40 ml water and any solid was filtered off, washed with water and dried under vacuum to give the desired product as pale beige solid (1.15 g, 16% yield).

1H NMR (CD$_3$CN) 7.60 (br s, 1H), 6.72 (s, 1H), 4.37 (s, 2H), 1.36 (s, 9H).

Procedure for Synthesis of 1-(5-tert-butylisoxazol-3-yl)-3-chloro-4-methoxy-2H-pyrrol-5-one (Step 2)

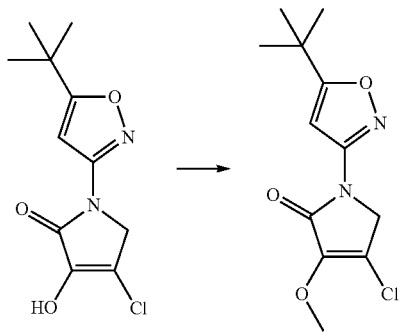 [SMILES: CC(C)(C)c1cc(N2CC(Cl)=C(O)C2=O)no1 ; COC1=C(Cl)CN(c2cc(C(C)(C)C)on2)C1=O]

1 g (4.25 mmol) 1-(5-tert-butylisoxazol-3-yl)-3-chloro-4-hydroxy-2H-pyrrol-5-one was dissolved in 10 ml acetone, then 1.38 g (4.25 mmol) cesium carbonate was added and the resulting mixture was stirred at room temperature for 10 mins. During this time a thick white solid formed. 0.402 ml (4.25 mmol) dimethyl sulfate was added over 5 mins and the resulting mixture stirred at room temp. After 18 hrs the mixture was filtered through celite, the residue was washed with acetone, and the filtrate was concentrated to give 1.13 g (98% yield) of the desired product as a beige solid 1H NMR (CDCl3) 6.72 (s, 1H), 4.38 (s, 2H), 4.17 (s, 3H), 1.35 (s, 9H)

Procedure for Synthesis of [1-(5-tert-butylisoxazol-3-yl)-3-chloro-4-methoxy-5-oxo-2H-pyrrol-2-yl]acetate (E2) (Step 3)

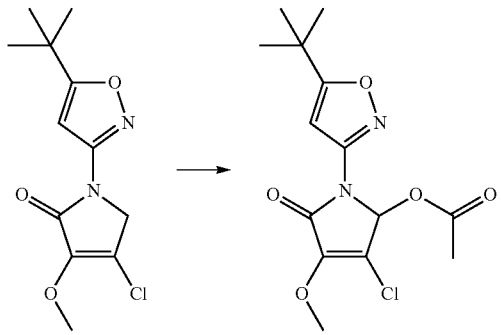 [SMILES: COC1=C(Cl)CN(c2cc(C(C)(C)C)on2)C1=O ; COC1=C(Cl)C(OC(C)=O)N(c2cc(C(C)(C)C)on2)C1=O]

300 mg (1.1 mmol) 1-(5-tert-butylisoxazol-3-yl)-3-chloro-4-methoxy-2H-pyrrol-5-one was dissolved in 3 ml acetic acid and 1.2 ml acetic anhydride, then 891 mg (3.3 mmol) manganese triacetate dihydrate was added and the mixture heated for 1 hour 50 min at 100° C. in the microwave.

10 ml Diethyl ether and 7 ml water were added, shaken, then phases were separated and the aqueous layer was extracted a further two times with 10 ml ether. The combined organic layers were dried over sodium sulfate, filtered and concentrated. Column choratography on silica gel with ethyl acetate/iso-hexane mixture gave 187 mg of the desired product.

1H NMR (CDCl3) 7.13 (s, 1H), 6.65 (s, 1H), 4.22 (s, 3H), 2.20 (s, 3H), 1.34 (s, 9H)

Procedure for Synthesis of 1-(5-tert-butylisoxazol-3-yl)-3-chloro-2-hydroxy-4-methoxy-2H-pyrrol-5-one (Step 4)

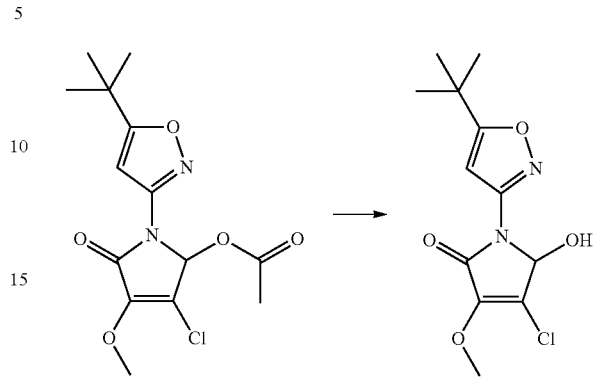

0.745 g (2.27 mmol) [1-(5-tert-butylisoxazol-3-yl)-3-chloro-4-methoxy-5-oxo-2H-pyrrol-2-yl]acetate was dissolved in 7.5 ml dioxane, then 7.5 ml dilute hydrochloric acid (2 molar) was added and the mixture was heated to 100° C. for 70 min in a microwave. The mixture was concentrated in vacuo to give 645 mg of the desired product as white solid.

Example 4

Preparation of 5-tert-butyl-3-(2-hydroxy-4-methoxy-3-methyl-5-oxo-2H-pyrrol-1-yl)isoxazole-4-carbonitrile (D2)

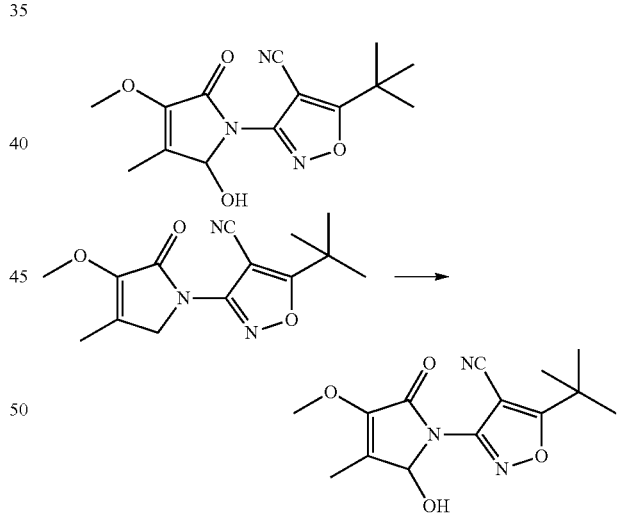

To a solution of 5-tert-butyl-3-(4-methoxy-3-methyl-5-oxo-2H-pyrrol-1-yl)isoxazole-4-carbonitrile (D11) (1 g, 3.632 mmol, this can be prepared as described in example 3, steps 1 and 2 starting from 2-oxo-butyric acid, formaldehyde and 3-amino-5-tert-butyl-isoxazole-4-carbonitrile, which in turn can be prepared as described in example 1, steps 1 to 3 starting from 2,2,-dimethylpropionic acid), in carbon tetrachloride (20 mL/g, 205 mmol) in a 3 neck round bottom flask. To this solution, N-bromo succinimide (NBS) (1.2 equiv., 4.359 mmol) and 2,2'-azobis(2-methylpropionitrile) (0.1 equiv, 0.3632 mmol) was added. The reaction mixture was refluxed for 40 minutes and monitored by thin layer chromatography (TLC) and LC/MS. The reaction was cooled to rt, then filtered. The filtrate was concentrated under reduced pressure and the resulting residue was taken up in water (20 vol) and heated at 75° C. for 30 min. The mixture was cooled to room temperature, then extracted with ethyl acetate thrice, dried over sodium sulfate and concentrated under vacuum to give a crude mass which was then purified by column chromatography (20% ethyl acetate:cyclohexane) to give 0.51 g of the desired product (0.510 g, 1.75 mmol, 48.2% Yield).

Example 5

Preparation of 1-(5-tert-butylisoxazol-3-yl)-2-hydroxy-4-methoxy-3-methyl-2H-pyrrol-5-one (D1)

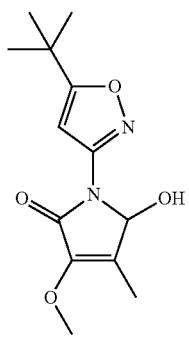 [SMILES: COC1=C(C)C(O)N(c2cc(C(C)(C)C)on2)C1=O]

Procedure for Synthesis of 2-dimethoxyphosphoryl-2-methoxy-acetic acid (Step 1)

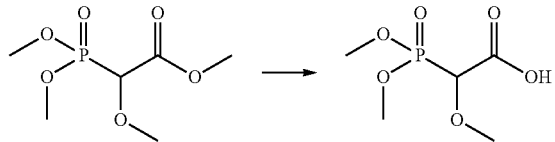

1 g (4.71 mmol) methyl 2-dimethoxyphosphoryl-2-methoxy-acetate was dissolved in MeOH (7.5 ml) and THF (2.5 ml), cooled to 0° C., then 2.59 ml (5.18 mmol) 2N aqueous sodium hydroxide solution, pre cooled, was added all at once. The mixture was stirred at 0° C. After 50 mins, the mixture was acidified with 2.9 ml 2N hydrochloric acid, then concentrated at 100 to 1 mBar at 30° C. 2×20 ml Toluene was added and the mixture concentrated again to give a white gum, which was carried on to the next step without further purification.

NMR (CDCl3, NaCl filtered off) 3.56 (s, 3H), 3.91 (2×s, 6H), 4.30 (d, 1H) 8.35 (br s, 1H)

Procedure for Synthesis of 2-dimethoxyphosphoryl-2-methoxy-acetyl chloride (Step 2)

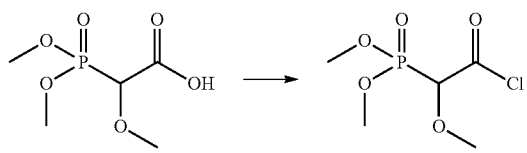

The crude material from step 1 (assumed 4.71 mmol) was dissolved in 15 ml DCM, then 0.036 ml (0.47 mmol) DMF was added, followed by dropwise addition of 0.485 ml (5.65 mmol) oxalyl chloride over 15 mins. The mixture was stirred at rt for 1 hr, then concentrated and reacted as crude material in the next step.

Procedure for Synthesis of N-(5-tert-butylisoxazol-3-yl)-2-dimethoxyphosphoryl-2-methoxy-acetamide (Step 3)

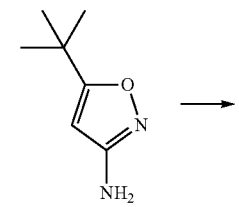

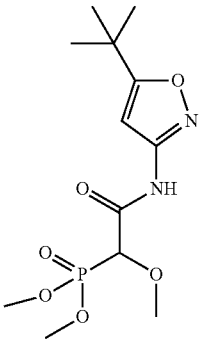

0.66 g (4.71 mmol) 5-tert-butylisoxazol-3-amine was dissolved in 8 ml DCM, then 0.75 ml (5.18 mmol) triethylamine was added and the mixture was cooled to 0° C. The curde acid chloride from step 2 was dissolved in 4 ml dichloromethane and added dropwise over 15 mins. After 1 hr at 0° C., 20 ml water and 20 ml DCM were added, mixtures shaken, and then the layers were separated. The aqueous layer was extracted with further 2×30 ml DCM, and the combined organic fractions were dried over sodium sulfate, filtered and concentrated to give 1.61 g of a crude product, which was not purified further, but reacted in step 4.

NMR (CDCl3) 1.35 (s, 9H), 3.66 (s, 3H), 3.88 (2×s, 6H), 4.20 (d, 1H), 6.71 (s, 1H), 9.06 (br s, 1H)

Procedure for Synthesis of (E)-N-(5-tert-butylisoxazol-3-yl)-2,4,4-trimethoxy-3-methyl-but-2-enamide and (Z)—N-(5-tert-butylisoxazol-3-yl)-2,4,4-trimethoxy-3-methyl-but-2-enamide (Step 4)

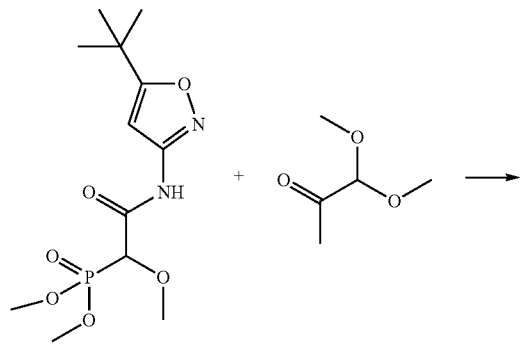

12.6 g (39.3 mmol)N-(5-tert-butylisoxazol-3-yl)-2-dimethoxyphosphoryl-2-methoxy-acetamide was dissolved in 37 ml of dry THF then 41.3 ml (41.3 mmol) lithium hexamethyl disilylamide (1 M in THF) was added dropwise over 10 min to the solution. The reaction exothermed from 20 to 28° C. to give an amber solution. After 2 minutes at 28° C. 5.70 ml (47.2 mmol) of pyruvaldehyde dimethyl acetal was added as a single portion and the mixture was heated to 80° C. for 4 hrs and 45 mins. The mixture was allowed to stand at room temp for 18 hrs and worked up.

100 ml water, 40 ml saturated brine and 160 ml ethyl acetate were added. The aqueous phase was separated and extracted a further ethyl acetate (3×30 ml). The organic layers were dried over sodium sulphate, filtered and concentrated to give 9.83 g of an amber gum. 1H NMR (CDCl3) showed E/Z ratio 2.6 to 1. The crude material was purified on silica gel eluting with ethyl acetate/isohexane mixtures to give 2.944 g of a white solid (24% yield) for the E isomer and 1.50 g of a pale yellow solid (12% yield) for the Z isomer.

Z isomer 1H NMR (CDCl3) 8.86 (br s, 1H), 6.76 (s, 1H), 5.18 (s, 1H), 3.64 (s, 3H), 3.40 (s, 6H), 2.08 (s, 3H), 1.36 (s, 9H)

E isomer 1H NMR (d3 acetonitrile) 9.20 (br s, 1H), 6.64 (s, 1H), 5.67 (s, 1H), 3.59 (s, 3H), 3.32 (s, 6H), 2.14 (s, 3H), 1.34 (s, 9H)

Procedure for Synthesis of 1-(5-tert-butylisoxazol-3-yl)-2-hydroxy-4-methoxy-3-methyl-2H-pyrrol-5-one (Step 5)

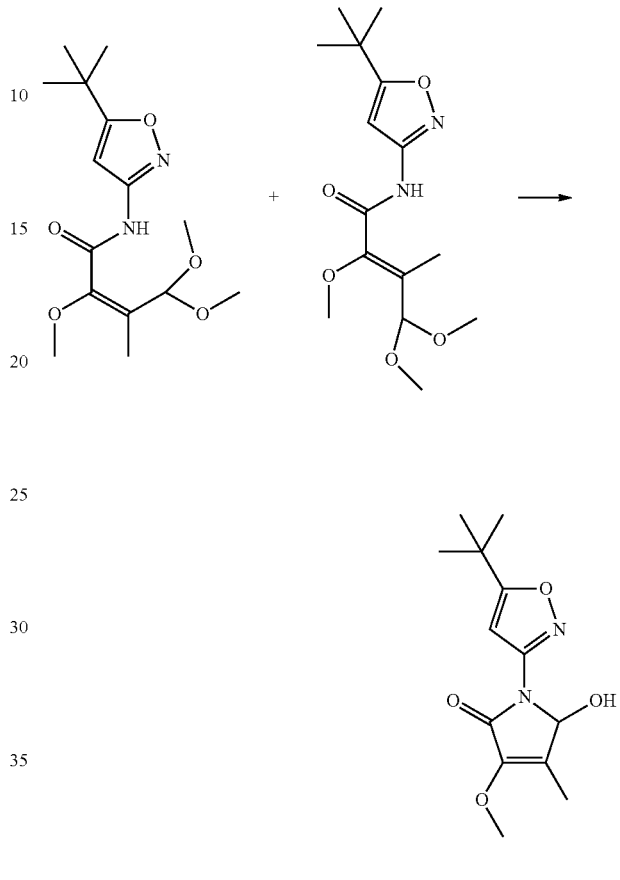

511 mg (1.75 mmol) of N-(5-tert-butylisoxazol-3-yl)-2,4,4-trimethoxy-3-methyl-but-2-enamide (E/Z 74/26, product from step 4) was dissolved in 5 ml acetone then 2 ml water, and 2 ml acetic acid were added and the mixture was stirred at rt. After 10 h at RT the residue was concentrated and purified on silica gel, using ethyl acetate/isohexane mixtures as eluent to afford the desired product (195 mg) as a white solid.

Example 6

Preparation of 1-(4-bromo-5-tert-butyl-isoxazol-3-yl)-4-chloro-2-hydroxy-3-methyl-2H-pyrrol-5-one (A23)

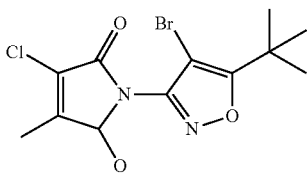 [SMILES: CC1=C(Cl)C(=O)N(c2noc(C(C)(C)C)c2Br)C1O]

Procedure for Synthesis of 4-bromo-5-tert-butyl-isoxazol-3-amine (Step 1)

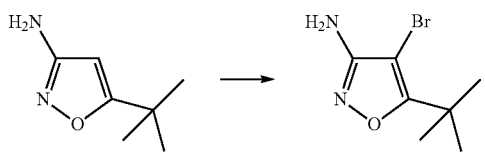

5-tert-butylisoxazol-3-amine (2.0 g, 14.28 mmol) was dissolved in chloroform (40 ml) and cooled to 0° C. N-bromosuccinimide (2.54 g, 14.28 mmol) was added in lots under stirring over a period of 10 min and stirred at this temperature for another 10 min. Reaction mixture was then diluted with chloroform (160 ml), washed with water (50 ml), dried over sodium sulfate and concentrated under vacuum. Crude mass was then purified using silica gel column chromatography to give the desired compound (1.82 g, 58% yield).

$^1$H NMR (CDCl$_3$): 4.10 (br s, 2H), 1.39 (s, 9H)

4-bromo-5-tert-butyl-isoxazol-3-amine can then be further converted to the desired product A23 according to the protocols described in example 1, step 4 and 5.

Example 7

Preparation of 1-(5-tert-butyl-4-fluoro-isoxazol-3-yl)-4-chloro-2-hydroxy-3-methyl-2H-pyrrol-5-one (A19)

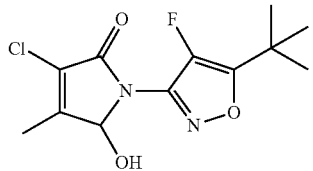 [SMILES: CC1=C(Cl)C(=O)N(c2noc(C(C)(C)C)c2F)C1O]

Procedure for Synthesis of tert butyl N-(5-tert-butyl-isoxazole-3yl)carbamate (Step 1)

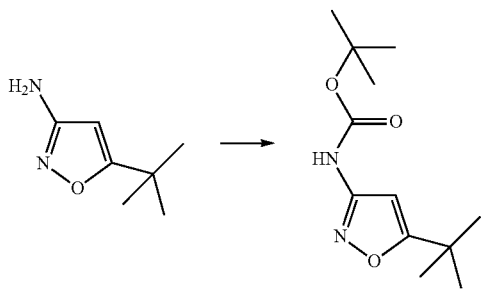

To a solution of 5-tert-butylisoxazol-3-amine (3.0 g, 21.4 mmol) in tetrahydrofuran (30 ml), lithium bis(trimethylsilyl)amide (1 M in THF, 27 ml, 27 mmol) was added and stirred at room temperature for 40 min. To this reaction mixture, solution of ditertiary butyl dicarbonate (5.1 g, 23 mmol) in tetrahydrofuran (20 ml) was added slowly and stirred at room temperature for 3 h. The reaction mixture was quenched with water (40 ml) and extracted with ethyl acetate (150 ml×3). Combined organic layer was dried over sodium sulfate, and concentrated under vacuum. Crude mass obtained was dissolved in methanol (60 ml), 4 N sodium hydroxide solution (60 ml) was added and stirred at room temperature for 2 h. This reaction mixture was then extracted with ethyl acetate (150 ml×3), washed with water, dried over sodium sulfate and concentrated under vacuum. This crude mass was then purified by silica gel column chromatography to give the desired compound (2.77 g, 54% yield).

$^1$H NMR (CDCl$_3$): 7.25 (bs, 1H), 6.47 (s, 1H), 1.51 (s, 9H), 1.32 (s, 9H),

Procedure for Synthesis of tert-butyl-N-(5-tert-butyl-4-fluoro-isoxazole-3yl)carbamate (Step 2)

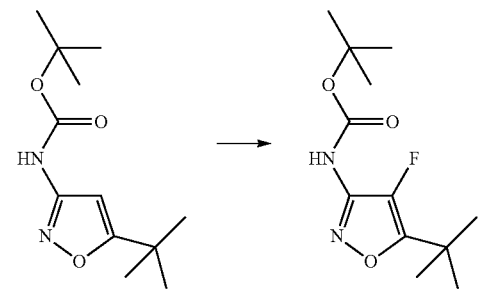 [SMILES: CC(C)(C)OC(=O)Nc1cc(C(C)(C)C)on1 ; CC(C)(C)OC(=O)Nc1noc(C(C)(C)C)c1F]

Tert butyl N-(5-tert-butyl-isoxazole-3yl)carbamate (3 g, 12.5 mmol) was dissolved in tetrahydrofuran (75 ml) and cooled to −78° C. To this solution, n-butyllithium (1.6M in hexane, 17.8 ml, 27.5 mmol) was added at −78° C., warmed to room temperature and stirred for 1 h. The reaction mixture was further cooled to −30° C., followed by addition of N-fluorosuccinimide (5.12 g, 16.25 mmol) in tetrahydrofuran (9 ml). The reaction mixture was warmed to room temperature and stirred for 18 h. Reaction mixture was quenched with aqueous ammonium chloride solution (50 ml) and extracted with ethyl acetate (140 ml×3). Combined organic layer was washed with water (100 ml), dried over sodium sulphate and concentrated under vacuum to give a crude mass (2.5 g, 77.6% yield) which was taken to the next step without purification.

Procedure for Synthesis of 5-tert-butyl-4-fluoro-isoxazole-3-amine (Step 3)

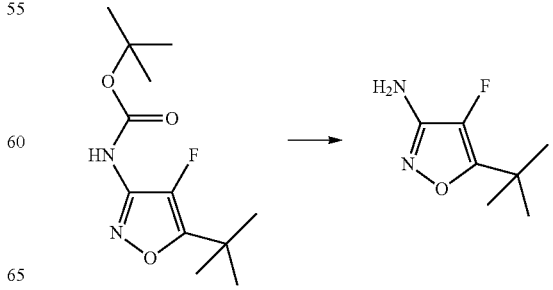

To a solution of tert-butyl-N-(5-tert-butyl-4-fluoro-isoxazole-3yl)carbamate (2.5 g, 12.5 mmol) in dioxane (25 ml), hydrochloric acid (4N, 25 ml)) was added and heated at 55° C. for 2 h. Reaction mixture was adjusted to alkaline pH using sodium bicarbonate solution and extracted with ethyl acetate (150 ml×3). The organic layers were combined, dried over sodium sulfate was concentrated under vacuum to give a crude mass. Crude mass was purified using silica gel column chromatography to give the desired compound (0.75 g, 49% yield).

¹H NMR (CDCl₃): 3.93 (br s, 2H), 1.33 (s, 9H).

5-tert-butyl-4-fluoro-isoxazol-3-amine can then be further converted to the desired product A19 according to the protocols described in example 1, step 4 and 5.

Example 8

Preparation of 1-(5-tert-butyl-4-methyl-isoxazol-3-yl)-4-chloro-2-hydroxy-3-methyl-2H-pyrrol-5-one (A20)

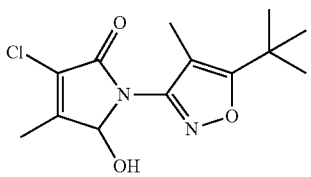 [SMILES: CC1=C(Cl)C(=O)N(c2noc(C(C)(C)C)c2C)C1O]

Procedure for Synthesis of tert-butyl-N-(5-tert-butyl-4-methyl-isoxazole-3yl)carbamate (Step 1)

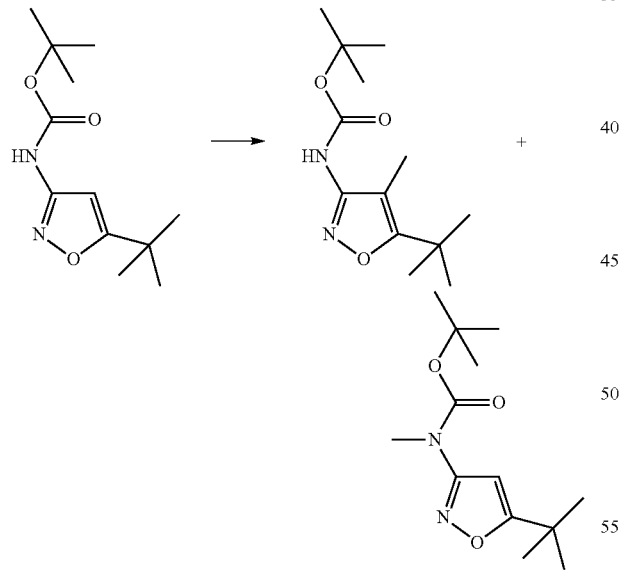

To a solution of tert butyl N-(5-tert-butyl-isoxazole-3yl)carbamate (2 g, 8.33 mmol, this can be prepared as described in example 7, step 1) in tetrahydrofuran (80 ml) at −78° C., n-butyl lithium (1.6 M in hexane, 11.5 ml, 18.33 mmol) was added. The reaction mixture was warmed to room temperature and stirred for 1 h. This reaction mixture was then cooled to 0° C. and a solution of methyl iodide (0.56 ml, 9.16 mmol) in tetrahydrofuran (40 ml) was added and stirred at room temperature for 1 h. The reaction mixture was quenched with water (60 ml) and extracted with ethyl acetate (180 ml×3). The organic layers were combined, dried over sodium sulphate and concentrated under vacuum to give a crude mass (2.1 g) which contained a mixture of two compounds. The crude mass was taken to the next step without further purification.

Procedure for Synthesis of 5-tert-butyl-4-methyl-isoxazole-3-amine

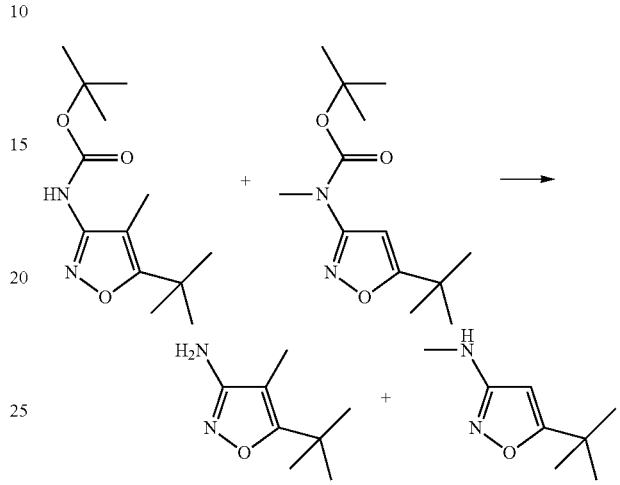

Mixture containing tert-butyl-N-(5-tert-butyl-4-methyl-isoxazole-3yl)carbamate and tert-butyl N-(5-tert-butylisoxazol-3-yl)-N-methyl-carbamate (2.0 g, 7.87 mmol) was dissolved in dioxane (20 ml). To this solution, hydrochloric acid (4N, 20 ml)) was added and heated at 75° C. for 3 h. The reaction mixture was adjusted to alkaline pH using sodium bicarbonate solution and extracted with ethyl acetate (100 ml×3). The organic layers were combined, washed with water (75 ml), dried over sodium sulphate and concentrated under vacuum to give a crude mass. The crude mass was purified using silica gel column chromatography to give the desired 5-tert-butyl-4-methyl-isoxazole-3-amine (0.61 g, 50.4% yield) along with a side product 5-tert-butyl-N-methyl-isoxazole-3-amine (0.60 g, 49.5% yield).

1H NMR (CDCl₃): 3.9 (br s, 2H), 2.3 (s, 3H), 1.39 (s, 9H)

5-tert-butyl-4-methyl-isoxazol-3-amine can then be further converted to the desired product A20 according to the protocols described in example 1, step 4 and 5.

Example 9

Preparation of [1-(5-tert-butyl-4-cyano-isoxazol-3-yl)-4-chloro-3-methyl-5-oxo-2H-pyrrol-2-yl]acetate (A94)

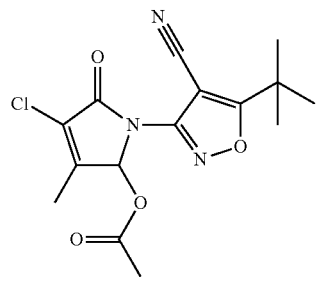

-continued

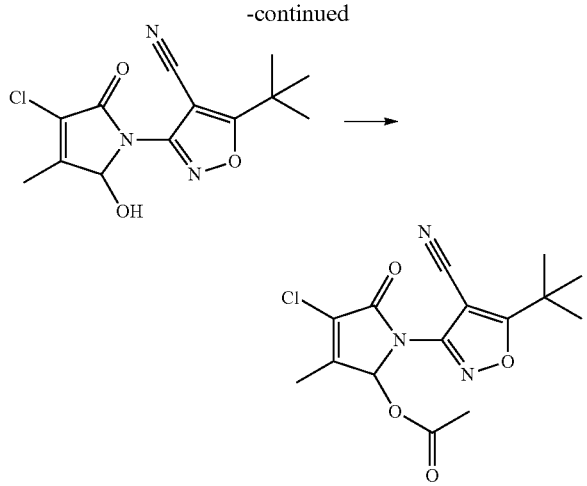

5-tert-butyl-3-(4-chloro-2-hydroxy-3-methyl-5-oxo-2H-pyrrol-1-yl)isoxazole-4-carbonitrile (0.15 g, 0.50 mmol, A31, this can be prepared as described in example 1, steps 1 to 5 starting from 2,2-dimethyl propanoyl chloride) was dissolved in dichloromethane (15 ml) and cooled to 0° C. with stirring. To this reaction mixture, triethylamine (0.15 g, 1.52 mmol) and acetyl chloride (0.059 g, 0.76 mmol) was added and stirred at 0° C. for 3 h. The reaction mixture was then quenched with water and extracted with dichloromethane (50 ml×3 ml). The organic layers were mixed together, washed with water (50 ml), dried over sodium sulphate and concentrated under vacuum to give a crude mass. The crude mass was then purified using silica gel column chromatography to give the desired compound A94 (0.1 g, 58%).

Example 10

Preparation of 5-tert-butyl-3-(2A-dichloro-3-methyl-5-oxo-2H-pyrrol-1-yl)isoxazole-4-carbonitrile (A97)

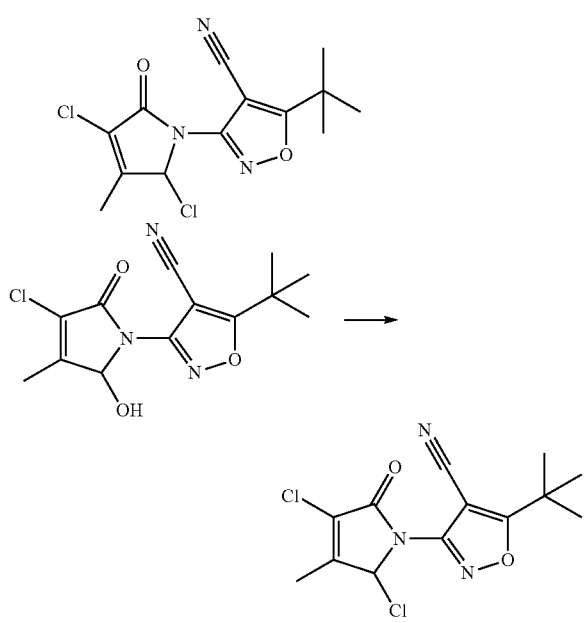

5-tert-butyl-3-(4-chloro-2-hydroxy-3-methyl-5-oxo-2H-pyrrol-1-yl)isoxazole-4-carbonitrile (0.1 g, 0.30 mmol, A31, this can be prepared as described in example 1, steps 1 to 5 starting from 2,2-dimethyl propanoyl chloride) was dissolved in dichloromethane (1 ml) and cooled to 0° C. with stirring. To this solution thionyl chloride (0.1 g, 0.1 mmol) was added and refluxed for 3 h. The reaction mixture was quenched with ice cold water (15 ml) and extracted with dichloromethane (3×25 ml). The organic layer was washed with water, dried over sodium sulphate and concentrated under vacuum to give a crude mass. This crude mass was then purified using silica gel column chromatography to give the desired compound A97 (0.053 g, 50% yield).

Example 11

Preparation of 2-[3-(4-chloro-2-hydroxy-3-methyl-5-oxo-2H-pyrrol-1-yl)isoxazol-5-yl]-2-methyl-propanamide (A67)

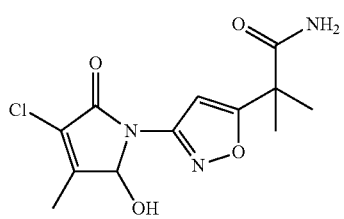 [SMILES: CC1=C(Cl)C(=O)N(c2cc(C(C)(C)C(N)=O)on2)C1O]

Procedure for Synthesis of 2,2-dimethyl-3-oxo-pentanedinitrile (Step 1)

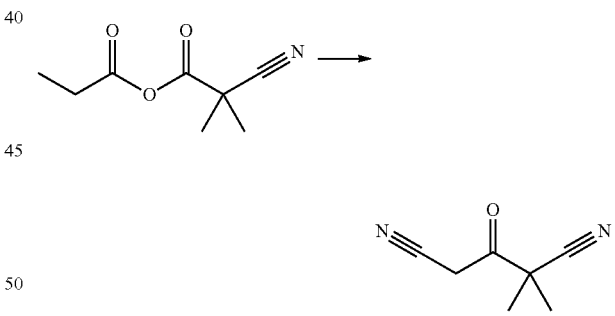

Acetonitrile (5.55 ml, 106.25 mmol) was added drop wise to a solution of n-butyl lithium (1.2 equiv., 85 mmol) in tetrahydrofuran (150 ml) at −10° C. under nitrogen atmosphere. After 1 hour, solution of ethyl 2-cyano-2-methyl-propanoate (10 g, 70.83 mmol) in tetrahydrofuran (20 ml) was added drop wise to the reaction mixture. The reaction mixture was stirred for 3 hours and then acidified with dilute acetic acid. The reaction mixture was extracted with ethyl acetate (100 ml×3), combined organic layers were dried over sodium sulphate and concentrated under vacuum to give a crude mass. The crude mass was purified using silica gel column chromatography to give the desired compound (4.2 g, 44% yield)

$^1$H NMR (CDCl$_3$): 3.98 (s, 2H), 1.59 (s, 6H).

Procedure for Synthesis of 3-chloro-4,4-dimethyl-pent-2-enedinitrile (Step 2)

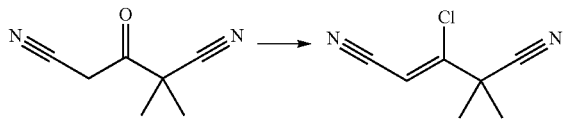

Phosphorous pentachloride (6.86 g, 33 mmol) was added by portion wise to a solution of 2,2-dimethyl-3-oxo-pentanedinitrile (3.5 g, 26 mmol) in dichloromethane (3.5 ml) at 0° C. The temperature of the reaction mixture was allowed to come to room temperature and then heated for 3 hours at 90° C. under nitrogen atmosphere. The reaction mixture was cooled to room temperature and diluted with dichloromethane (50 ml), neutralized with sodium bicarbonate solution and extracted with dichloromethane (3×150 ml). The organic layers were combined, washed with water, dried over sodium sulphate and concentrated under vacuum to give a crude mass (3.6 g, 91%). The crude mass was taken to the next step without further purification.

$^1$H NMR (CDCl$_3$): 6.13 (s, 1H), 1.67 (s, 6H).

Procedure for Synthesis of 2-(3-aminoisoxazol-5-yl)-2-methyl-propanenitrile (Step 3)

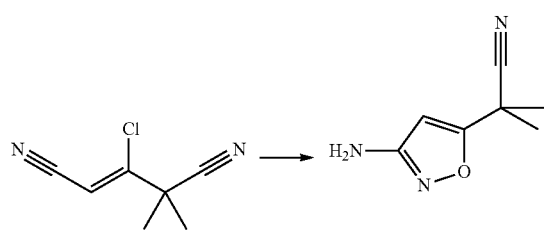

3-chloro-4,4-dimethyl-pent-2-enedinitrile (3.5 g, 23 mmol) in ethanol (11 ml) was added dropwise to a solution of hydroxyl urea (1.9 g, 25 mmol,) and sodium hydroxide (1.1 g, 27 mmol) in water (11 ml) at 0° C. Reaction was stirred for 12 hours at room temperature. The reaction mass was evaporated to a give a residue which was diluted with water (50 ml) and extracted with ethyl acetate (100 ml×3). The organic layers were combined, washed with water, dried over sodium sulphate and concentrated under vacuum to give a crude mass. The crude mass was purified by using silica gel column chromatography to give the desired compound (1.1 g, 32% yield).

$^1$H NMR (CDCl$_3$): 5.91 (s, 1H), 1.72 (s, 6H).

Procedure for Synthesis 2-(3-aminoisoxazol-5-yl)-2-methyl-propanoic acid (Step 4)

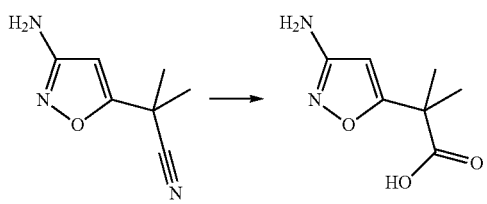

2-(3-aminoisoxazol-5-yl)-2-methyl-propanenitrile (100 mg, 0.66 mmol) was added to a solution of sulfuric acid (2 ml) and water (2 ml) and refluxed for 12 hours. Reaction mixture was cooled and diluted with water (10 ml) and ethyl acetate (3×50 ml). The organic layers were combined, washed with water, dried over sodium sulphate and concentrated under vacuum to give a crude mass. The crude mass was purified by using silica gel column chromatography to give the desired compound (40 mg, 35% yield).

$^1$H NMR (DMSO-d6): 5.66 (s, 1H), 1.41 (s, 6H)

Procedure for Synthesis of 2-[3-(4-chloro-2-hydroxy-3-methyl-5-oxo-2H-pyrrol-1-yl)isoxazol-5-yl]-2-methyl-propanoic acid (Step 5)

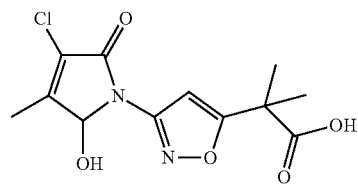 [SMILES: CC1=C(Cl)C(=O)N(c2cc(C(C)(C)C(=O)O)on2)C1O]

2-(3-aminoisoxazol-5-yl)-2-methyl-propanoic acid can then be further converted to the desired product according to the protocols described in example 1, step 4 and 5.

$^1$H NMR (CDCl$_3$): 6.95 (s, 1H), 5.94 (s, 1H), 5.29 (s, 1H), 2.17 (s, 3H), 1.66 (s, 6H).

Procedure for Synthesis of 2-[3-(4-chloro-2-hydroxy-3-methyl-5-oxo-2H-pyrrol-1-yl)isoxazol-5-yl]-2-methyl-propanamide (Step 6)

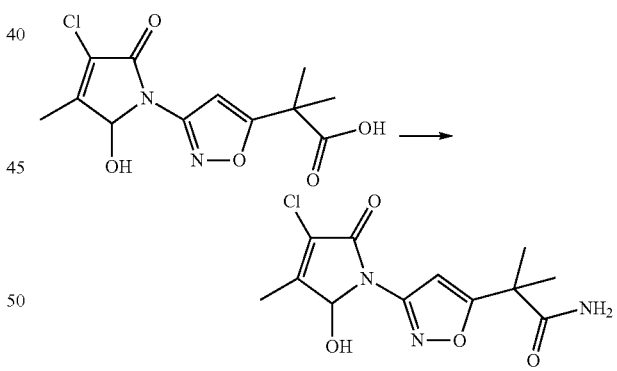

To a solution of 2-[3-(4-chloro-2-hydroxy-3-methyl-5-oxo-2H-pyrrol-1-yl)isoxazol-5-yl]-2-methyl-propanoic acid (50 mg, 0.166 mmol) in dichloromethane (3 ml) was added 1-(3-Dimethylaminopropyl)-3-ethylcarbodiimide hydrochloride (0.095 g, 0.49 mmol) and N,N-diisopropyl ethyl amine (0.08 ml, 0.49 mmol). To this reaction mixture, saturated solution of ammolonia in dioxane (5 ml) was added and stirred for 12 hours at 0° C. The reaction mixture was diluted with water (15 ml) and then extracted with dichloromethane (3×20 ml). The organic layers were combined, washed with water, dried over sodium sulphate and concentrated under vacuum to give the desired compound A67 (40 mg, 80.2% yield).

Example 12

Preparation of 5-tert-butyl-3-(4-chloro-2-hydroxy-3-methyl-5-oxo-2H-pyrrol-1-yl)isoxazole-4-carboxamide (A48)

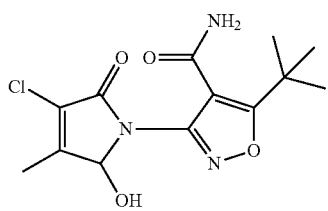 [SMILES: CC1=C(Cl)C(=O)N(c2noc(C(C)(C)C)c2C(N)=O)C1O]

Procedure for Synthesis of 3-amino-5-tert-butyl-isoxazole-4-carboxamide (Step 1)

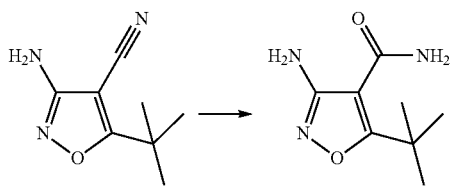

Conc. sulfuric acid (10 mL) was added to 3-amino-5-tert-butyl-isoxazole-4-carbonitrile (1 g, 6.05 mmol, this can be prepared as described in example 1, steps 1 to 3 starting from 2,2,-dimethylpropionic acid) at room temperature and the mixture was refluxed for 2 hours.

The reaction mixture was poured onto water (20 ml) and then extracted with ethyl acetate (3×20 ml). The combined organic layers were dried and concentrated to give 0.8 g (72%) of the desired product.

1H NMR (CDCl3) 7.13 (s, 1H), 6.65 (s, 1H), 4.22 (s, 3H), 2.20 (s, 3H), 1.34 (s, 9H)

3-amino-5-tert-butyl-isoxazole-4-carboxamide can then be further converted to the desired product A48 according to the protocols described in example 1, step 4 and 5.

Example 13

Preparation of 1-(5-tert-butylisoxazol-3-yl)-4-chloro-2-hydroxy-3-(prop-2-ynylamino)-2H-pyrrol-5-one (C5)

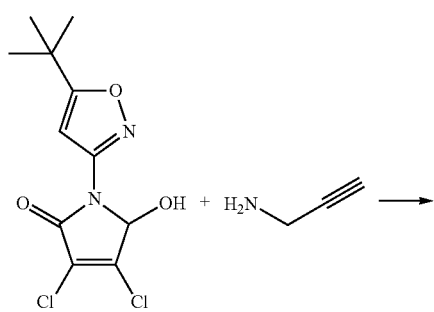

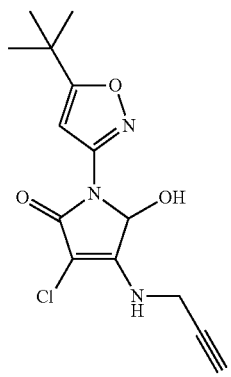

1-(5-tert-butylisoxazol-3-yl)-3,4-dichloro-2-hydroxy-2H-pyrrol-5-one (0.100 g) was dissolved in dichloromethane then the propargyl amine (5 drops, excess) was added. After standing at room temperature for 72 h the crude reaction mixture was purified by flash chromatography, eluting in 0-40% ethyl acetate in hexane. This afforded the desired product as an orange oil (64 mg).

Example 14

Preparation of 3-amino-1-(5-tert-butylisoxazol-3-yl)-4-chloro-2-hydroxy-2H-pyrrol-5-one (C6)

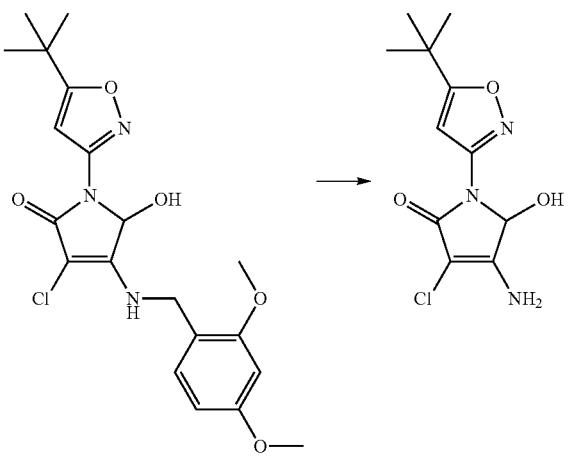 [SMILES: COc1ccc(CNC2=C(Cl)C(=O)N(c3cc(C(C)(C)C)on3)C2O)c(OC)c1 ; CC(C)(C)c1cc(N2C(=O)C(Cl)=C(N)C2O)no1]

1-(5-tert-butylisoxazol-3-yl)-4-chloro-3-[(2,4-dimethoxyphenyl)methylamino]-2-hydroxy-2H-pyrrol-5-one (0.512 g) was dissolved in 1.25M methanolic HCl solution (20 ml) and left to stand at room temperature overnight. The solvent was removed and the crude product was purified by flash chromatography, eluting in 0-70% ethyl acetate in hexane. This afforded the desired product as a white solid (43 mg).

Tables 1-7 lists examples of compounds of the general formula (I)

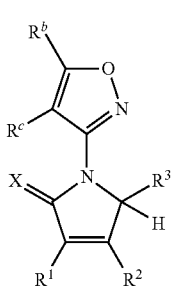
(I)
wherein $R^b$, $R^c$, $R^1$, $R^2$, $R^3$ and X are as defined above.
These compounds were made by the general methods of Examples 1 to 14.
TABLE 1
| entry | STRUCTURE | 1H NMR (measured in CDCl$_3$ unless otherwise indicated) δ | MP ° C. |
|---|---|---|---|
| A1 | 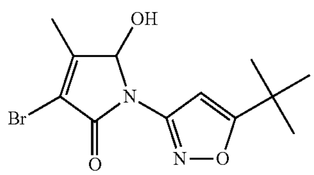 [SMILES: CC1=C(Br)C(=O)N(c2cc(C(C)(C)C)on2)C1O] | 6.73 (s, 1H), 5.97 (s, 1H), 5.08 (s, 1H), 2.18 (s, 3H), 1.37 (s, 9H) | |
| A2 | 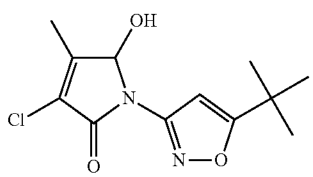 [SMILES: CC1=C(Cl)C(=O)N(c2cc(C(C)(C)C)on2)C1O] | 6.74 (s, 1H), 5.98-5.95 (m, 1H), 5.16-5.10 (m, 1H), 2.18 (s, 3H), 1.37 (s, 9H). | 156-158 |
| A3 | 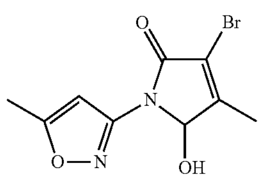 | 6.76 (s, 1H), 5.94 (d, 1H), 4.55 (d, 1H), 2.44 (s, 3H), 2.17 (s, 3H) | |
| A4 | 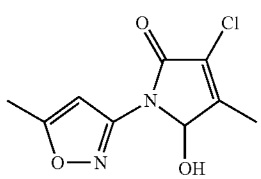 | 6.77 (s, 1H), 5.94 (d, 1H), 4.45 (d, 1H), 2.45 (s, 3H), 2.17 (s, 3H) | |
| A5 | 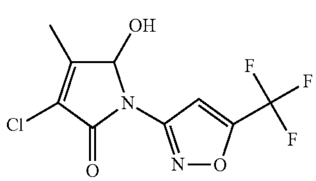 [SMILES: CC1=C(Cl)C(=O)N(c2cc(C(F)(F)F)on2)C1O] | 6.70 (s, 1H); 6.12 (d, 1H); 5.29 (d, 1H); 2.21 (s, 3H) | |
| A6 | 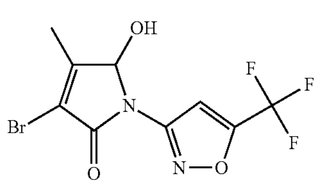 | 6.70 (s, 1H); 6.11 (d, 1H); 4.62 (d, 1H); 2.20 (s, 3H) | |

TABLE 1-continued

| entry | STRUCTURE | 1H NMR (measured in CDCl₃ unless otherwise indicated) δ | MP ° C. |
|---|---|---|---|
| A7 | 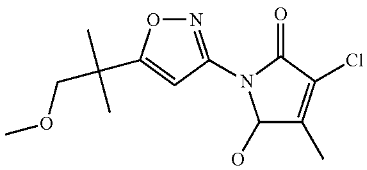 [SMILES: COCC(C)(C)c1cc(N2C(=O)C(Cl)=C(C)C2O)no1] | 6.79 (s, 1H), 5.94 (d, 1H), 4.58 (d, 1H), 3.44 (s, 2H), 3.33 (s, 3H), 2.17 (s, 3H), 1.35 (s, 6H) | |
| A8 | 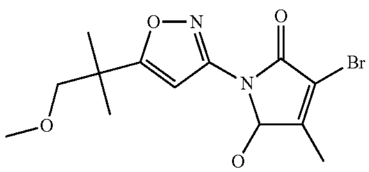 [SMILES: COCC(C)(C)c1cc(N2C(=O)C(Br)=C(C)C2O)no1] | 6.79 (s, 1H), 5.93 (d, 1H), 4.53 (d, 1H), 3.44 (s, 2H), 3.33 (s, 3H), 2.17 (s, 3H), 1.35 (s, 6H) | |
| A9 | Chiral | | |
| A10 | Chiral | | |
| A11 | 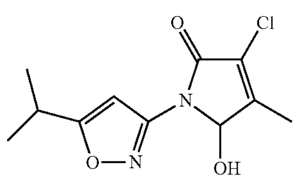 [SMILES: CC1=C(Cl)C(=O)N(c2cc(C(C)C)on2)C1O] | DMSO d6: 7.33 (d, 1H), 6.61 (s, 1H), 5.84 (d, 1H), 3.1 (m, 1H), 2.05 (s, 3H), 1.26 (d, 6H) | 126-128 |
| A12 | 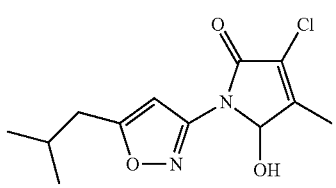 [SMILES: CC1=C(Cl)C(=O)N(c2cc(CC(C)C)on2)C1O] | DMSO-d6: 7.09 (br s, 1H), 6.66 (s, 1H), 5.9 (s, 1H), 2.66 (d, 2H), 2.05 (s, 3H), 1.99 (m, 1H), 0.93 (d, 6H) | 138-140 |
| A13 | 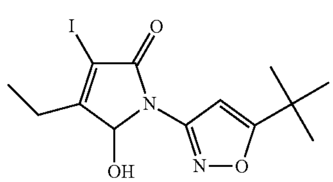 [SMILES: CCC1=C(I)C(=O)N(c2cc(C(C)(C)C)on2)C1O] | 6.75 (s, 1H), 6.1 (d, 1H), 4.98 (d, 1H), 2.61 (m, 2H), 1.35 (s, 9H), 1.23 (t, 3H). | |
| A14 | 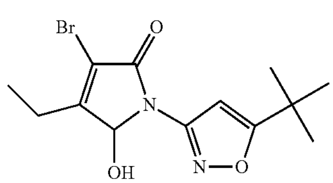 [SMILES: CCC1=C(Br)C(=O)N(c2cc(C(C)(C)C)on2)C1O] | 6.72 (s, 1H), 6.06 (d, 1H), 5.05 (d, 1H), 2.63 (m, 1H), 2.59 (m, 1H), 1.33 (s, 9H), 1.23 (t, 3H). | |

TABLE 1-continued

| entry | STRUCTURE | 1H NMR (measured in CDCl₃ unless otherwise indicated) δ | MP ° C. |
|---|---|---|---|
| A15 | 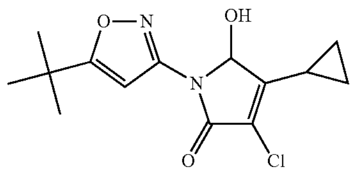 [SMILES: CC(C)(C)c1cc(N2C(=O)C(Cl)=C(C3CC3)C2O)no1] | 6.7 (s, 1H), 5.85 (d, 1H), 4.69 (d, 1H), 2.01 (m, 1H), 1.58 (m, 1H), 1.34 (s, 9H), 1.15 (m, 3H). | |
| A16 | 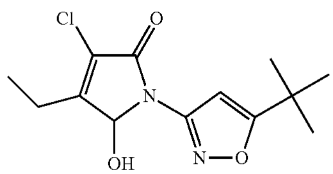 [SMILES: CCC1=C(Cl)C(=O)N(c2cc(C(C)(C)C)on2)C1O] | 6.72 (s, 1H), 6.03 (d, 1H), 4.72 (d, 1H), 2.66 (m, 1H), 2.56 (m, 1H), 1.36 (s, 9H), 1.25 (m, 3H). | |
| A17 | 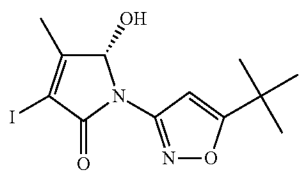 [SMILES: CC1=C(I)C(=O)N(c2cc(C(C)(C)C)on2)[C@H]1O] | 6.74 (s, 1H), 6.01 (d, 1H), 5.3 (d, 1H), 2.2 (s, 3H), 1.36 (s, 9H). | |
| A18 | 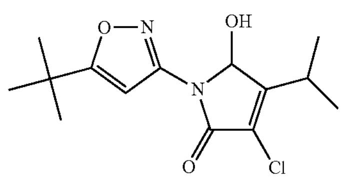 | 6.7 (s, 1H), 6.09 (d, 1H), 4.67 (d, 1H), 3.1 (m, 1H), 1.36 (s, 9H), 1.31 (m, 6H). | |
| A19 | 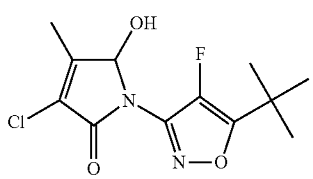 | DMSO-d6: 7.24 (d, 1H), 5.92 (d, 1H), 2.06 (s, 3H), 1.39 (s, 9H) | 98-100 |
| A20 | 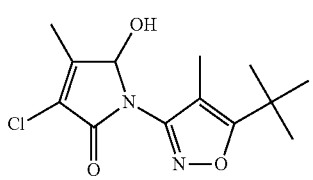 [SMILES: CC1=C(Cl)C(=O)N(c2noc(C(C)(C)C)c2C)C1O] | DMSO-d6: 7.08 (d, 1H), 5.84 (d, 1H), 2.05 (s, 3H), 1.94 (s, 3H), 1.36 (s, 9H) | 134-136 |
| A21 | 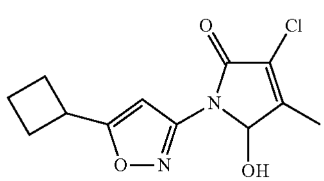 [SMILES: CC1=C(Cl)C(=O)N(c2cc(C3CCC3)on2)C1O] | DMSO d6: 7.15 (d, 1H), 5.89 (d, 1H), 3.68 (m, 1H), 2.35 (m, 2H), 2.22 (m, 2H), 2.05 (s, 3H), 2.0 (m, 1H), 1.9 (m, 1H) | 130-132 |
| A22 | 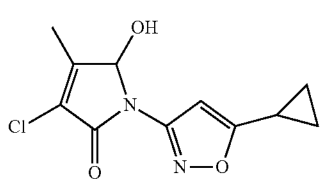 [SMILES: CC1=C(Cl)C(=O)N(c2cc(C3CC3)on2)C1O] | DMSO d6: 7.12 (d, 1H), 6.59 (s, 1H), 5.87 (d, 1H), 2.16 (m, 1H), 2.04 (s, 3H), 1.06 (m, 2H), 0.91 (m, 2H) | 174-176 |

TABLE 1-continued

| entry | STRUCTURE | 1H NMR (measured in CDCl₃ unless otherwise indicated) δ | MP ° C. |
|---|---|---|---|
| A23 | 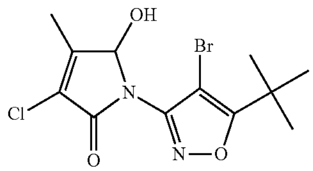 [SMILES: CC1=C(Cl)C(=O)N(c2noc(C(C)(C)C)c2Br)C1O] | DMSO-d6: 7.25 (s, 1H), 5.87 (d, 1H), 2.06 (s, 3H), 1.43 (s, 9H) | 158-160 |
| A24 | 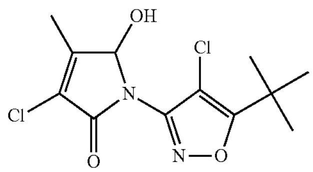 [SMILES: CC1=C(Cl)C(=O)N(c2noc(C(C)(C)C)c2Cl)C1O] | DMSO-d6: 7.26 (d, 1H), 5.91 (d, 1H), 2.063 (s, 3H), 1.4 (s, 9H) | 143-145 |
| A25 | 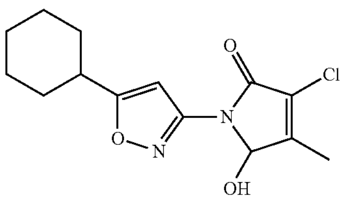 [SMILES: CC1=C(Cl)C(=O)N(c2cc(C3CCCCC3)on2)C1O] | DMSO d6: 7.13 (d, 1H), 6.60 (s, 1H), 5.88 (d, 1H), 2.81 (m, 1H), 2.05 (s, 3H), 1.9 (m, 2H), 1.72 (m, 2H), 1.38 (m, 6H) | 141-143 |
| A26 | 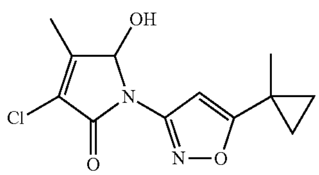 [SMILES: CC1=C(Cl)C(=O)N(c2cc(C3(C)CC3)on2)C1O] | DMSO d6: 7.12 (d, 1H), 6.59 (s, 1H), 5.88 (d, 1H), 2.04 (s, 3H), 1.43 (s, 3H), 1.12 (m, 2H), 0.92 (m, 2H) | 177-178 |
| A27 | 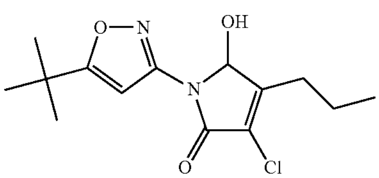 [SMILES: CCCC1=C(Cl)C(=O)N(c2cc(C(C)(C)C)on2)C1O] | 6.73 (s, 1H), 6.02 (s, 1H), 5.05 (m, 1H), 2.58 (m, 2H), 1.7 (m, 2H), 1.37 (s, 9H), 1.01 (m, 3H). | |
| A28 | 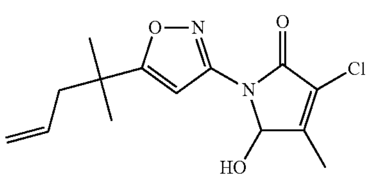 [SMILES: C=CCC(C)(C)c1cc(N2C(=O)C(Cl)=C(C)C2O)no1] | DMSO-d6: 7.12 (d, 1H), 6.617 (s, 1H), 5.9 (d, 1H), 5.63 (m, 1H), 5.06 (d, 1H), 5.03 (s, 1H), 2.37 (d, 2H), 2.05 (s, 3H), 1.28 (s, 6H) | 107-109 |
| A29 | 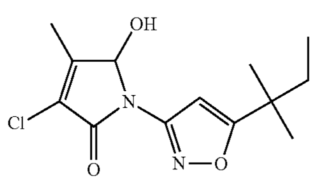 [SMILES: CCC(C)(C)c1cc(N2C(=O)C(Cl)=C(C)C2O)no1] | DMSO-d6: 7.03 (d, 1H), 6.5 (s, 1H), 5.8 (d, 1H), 1.94 (s, 3H), 1.53 (m, 2H), 1.16 (s, 6H), 0.64 (t, 3H) | 103-105 |
| A30 | 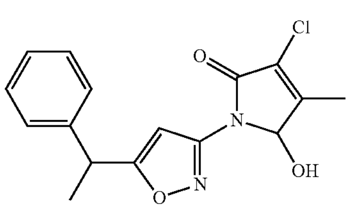 [SMILES: CC1=C(Cl)C(=O)N(c2cc(C(C)c3ccccc3)on2)C1O] | DMSO-d6: 7.35 (m, 5H), 7.14 (m, 1H), 6.77 (d, 1H), 5.88 (d, 1H), 4.37 (m, 1H), 2.04 (s, 3H), 1.6 (d, 3H) | 118-120 |

TABLE 1-continued

| entry | STRUCTURE | 1H NMR (measured in CDCl₃ unless otherwise indicated) δ | MP ° C. |
|---|---|---|---|
| A31 | 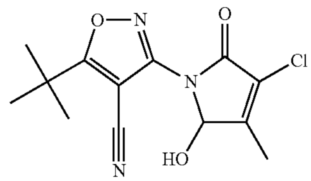 [SMILES: CC1=C(Cl)C(=O)N(c2noc(C(C)(C)C)c2C#N)C1O] | DMSO-d6: 7.34 (d, 1H), 6.02 (d, 1H), 2.08 (s, 3H), 1.46 (s 9H) | 174-176 |
| A32 | 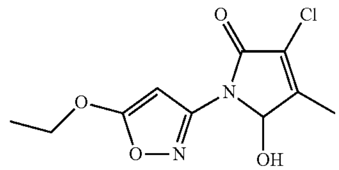 [SMILES: CCOc1cc(N2C(=O)C(Cl)=C(C)C2O)no1] | 5.98 (s, 1H), 4.53 (d, 1H), 4.35-4.26 (m, 2H, OCH2CH3), 1.96 (s, 3H), 1.51-1.45 (m, 3H) | |
| A33 | 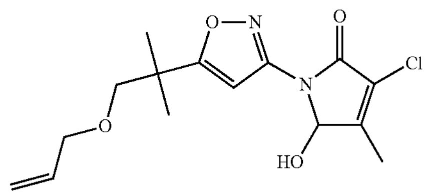 [SMILES: C=CCOCC(C)(C)c1cc(N2C(=O)C(Cl)=C(C)C2O)no1] | DMSO-d6: 7.1 (d, 1H), 6.6 (s, 1H), 5.86 (d, 1H), 5.81 (m, 1H), 5.11 (m, 2H), 3.89 (d, 2H), 3.43 (s, 2H), 2.015 (s, 3H), 1.258 (s, 6H) | 66-68 |
| A34 | 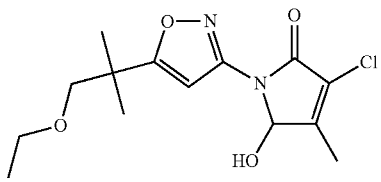 [SMILES: CCOCC(C)(C)c1cc(N2C(=O)C(Cl)=C(C)C2O)no1] | DMSO-d6: 7.09 (d, 1H), 6.604 (s, 1H), 5.86 (d, 1H), 3.37 (m, 4H), 2.01 (s, 3H), 1.24 (s, 6H), 1.03 (t, 3H) | 99-101 |
| A35 | 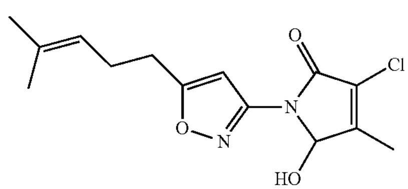 [SMILES: CC(C)=CCCc1cc(N2C(=O)C(Cl)=C(C)C2O)no1] | 6.75 (s, 1H), 5.93 (s, 1H), 5.1 (m, 1H), 4.7 (br, 1H), 2.75 (m, 2H), 2.38 (m, 2H), 2.16 (s, 3H), 1.69 (s, 3H), 1.60 (s, 3H) | 72-74 |
| A36 | 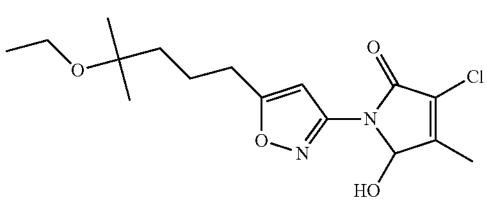 [SMILES: CCOC(C)(C)CCCc1cc(N2C(=O)C(Cl)=C(C)C2O)no1] | 6.69 (s, 1H), 5.86 (s, 1H), 4.46 (br s, 1H), 3.27 (m, 2H), 2.67 (t, 2H), 2.09 (s, 3H), 1.69 (m, 2H), 1.45 (m, 2H), 1.09 (m, 9H) | 110-112 |
| A37 | 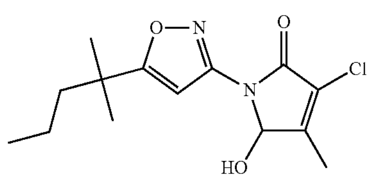 [SMILES: CCCC(C)(C)c1cc(N2C(=O)C(Cl)=C(C)C2O)no1] | 6.61 (s, 1H), 5.88 (s, 1H), 2.09 (s, 3H), 1.51 (m, 2H), 1.24 (s, 6H), 1.11 (m, 2H), 0.79 (t, 3H) | 96-98 |
| A38 | 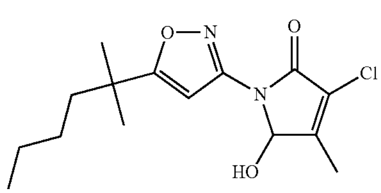 [SMILES: CCCCC(C)(C)c1cc(N2C(=O)C(Cl)=C(C)C2O)no1] | 6.71 (s, 1H), 5.95 (s, 1H), 5.03 (br 1H), 2.16 (s, 3H), 1.64 (m, 2H), 1.31 (s, 6H), 1.27 (m, 2H), 1.13 (m, 2H), 0.85 (t, 3H) | 75-77 |

TABLE 1-continued

| entry | STRUCTURE | 1H NMR (measured in CDCl₃ unless otherwise indicated) δ | MP ° C. |
|---|---|---|---|
| A39 | 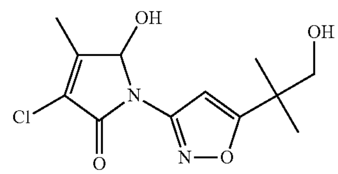 [SMILES: CC1=C(Cl)C(=O)N(c2cc(C(C)(C)CO)on2)C1O] | 6.82 (s, 1H), 5.9 (s, 1H), 3.69 (s, 2H), 2.16 (s, 3H), 1.35 (s, 6H) | 130-132 |
| A40 | 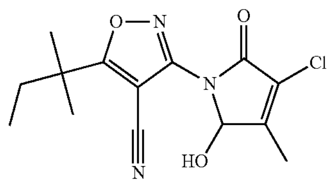 [SMILES: CCC(C)(C)c1onc(N2C(=O)C(Cl)=C(C)C2O)c1C#N] | 5.99 (s, 1H), 4.16 (br s, 1H), 2.18 (s, 3H), 1.86 (m, 2H), 1.48 (s, 6H), 0.86 (t, 3H) | 166-168 |
| A41 | 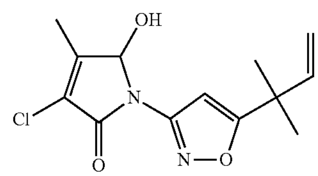 [SMILES: C=CC(C)(C)c1cc(N2C(=O)C(Cl)=C(C)C2O)no1] | 6.75 (s, 1H), 6.0 (m, 1H), 5.93 (s, 1H), 5.1 (m, 2H), 4.59 (br s, 1H), 2.16 (s, 3H), 1.45 (s, 6H) | 114-116 |
| A42 | 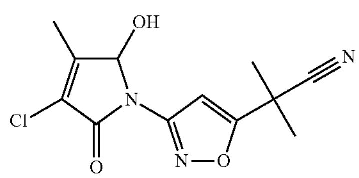 [SMILES: CC1=C(Cl)C(=O)N(c2cc(C(C)(C)C#N)on2)C1O] | 7.05 (s, 1H), 5.95 (s, 1H), 4.42 (s, 1H), 2.18 (s, 3H), 1.8 (s, 6H) | 145-147 |
| A43 | 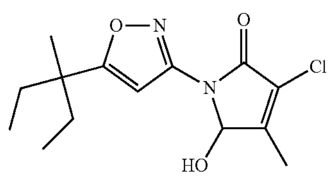 [SMILES: CCC(C)(CC)c1cc(N2C(=O)C(Cl)=C(C)C2O)no1] | 6.73 (s, 1H), 5.93 (d, 1H), 4.53 (d, 1H), 2.16 (s, 3H), 1.76 (m, 2H), 1.63 (m, 2H), 1.26 (s, 3H), 0.78 (m, 6H) | 104-106 |
| A44 | 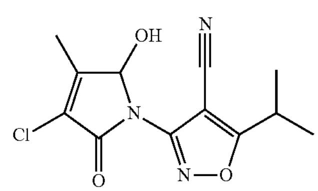 [SMILES: CC1=C(Cl)C(=O)N(c2noc(C(C)C)c2C#N)C1O] | 6.01 (s, 1H), 4.1 (br s, 1H), 3.46 (m, 1H), 2.2 (s, 3H), 1.47 (d, 6H) | 117-119 |
| A45 | 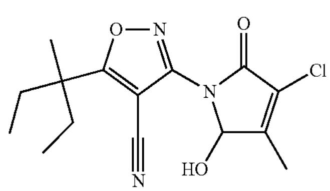 [SMILES: CCC(C)(CC)c1onc(N2C(=O)C(Cl)=C(C)C2O)c1C#N] | 5.98 (s, 1H), 4.0 (br s, 1H), 2.18 (s, 3H), 2.05 (m, 2H), 1.75 (m, 2H), 1.42 (s, 3H), 0.85 (t, 6H) | 129-130 |
| A46 | 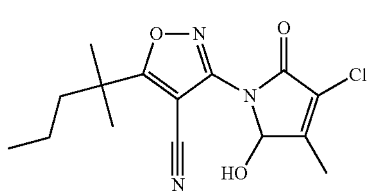 [SMILES: CCCC(C)(C)c1onc(N2C(=O)C(Cl)=C(C)C2O)c1C#N] | DMSO-d6: 7.32 (s, 1 H), 5.97 (s, 1H), 2.04 (s, 3H), 1.70 (m, 2H), 1.4 (s, 6H), 1.15 (m, 2H), 0.82 (t, 3H) | 113-115 |

TABLE 1-continued

| entry | STRUCTURE | 1H NMR (measured in CDCl₃ unless otherwise indicated) δ | MP ° C. |
|---|---|---|---|
| A47 | 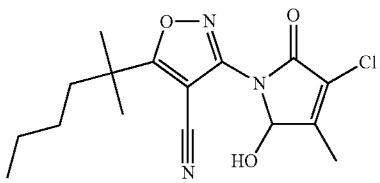 [SMILES: CCCCC(C)(C)c1onc(N2C(=O)C(Cl)=C(C)C2O)c1C#N] | 6.01 (s, 1 H), 2.15 (s, 3H), 1.75 (m, 2H), 1.44 (s, 6H), 1.26 (m, 2H), 1.15 (m, 2H), 0.85 (t, 3H) | 99-101 |
| A49 | 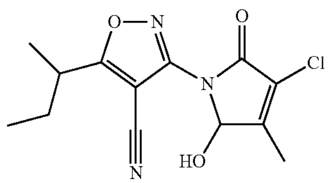 [SMILES: CCC(C)c1onc(N2C(=O)C(Cl)=C(C)C2O)c1C#N] | DMSO-d6: 7.34 (d, 1H), 6.02 (d, 2H), 3.24 (m, 1H), 2.07 (s, 3H), 1.74 (m, 2H), 1.35 (d, 3H), 0.88 (t, 3H) | 107-109 |
| A50 | 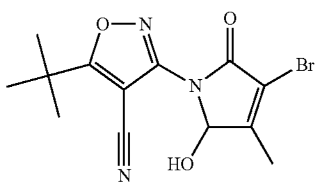 [SMILES: CC1=C(Br)C(=O)N(c2noc(C(C)(C)C)c2C#N)C1O] | 5.92 (s, 1H), 2.11 (s, 3H), 1.45 (s, 9H) | 182-184 |
| A51 | 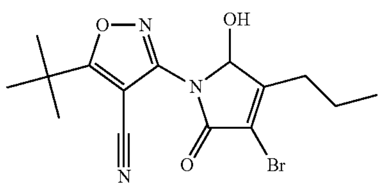 [SMILES: CCCC1=C(Br)C(=O)N(c2noc(C(C)(C)C)c2C#N)C1O] | 6.04 (d, 1H), 4.0 (d, 1H), 2.55 (m, 2H), 1.7 (m, 2H), 1.51 (s, 9H), 1.03 (t, 3H) | 123-124 |
| A52 | 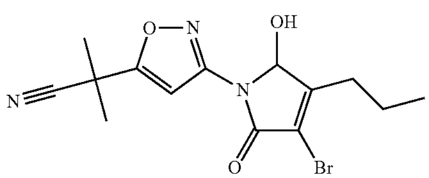 [SMILES: CCCC1=C(Br)C(=O)N(c2cc(C(C)(C)C#N)on2)C1O] | 7.05 (s, 1H), 6.01 (s, 1H), 4.26 (br s, 1H), 2.56 (m, 2H), 1.80 (s, 6H), 1.63 (m, 2H), 1.02 (t, 3H) | 80-82 |
| A53 | 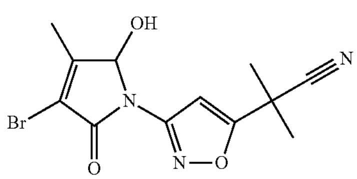 | 7.04 (s, 1H), 5.95 (s, 1H), 2.17 (s, 3H), 1.8 (s, 6H) | 138-140 |
| A54 | 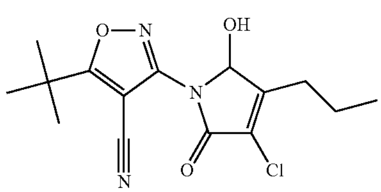 [SMILES: CCCC1=C(Cl)C(=O)N(c2noc(C(C)(C)C)c2C#N)C1O] | 6.04 (s, 1H), 3.88 (br s, 1H) 2.56 (m, 2H), 1.71 (m, 2H), 1.50 (s, 9H), 1.02 (t, 3H) | 133-135 |
| A55 | 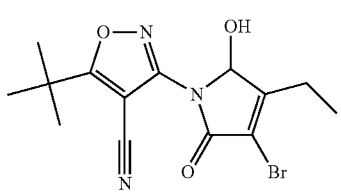 [SMILES: CCC1=C(Br)C(=O)N(c2noc(C(C)(C)C)c2C#N)C1O] | 6.07 (d, 1H), 3.82 (d, 1H), 2.62 (m, 2H), 1.52 (s, 9H), 1.24 (t, 3H) | 138-140 |

TABLE 1-continued

| entry | STRUCTURE | 1H NMR (measured in CDCl₃ unless otherwise indicated) δ | MP ° C. |
|---|---|---|---|
| A56 | Chiral | | |
| A57 | Chiral | | |
| A58 | 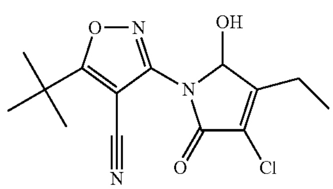 [SMILES: CCC1=C(Cl)C(=O)N(c2noc(C(C)(C)C)c2C#N)C1O] | 6.07 (d, 1H), 3.95 (d, 1H), 2.67 (m, 1H), 2.55 (m, 1H), 1.51 (s, 9H), 1.26 (t, 3H) | 134-136 |
| A59 | 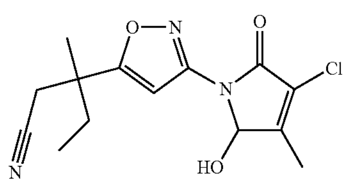 [SMILES: CCC(C)(CC#N)c1cc(N2C(=O)C(Cl)=C(C)C2O)no1] | 6.87 (s, 1H), 5.93 (s, 1H), 4.77 (br s, 1H), 2.72 (m, 2H), 2.16 (s, 3H), 1.85 (m, 2H), 1.5 (s, 3H), 0.84 (m, 3H) | |
| A60 | 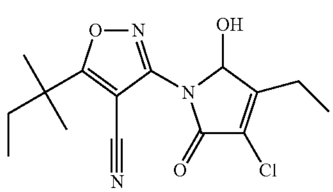 [SMILES: CCC1=C(Cl)C(=O)N(c2noc(C(C)(C)CC)c2C#N)C1O] | 5.97 (s, 1H), 4.11 (br, 1H), 2.44 (m, 2H), 1.85 (m, 2H), 1.47 (s, 6H), 1.16 (t, 3H), 0.85 (t, 3H) | 110-112 |
| A61 | 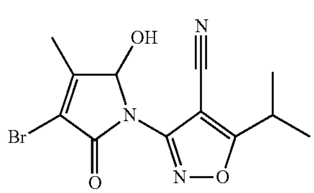 [SMILES: CC1=C(Br)C(=O)N(c2noc(C(C)C)c2C#N)C1O] | 5.99 (s, 1H), 4.54 (br s, 1H), 3.37 (m, 1H), 2.16 (s, 3H), 1.42 (d, 6H) | 127-129 |
| A62 | 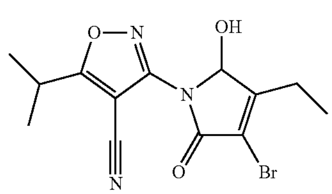 [SMILES: CCC1=C(Br)C(=O)N(c2noc(C(C)C)c2C#N)C1O] | 6.01 (s, 1H), 3.42 (m, 1H), 2.6 (m, 2H), 1.44 (d, 6H), 1.25 (t, 3H) | 106-108 |

TABLE 1-continued

| entry | STRUCTURE | 1H NMR (measured in CDCl₃ unless otherwise indicated) δ | MP ° C. |
|---|---|---|---|
| A63 | 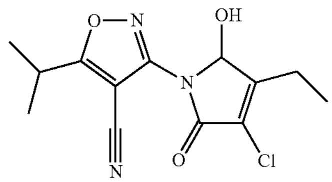 [SMILES: CCC1=C(Cl)C(=O)N(c2noc(C(C)C)c2C#N)C1O] | 6.08 (d, 1H), 4.13 (br, 1H), 3.39 (m, 1H), 2.68 (m, 1H), 2.56 (m, 1H), 1.44 (d, 6H), 1.25 (t, 3H) | 93-95 |
| A64 | 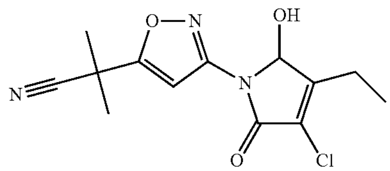 [SMILES: CCC1=C(Cl)C(=O)N(c2cc(C(C)(C)C#N)on2)C1O] | 6.05 (d, 1H), 4.26 (br, 1H), 2.68 (m, 1H), 2.57 (m, 1H), 1.8 (s, 6H), 1.25 (t, 3H) | 101-102 |
| A65 | 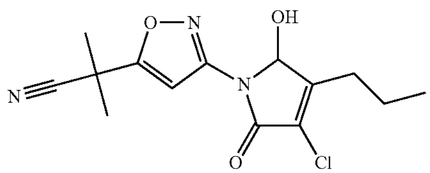 [SMILES: CCCC1=C(Cl)C(=O)N(c2cc(C(C)(C)C#N)on2)C1O] | 7.05 (s, 1H), 6.02 (d, 1H), 4.46 (br s, 1H), 2.56 (m, 2H), 1.78 (s, 6H), 1.7 (m, 2H), 1.01 (t, 3H) | 99-100 |
| A66 | 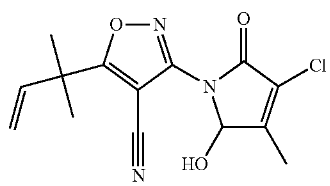 [SMILES: C=CC(C)(C)c1onc(N2C(=O)C(Cl)=C(C)C2O)c1C#N] | 6.02 (m, 2H), 5.24 (m, 2H), 4.14 (d, 1H), 2.17 (s, 3H) 1.6 (s, 6H). | 150-152 |
| A67 | 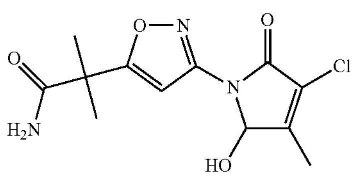 [SMILES: CC1=C(Cl)C(=O)N(c2cc(C(C)(C)C(N)=O)on2)C1O] | MeOD: 6.86 (s, 1H), 5.91 (s, 1H), 2.13 (s, 3H), 1.59 (s, 6H) | 169-171 |
| A68 | 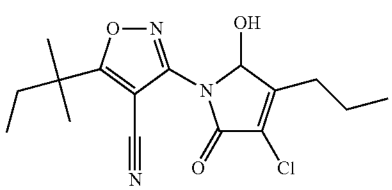 [SMILES: CCCC1=C(Cl)C(=O)N(c2noc(C(C)(C)CC)c2C#N)C1O] | 6.04 (d, 1H), 3.75 (br, 1H), 2.55 (m, 2H), 1.87 (m, 2H), 1.7 (m, 2H), 1.49 (s, 6H), 1.02 (t, 3H), 0.86 (t, 3H) | 82-84 |
| A69 | 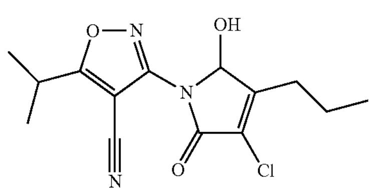 [SMILES: CCCC1=C(Cl)C(=O)N(c2noc(C(C)C)c2C#N)C1O] | 5.97 (d, 1H), 4.1 (br s, 1H), 3.4 (m, 1H), 2.4 (m, 2H), 1.62 (m, 2H), 1.43 (d, 6H), 0.96 (t, 3H) | |
| A70 | 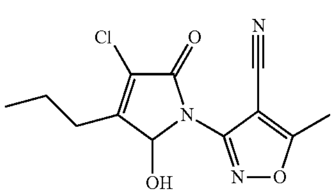 [SMILES: CCCC1=C(Cl)C(=O)N(c2noc(C)c2C#N)C1O] | 5.9 (d, 1H), 4.33 (d, 1H), 2.65 (s, 3H), 2.40 (m, 2H), 1.63 (m, 2H), 0.98 (t, 3H) | |

TABLE 1-continued

| entry | STRUCTURE | 1H NMR (measured in CDCl$_3$ unless otherwise indicated) δ | MP ° C. |
|---|---|---|---|
| A71 | 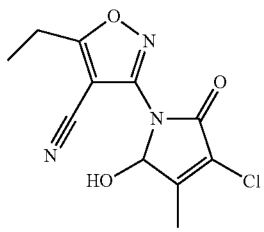 [SMILES: CCc1onc(N2C(=O)C(Cl)=C(C)C2O)c1C#N] | 5.98 (d, 1H), 4.26 (d, 1H), 3.01 (m, 2H), 2.18 (s, 3H), 1.38 (t, 3H) | 95-97 |
| A72 | 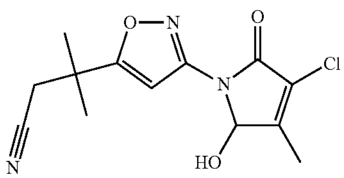 [SMILES: CC1=C(Cl)C(=O)N(c2cc(C(C)(C)CC#N)on2)C1O] | 6.89 (s, 1H), 5.93 (d, 1H), 4.39 (d, 1H), 2.72 (s, 2H), 2.17 (s, 3H), 1.54 (s, 6H) | 103-105 |
| A73 | 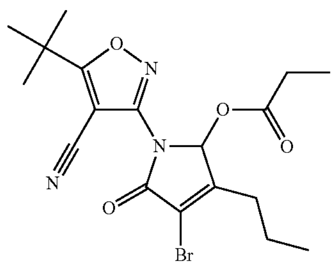 [SMILES: CCCC1=C(Br)C(=O)N(c2noc(C(C)(C)C)c2C#N)C1OC(=O)CC] | 7.19 (s, 1H), 2.53 (m, 1H), 2.43 (m, 2H), 2.29 (m, 1H), 1.6 (m, 2H), 1.5 (s, 9H), 1.15 (t, 3H), 1.0 (t, 3H) | 78-80 |
| A74 | 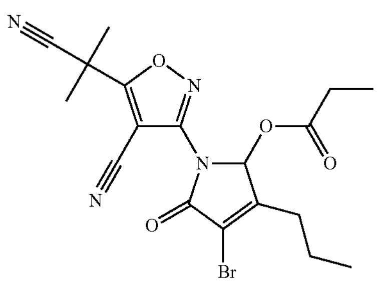 [SMILES: CCCC1=C(Br)C(=O)N(c2noc(C(C)(C)C#N)c2C#N)C1OC(=O)CC] | 7.23 (s, 1H), 7.05 (s, 1H), 2.45 (m, 3H), 2.29 (m, 1H), 1.8 (s, 6H), 1.65 (m, 2H), 1.2 (t, 3H), 1.0 (t, 3H) | |
| A75 | 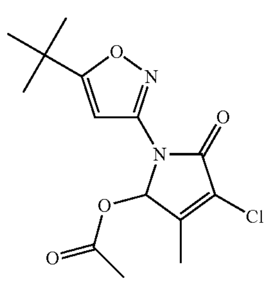 [SMILES: CC(=O)OC1C(C)=C(Cl)C(=O)N1c1cc(C(C)(C)C)on1] | 7.14 (s, 1H), 6.70 (s, 1H), 2.19 (s, 3H), 2.08 (s, 3H), 1.34 (s, 9H) | |
| A76 | 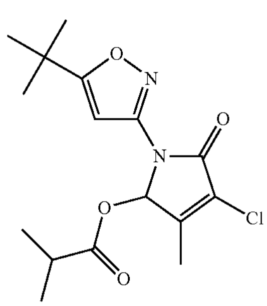 [SMILES: CC1=C(Cl)C(=O)N(c2cc(C(C)(C)C)on2)C1OC(=O)C(C)C] | 7.17 (s, 1H), 6.69 (s, 1H), 2.60 (m, 1H), 2.06 (s, 3H), 1.34 (s, 9H), 1.21 (s, 9H) | |

TABLE 1-continued

| entry | STRUCTURE | 1H NMR (measured in CDCl₃ unless otherwise indicated) δ | MP ° C. |
|---|---|---|---|
| A77 | 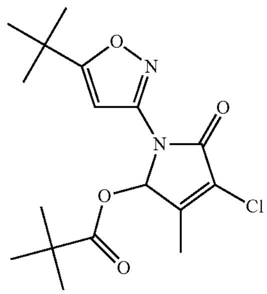 [SMILES: CC1=C(Cl)C(=O)N(c2cc(C(C)(C)C)on2)C1OC(=O)C(C)(C)C] | 7.19 (s, 1H), 6.68 (s, 1H), 3.06-2.90 (m, 2H), 2.12 (s, 3H), 1.39-1.33 (m, 12H) | |
| A78 | 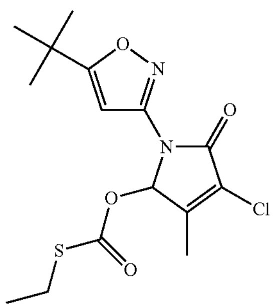 [SMILES: CCSC(=O)OC1C(C)=C(Cl)C(=O)N1c1cc(C(C)(C)C)on1] | 7.19 (s, 1H), 6.68 (s, 1H), 3.06-2.90 (m, 2H), 2.12 (s, 3H), 1.39-1.33 (m, 12H) | |
| A80 | 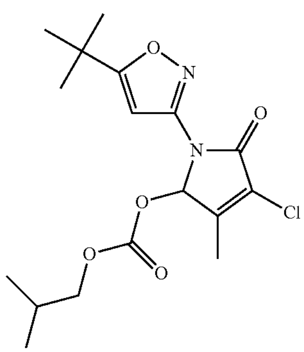 [SMILES: CC1=C(Cl)C(=O)N(c2cc(C(C)(C)C)on2)C1OC(=O)OCC(C)C] | 6.98 (s, 1H), 6.68 (s, 1H), 4.10 (m, 2H), 2.14 (s, 3H), 2.05 (m, 1H), 1.34 (s, 9H), 0.96 (d, 6H), | 84-88 |
| A81 | 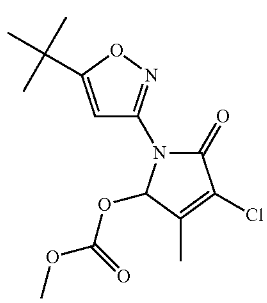 [SMILES: COC(=O)OC1C(C)=C(Cl)C(=O)N1c1cc(C(C)(C)C)on1] | 6.99 (s, 1H), 6.69 (s, 1H), 3.94 (s, 3H), 2.13 (s, 3H), 1.34 (s, 9H) | |

TABLE 1-continued

| entry | STRUCTURE | 1H NMR (measured in CDCl₃ unless otherwise indicated) δ | MP ° C. |
|---|---|---|---|
| A82 | 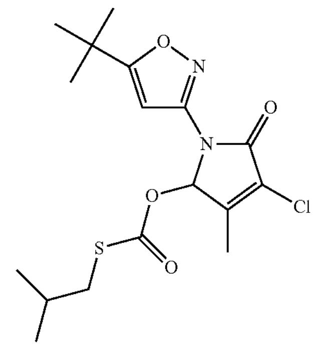 [SMILES: CC1=C(Cl)C(=O)N(c2cc(C(C)(C)C)on2)C1OC(=O)SCC(C)C] | 7.19 (s, 1H), 6.68 (s, 1H), 2.95-2.82 (m, 2H), 2.11 (s, 3H), 1.99-1.89 (m, 1H), 1.36 (s, 9H), 1.01 (dd, 6H) | |
| A83 | 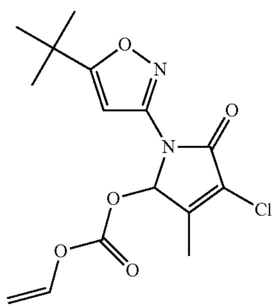 [SMILES: C=COC(=O)OC1C(C)=C(Cl)C(=O)N1c1cc(C(C)(C)C)on1] | 7.19-7.13 (m, 1H), 7.01 (s, 1H), 6.69 (s, 1H), 5.00 (dd, 1H), 4.70 (dd, 1H), 2.15 (s, 3H), 1.36 (s, 9H) | |
| A84 | 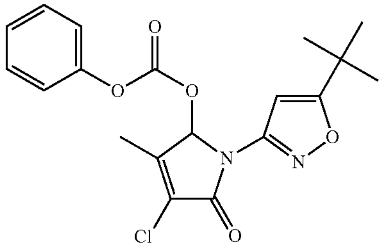 [SMILES: CC1=C(Cl)C(=O)N(c2cc(C(C)(C)C)on2)C1OC(=O)Oc1ccccc1] | 7.43 (m, 2H), 7.28 (m, 3H), 7.05 (s, 1H), 6.72 (s, 1H), 2.20 (s, 3H), 1.37 (s, 9H). | 113-127 |
| A85 | 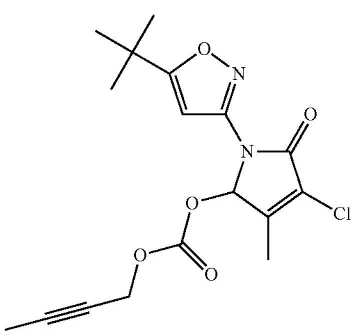 [SMILES: CC#CCOC(=O)OC1C(C)=C(Cl)C(=O)N1c1cc(C(C)(C)C)on1] | 6.99 (s, 1H), 6.68 (s, 1H), 4.90-4.77 (m, 2H), 2.14 (s, 3H), 1.90-1.88 (m, 3H), 1.35 (s, 9H) | |
| A86 | 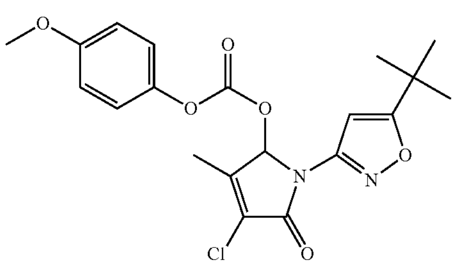 [SMILES: COc1ccc(OC(=O)OC2C(C)=C(Cl)C(=O)N2c2cc(C(C)(C)C)on2)cc1] | 7.19 (d, 2H), 7.03 (s, 1H), 6.91 (d, 2H), 6.71 (s, 1H), 3.81 (s, 3H), 2.18 (s, 3H), 1.37 (s, 9H) | |

TABLE 1-continued

| entry | STRUCTURE | 1H NMR (measured in CDCl₃ unless otherwise indicated) δ | MP ° C. |
|---|---|---|---|
| A87 | 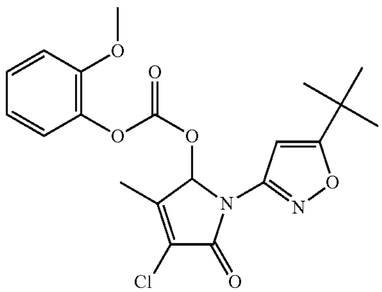 [SMILES: COc1ccccc1OC(=O)OC1C(C)=C(Cl)C(=O)N1c1cc(C(C)(C)C)on1] | 7.26 (m, 2H), 7.06 (s, 1H), 7.02-6.95 (m, 2H), 6.71 (s, 1H), 3.89 (s, 3H), 2.20 (s, 3H), 1.37 (s, 9H) | |
| A88 | 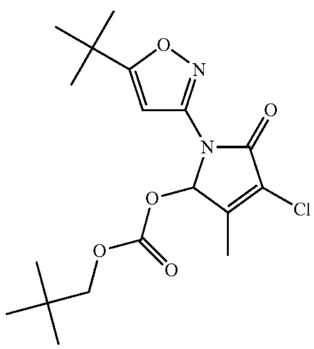 [SMILES: CC1=C(Cl)C(=O)N(c2cc(C(C)(C)C)on2)C1OC(=O)OCC(C)(C)C] | 7.00 (s, 1H), 6.69 (s, 1H), 6.02 (s, 2H), 2.13 (s, 3H), 1.34 (s, 9H), 0.98 (s, 9H) | |
| A90 | 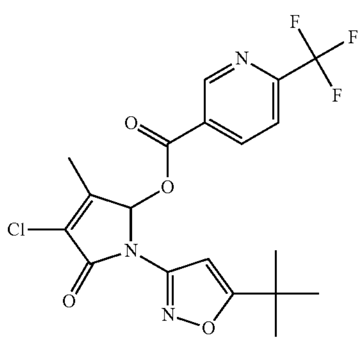 [SMILES: CC1=C(Cl)C(=O)N(c2cc(C(C)(C)C)on2)C1OC(=O)c1ccc(C(F)(F)F)nc1] | 9.29 (s, 1H), 8.50 (dd, 1H), 7.80 (d, 1H), 7.40 (s, 1H), 6.72 (s, 1H), 2.16 (s, 3H), 1.31 (s, 9H) | |
| A91 | 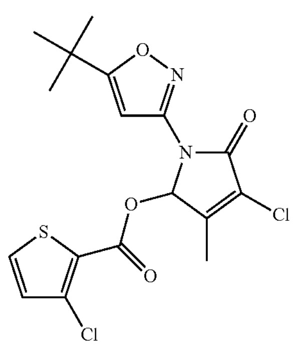 [SMILES: CC1=C(Cl)C(=O)N(c2cc(C(C)(C)C)on2)C1OC(=O)c1sccc1Cl] | | |

TABLE 1-continued

| entry | STRUCTURE | 1H NMR (measured in CDCl$_3$ unless otherwise indicated) δ | MP ° C. |
|---|---|---|---|
| A92 | 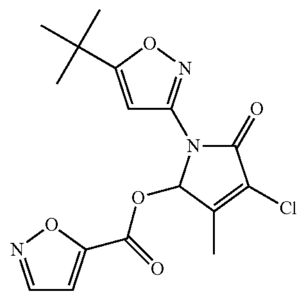 [SMILES: CC1=C(Cl)C(=O)N(c2cc(C(C)(C)C)on2)C1OC(=O)c1ccno1] | 8.40 (s, 1H), 7.37 (s, 1H), 7.05 (s, 1H), 6.71 (s, 1H), 2.15 (s, 3H), 1.33 (s, 9H) | |
| A93 | 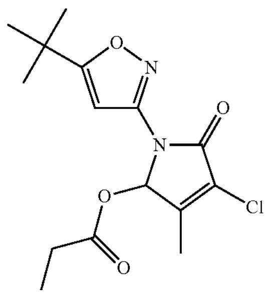 [SMILES: CCC(=O)OC1C(C)=C(Cl)C(=O)N1c1cc(C(C)(C)C)on1] | 7.14 (s, 1H), 6.67 (s, 1H), 2.44 (m, 2H), 2.05 (s, 3H), 1.32 (s, 9H), 1.18 (t, 3H) | |
| A94 | 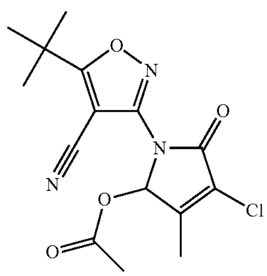 [SMILES: CC(=O)OC1C(C)=C(Cl)C(=O)N1c1noc(C(C)(C)C)c1C#N] | 7.14 (s, 1H), 2.17 (s, 3H), 2.09 (s, 3H), 1.51 (s, 9H) | 130-132 |
| A95 | 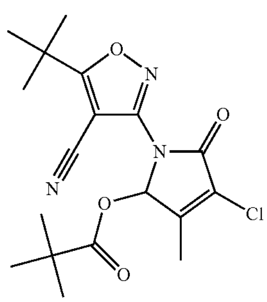 [SMILES: CC1=C(Cl)C(=O)N(c2noc(C(C)(C)C)c2C#N)C1OC(=O)C(C)(C)C] | 7.13 (s, 1H), 2.06 (s, 3H), 1.49 (s, 9H), 1.17 (s, 9H) | 95-97 |
| A96 | 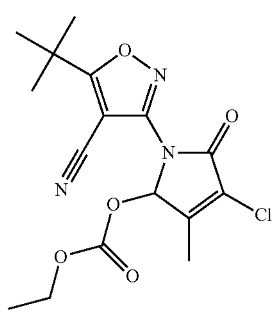 [SMILES: CCOC(=O)OC1C(C)=C(Cl)C(=O)N1c1noc(C(C)(C)C)c1C#N] | 6.96 (s, 1H), 4.30 (m, 2H), 2.13 (s, 3H), 1.50 (s, 9H), 1.33 (t, 3H) | |

TABLE 1-continued

| entry | STRUCTURE | 1H NMR (measured in CDCl₃ unless otherwise indicated) δ | MP ° C. |
|---|---|---|---|
| A97 | 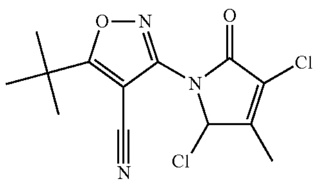 [SMILES: CC1=C(Cl)C(=O)N(c2noc(C(C)(C)C)c2C#N)C1Cl] | 6.44 (s, 1H), 2.25 (s, 3H), 1.52 (s, 9H) | |
| A98 | 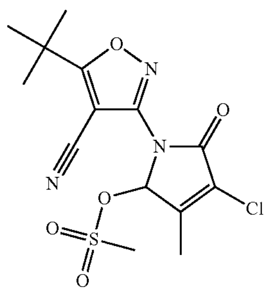 [SMILES: CC1=C(Cl)C(=O)N(c2noc(C(C)(C)C)c2C#N)C1OS(C)(=O)=O] | 6.44 (s, 1H), 2.25 (s, 3H), 1.52 (s, 9H), 1.51 (s, 3H) | |
| A99 | 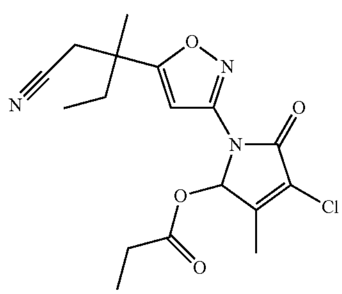 [SMILES: CCC(=O)OC1C(C)=C(Cl)C(=O)N1c1cc(C(C)(CC)CC#N)on1] | 7.16 (s, 1 H), 6.86 (s, 1H), 2.71 (m, 2H), 2.43 (m, 2H), 2.07 (s, 3H), 1.87 (m, 2H), 1.49 (s, 3H), 1.2 (t, 3H), 0.85 (m, 3H) | |
| A100 | 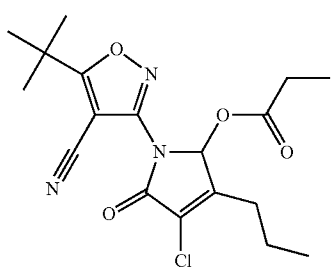 [SMILES: CCCC1=C(Cl)C(=O)N(c2noc(C(C)(C)C)c2C#N)C1OC(=O)CC] | 7.19 (s, 1H) 2.55 (m, 1H), 2.44 (m, 2H), 2.32 (m, 1H), 1.6 (m, 2H), 1.50 (s, 9H), 1.16 (t, 3H), 1.0 (t, 3H) | 69-71 |
| A101 | 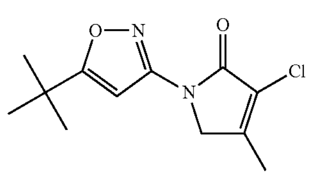 [SMILES: CC1=C(Cl)C(=O)N(c2cc(C(C)(C)C)on2)C1] | 6.79 (s, 1H), 4.4 (s, 2H), 2.19 (s, 3H), 1.38 (s, 9H). | 138-139 |
| A102 | 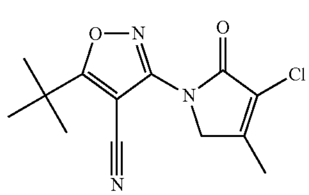 [SMILES: CC1=C(Cl)C(=O)N(c2noc(C(C)(C)C)c2C#N)C1] | 4.44 (s, 2H), 2.18 (s, 3H), 1.51 (s, 9H) | |

TABLE 1-continued

| entry | STRUCTURE | 1H NMR (measured in CDCl$_3$ unless otherwise indicated) δ | MP ° C. |
|---|---|---|---|
| A103 | 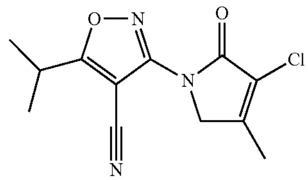 [SMILES: CC1=C(Cl)C(=O)N(c2noc(C(C)C)c2C#N)C1] | 4.42 (s, 2H), 3.39 (m, 1H), 2.18 (s, 3H), 1.43 (d, 6H) | 112-114 |
| A104 | 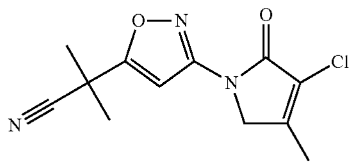 [SMILES: CC1=C(Cl)C(=O)N(c2cc(C(C)(C)C#N)on2)C1] | 7.12 (s, 1H), 4.40 (s, 2H), 2.18 (s, 3H), 1.79 (s, 6H) | 141-143 |
| A105 | 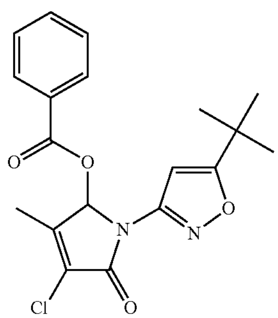 [SMILES: CC1=C(Cl)C(=O)N(c2cc(C(C)(C)C)on2)C1OC(=O)c1ccccc1] | 8.02-8.06 (m, 2H), 7.58-7.61 (1H, m), 7.42-7.47 (m, 3H), 7.26 (1H, s), 2.12 (3H, s), 1.31 (9H, s). | |
| A106 | 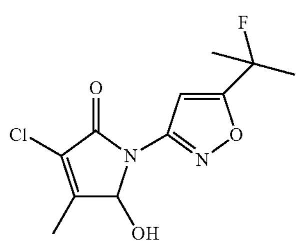 [SMILES: CC1=C(Cl)C(=O)N(c2cc(C(C)(C)F)on2)C1O] | 7.03 (s, 1H), 5.96 (s, 1H), 2.19 (s, 3H), 1.78 (d, J = 20 Hz, 6H) | |

TABLE 2

| Entry | STRUCTURE | 1H NMR (measured in CDCl$_3$ unless otherwise indicated) δ | MP ° C. |
|---|---|---|---|
| B1 | 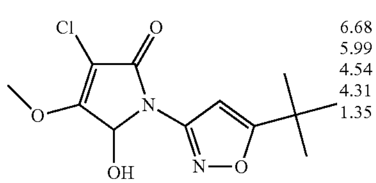 | 6.68 (s, 1H), 5.99 (s, 1H), 4.54 (s, 1H), 4.31 (s, 3H), 1.35 (s, 9H). | |
| B2 | | 6.69 (s, 1H), 6.03 (d, 1H), 4.53 (d, 1H), 4.31 (s, 3H), 1.35 (s, 9H). | 140-160 |

TABLE 3

| entry | STRUCTURE | 1H NMR (measured in CDCl₃ unless otherwise indicated) δ | MP ° C. |
|---|---|---|---|
| C1 | 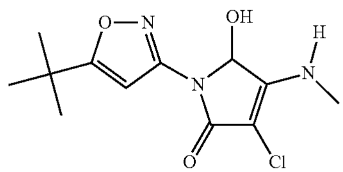 [SMILES: CNC1=C(Cl)C(=O)N(c2cc(C(C)(C)C)on2)C1O] | 6.71 (s, 1H), 6.01 (s, 1H), 5.58 (s, 1H), 5.22 (s, 1H), 3.24 (d, 3H), 1.33 (s, 9H). | |
| C2 | 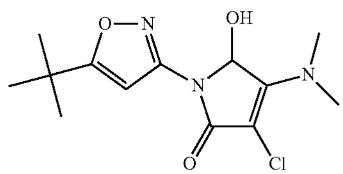 [SMILES: CN(C)C1=C(Cl)C(=O)N(c2cc(C(C)(C)C)on2)C1O] | 6.7 (s, 1H), 6.01 (s, 1H), 4.89 (s, 1H), 3.3 (s, 6H), 1.32 (s, 9H). | |
| C3 | 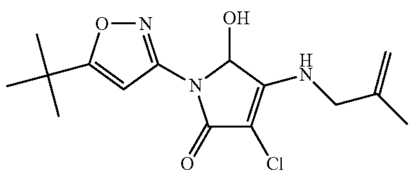 [SMILES: C=C(C)CNC1=C(Cl)C(=O)N(c2cc(C(C)(C)C)on2)C1O] | 6.71 (s, 1H), 6.01 (s, 1H), 5.1 (m, 2H), 4.95 (m, 2H), 4.1 (m, 2H), 1.8 (m, 3H), 1.34 (m, 9H). | |
| C4 | 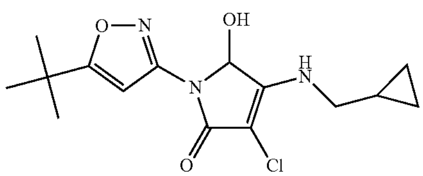 [SMILES: CC(C)(C)c1cc(N2C(=O)C(Cl)=C(NCC3CC3)C2O)no1] | 6.71 (s, 1H), 6.0 (s, 1H), 5.0 (m, 1H), 4.93 (m, 1H), 3.45 (m, 2H), 1.35 (s, 9H), 1.1 (m, 1H), 0.62 (m, 2H), 0.3 (m, 2H). | |
| C5 | 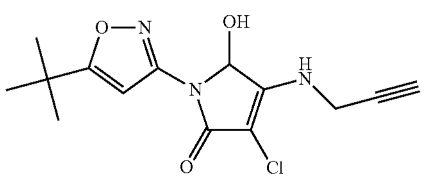 [SMILES: C#CCNC1=C(Cl)C(=O)N(c2cc(C(C)(C)C)on2)C1O] | 6.72 (s, 1H), 6.13 (s, 1H), 5.30 (m, 1H), 5.18 (m, 1H), 4.4 (m, 2H), 2.4 (m, 1H), 1.37 (s, 9H), | |
| C6 | 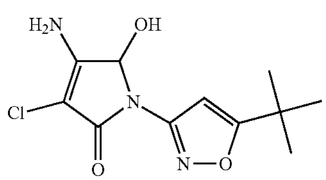 [SMILES: CC(C)(C)c1cc(N2C(=O)C(Cl)=C(N)C2O)no1] | 6.7 (s, 1H), 5.88 (s, 1H), 1.35 (s, 9H). | |
| C7 | 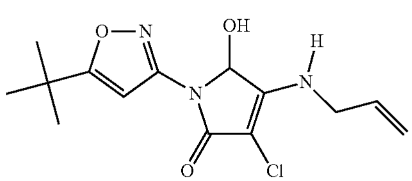 [SMILES: C=CCNC1=C(Cl)C(=O)N(c2cc(C(C)(C)C)on2)C1O] | 6.71 (s, 1H), 6.03 (s, 1H), 5.95 (m, 1H), 5.53 (s, 1H), 5.28 (m, 2H), 5.19 (m, 1H), 4.22 (m, 2H), 1.34 (s, 9H), | 163-164 |
| C8 | 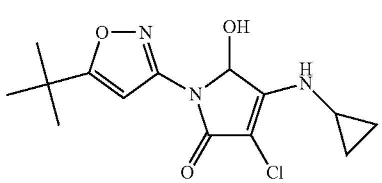 [SMILES: CC(C)(C)c1cc(N2C(=O)C(Cl)=C(NC3CC3)C2O)no1] | 6.73 (s, 1H), 6.08 (s, 1H), 5.8 (s, 1H), 5.42 (s, 1H), 3.05 (m, 1H), 1.34 (s, 9H), 0.86 (m, 2H), 0.76 (m, 1H), 0.69 (m, 1H). | 179-180 |

TABLE 3-continued

| entry | STRUCTURE | 1H NMR (measured in CDCl₃ unless otherwise indicated) δ | MP ° C. |
|---|---|---|---|
| C9 | 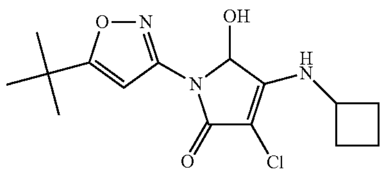 [SMILES: CC(C)(C)c1cc(N2C(=O)C(Cl)=C(NC3CCC3)C2O)no1] | 6.7 (s, 1H), 5.84 (s, 1H), 4.48 (m, 1H), 2.44 (m, 2H), 2.04 (m, 2H), 1.76 (m, 2H), 1.34 (s, 9H). | 210-202 |
| C10 | 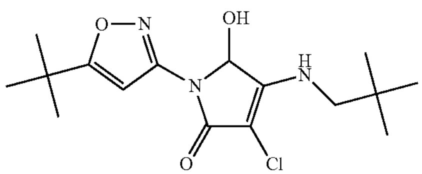 [SMILES: CC(C)(C)CNC1=C(Cl)C(=O)N(c2cc(C(C)(C)C)on2)C1O] | 6.72 (s, 1H), 5.96 (s, 1H), 5.18 (br s, 1H), 3.39 (m, 2H), 1.33 (s, 9H), 0.98 (s, 9H). | |
| C11 | 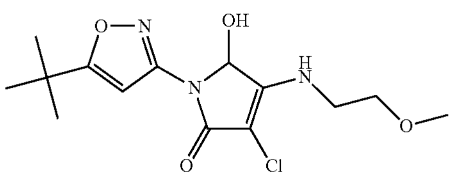 [SMILES: COCCNC1=C(Cl)C(=O)N(c2cc(C(C)(C)C)on2)C1O] | 6.71 (s, 1H), 6.01 (s, 1H), 5.35 (br s, 1H), 3.75 (m, 2H), 3.58 (m, 2H), 3.41 (s, 3H), 1.43 (s, 9H). | |
| C12 | 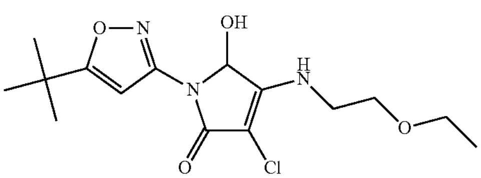 [SMILES: CCOCCNC1=C(Cl)C(=O)N(c2cc(C(C)(C)C)on2)C1O] | 6.71 (s, 1H), 6.01 (s, 1H), 5.40 (br s, 1H), 3.74 (m, 2H), 3.62 (m, 2H), 3.55 (q, 2H), 1.33 (s, 9H), 1.22 (t, 3H). | |
| C13 | 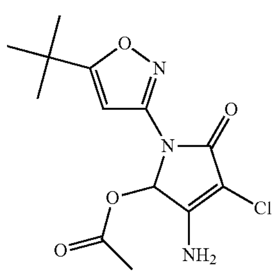 [SMILES: CC(=O)OC1C(N)=C(Cl)C(=O)N1c1cc(C(C)(C)C)on1] | 6.95 (s, 1H), 6.7 (s, 1H), 5.29 (br s, 2H), 2.22 (s, 3H), 1.36 (s, 9H). | |

TABLE 4

| entry | STRUCTURE | 1H NMR (measured in CDCl₃ unless otherwise indicated) δ | MP ° C. |
|---|---|---|---|
| D1 | 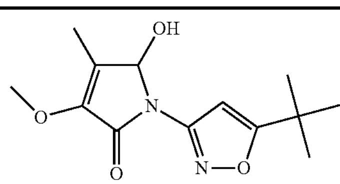 | 6.71 (s, 1H), 5.78 (d, 1H), 4.37 (d, 1H), 4.05 (s, 3H), 2.05 (s, 3H), 1.36 (s, 9H) | 82-95 |
| D2 | 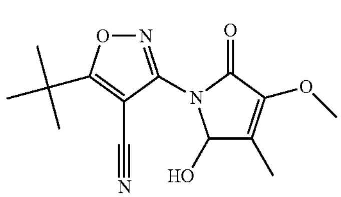 [SMILES: COC1=C(C)C(O)N(c2noc(C(C)(C)C)c2C#N)C1=O] | 5.83 (d, 1H), 4.06 (s, 3H), 3.62 (d, 1H), 2.02 (s, 3H), 1.51 (s, 9H) | 98-100 |

TABLE 4-continued

| entry | STRUCTURE | 1H NMR (measured in CDCl₃ unless otherwise indicated) δ | MP ° C. |
|---|---|---|---|
| D3 | 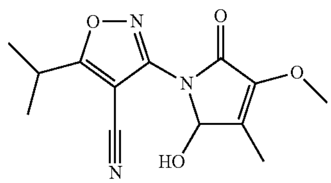 [SMILES: COC1=C(C)C(O)N(c2noc(C(C)C)c2C#N)C1=O] | 5.76 (d, 1H), 3.99 (s, 3H), 3.74 (d, 1H), 3.33 (m, 1H), 1.97 (s, 3H), 1.37 (d, 6H) | 99-101 |
| D4 | 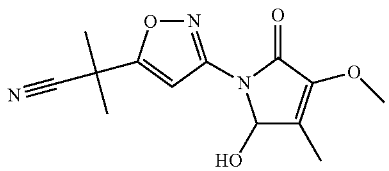 [SMILES: COC1=C(C)C(O)N(c2cc(C(C)(C)C#N)on2)C1=O] | 7.04 (s, 1H), 5.80 (d, 1H), 4.23 (d, 1H), 4.03 (s, 3H), 2.07 (s, 3H), 1.8 (s, 6H) | 123-125 |
| D5 | 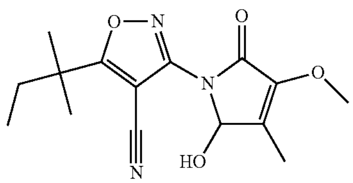 [SMILES: CCC(C)(C)c1onc(N2C(=O)C(OC)=C(C)C2O)c1C#N] | 5.83 (d, 1H), 4.06 (s, 3H), 3.66 (d, 1H), 2.02 (s, 3H), 1.87 (m, 2H), 1.51 (s, 6H), 0.86 (t, 3H) | 79-81 |
| D6 | 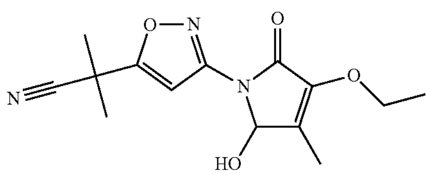 [SMILES: CCOC1=C(C)C(O)N(c2cc(C(C)(C)C#N)on2)C1=O] | 7.04 (s, 1H), 5.80 (d, 1H), 4.36 (m, 2H), 4.16 (d, 1H), 2.03 (s, 3H), 1.8 (s, 6H), 1.35 (t, 3H) | 90-92 |
| D7 | 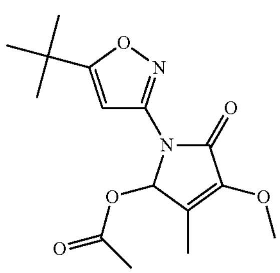 [SMILES: COC1=C(C)C(OC(C)=O)N(c2cc(C(C)(C)C)on2)C1=O] | 7.02 (s, 1H), 6.70 (s, 1H), 4.05 (s, 3H), 2.18 (s, 3H), 1.95 (s, 3H), 1.34 (s, 9H) | 118-124 |
| D8 | 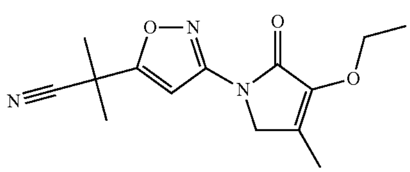 [SMILES: CCOC1=C(C)CN(c2cc(C(C)(C)C#N)on2)C1=O] | 7.11 (s, 1H), 4.29 (m, 2H), 4.22 (s, 2H), 2.02 (s, 3H), 1.78 (s, 6H), 1.33 (t, 3H) | 127-129 |
| D9 | 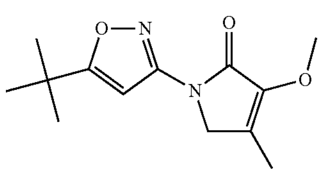 [SMILES: COC1=C(C)CN(c2cc(C(C)(C)C)on2)C1=O] | 6.78 (s, 1H), 4.2 (m, 2H), 4.0 (s, 3H), 2.04 (s, 3H), 1.36 (s, 9H). | |
| D10 | 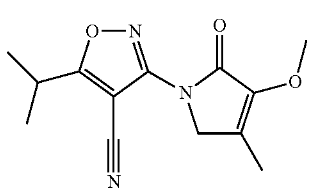 [SMILES: COC1=C(C)CN(c2noc(C(C)C)c2C#N)C1=O] | 4.24 (s, 2H), 4.01 (s, 3H), 3.38 (m, 1H), 2.02 (s, 3H), 1.42 (d, 6H) | 131-133 |

TABLE 4-continued

| entry | STRUCTURE | 1H NMR (measured in CDCl$_3$ unless otherwise indicated) δ | MP ° C. |
|---|---|---|---|
| D11 | 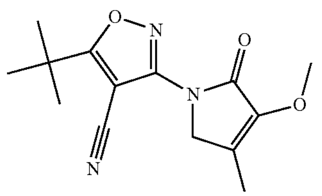 [SMILES: COC1=C(C)CN(c2noc(C(C)(C)C)c2C#N)C1=O] | 4.25 (s, 2H), 4.01 (s, 3H), 2.05 (s, 3H), 1.5 (s, 9H) | 138-140 |
| D12 | 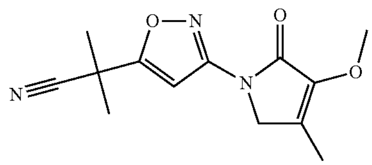 [SMILES: COC1=C(C)CN(c2cc(C(C)(C)C#N)on2)C1=O] | 7.12 (s, 1H), 4.22 (s, 2H), 3.99 (s, 3H), 2.04 (s, 3H), 1.78 (s, 6H) | 103-105 |
| D13 | 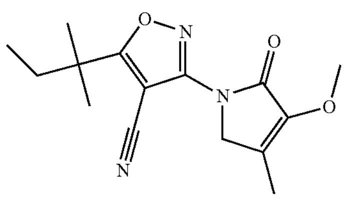 [SMILES: CCC(C)(C)c1onc(N2CC(C)=C(OC)C2=O)c1C#N] | 4.26 (s, 2H), 4.01 (s, 3H), 2.02 (s, 3H), 1.86 (m, 2H), 1.47 (s, 6H), 0.85 (t, 3H) | 72-74 |
| D14 | 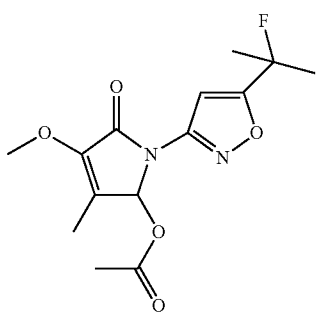 [SMILES: COC1=C(C)C(OC(C)=O)N(c2cc(C(C)(C)F)on2)C1=O] | 7.03 (s, 1H), 7.01 (s, 1H), 4.07 (s, 3H), 2.18 (s, 3H), 1.97 (s, 3H), 1.76 (d, J = 24 Hz, 6H). | |
| D15 | 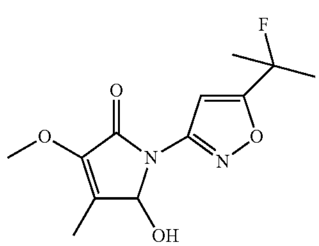 [SMILES: COC1=C(C)C(O)N(c2cc(C(C)(C)F)on2)C1=O] | 7.02 (s, 1H), 5.81 (s, 1H), 4.05 (s, 3H), 2.07 (s, 3H), 1.77 (d, J = 20 Hz, 6H). | |
| D16 | 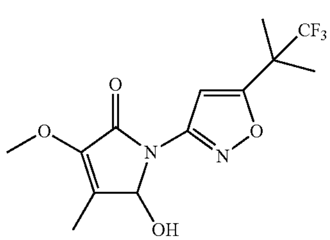 [SMILES: COC1=C(C)C(O)N(c2cc(C(C)(C)C(F)(F)F)on2)C1=O] | | |

TABLE 5

| entry | STRUCTURE | 1H NMR (measured in CDCl₃ unless otherwise indicated) δ | MP ° C. |
|---|---|---|---|
| E1 | 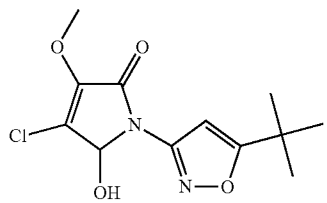 [SMILES: COC1=C(Cl)C(O)N(c2cc(C(C)(C)C)on2)C1=O] | 6.67 (s, 1H), 5.89 (s, 1H), 4.60 (br s, 1H), 4.22 (s, 3H), 1.36 (s, 9H) | 123-133 |
| E2 | 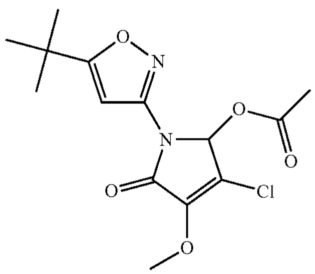 [SMILES: COC1=C(Cl)C(OC(C)=O)N(c2cc(C(C)(C)C)on2)C1=O] | 7.13 (s, 1H), 6.65 (s, 1H), 4.22 (s, 3H), 2.20 (s, 3H), 1.34 (s, 9H) | 101-107 |

TABLE 5-continued

| entry | STRUCTURE | 1H NMR (measured in CDCl₃ unless otherwise indicated) δ | MP ° C. |
|---|---|---|---|
| E3 | 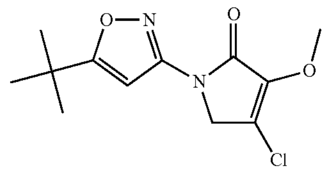 [SMILES: COC1=C(Cl)CN(c2cc(C(C)(C)C)on2)C1=O] | 6.72 (s, 1H), 4.38 (s, 2H), 4.17 (s, 3H), 1.35 (s, 9H) | 94-106 |

TABLE 6

| Entry | STRUCTURE | 1H NMR (measured in CDCl₃ unless otherwise indicated) δ | MP ° C. |
|---|---|---|---|
| F1 | 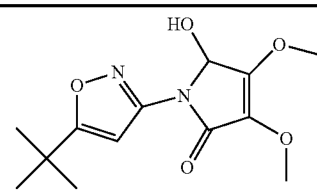 | 6.68 (s, 1H), 5.86 (d, 1H), 4.45 (d, 1H), 4.17 (s, 3H), 3.93 (s, 3H), 1.36 (s, 9H) | |

TABLE 7

| entry | STRUCTURE | 1H NMR (measured in CDCl₃ unless otherwise indicated) δ | MP ° C. |
|---|---|---|---|
| G1 | 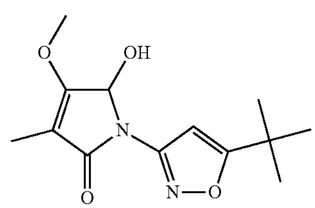 [SMILES: COC1=C(C)C(=O)N(c2cc(C(C)(C)C)on2)C1O] | 6.71 (s, 1H), 5.98 (d, 1H), 4.74 (d, 1H), 4.12 (s, 3H), 1.88 (s, 3H), 1.35 (s, 9H) | |
| G2 | 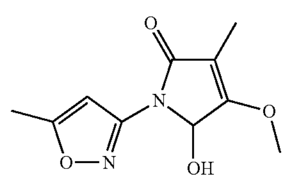 | 6.73 (s, 1H), 5.98 (d, 1H), 4.79 (d, 1H), 4.12 (s, 3H), 2.41 (s, 3H), 1.87 (s, 3H) | |
| G3 | 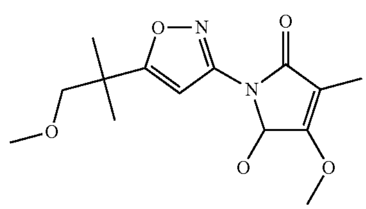 | 6.78 (s, 1H), 5.96 (d, 1H), 4.54 (d, 1H), 4.12 (s, 3H), 3.44 (s, 2H), 3.33 (s, 3H), 1.88 (s, 3H), 1.34 (s, 6H) | |

TABLE 7-continued

| entry | STRUCTURE | 1H NMR (measured in CDCl₃ unless otherwise indicated) δ | MP ° C. |
|---|---|---|---|
| G4 | 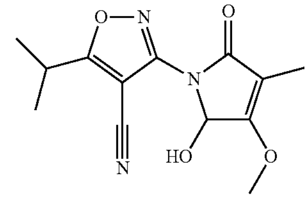 [SMILES: COC1=C(C)C(=O)N(c2noc(C(C)C)c2C#N)C1O] | 5.98 (d, 1H), 4.14 (s, 3H), 3.98 (br s, 1H), 3.39 (m, 1H), 1.91 (s, 3H), 1.41 (d, 6H) | 133-135 |
| G5 | 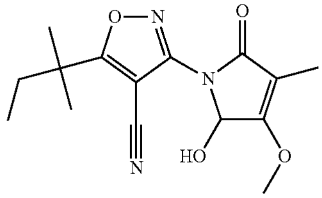 [SMILES: CCC(C)(C)c1onc(N2C(=O)C(C)=C(OC)C2O)c1C#N] | 5.99 (d, 1H), 4.13 (s, 3H), 3.79 (br s, 1H), 1.92 (s, 3H), 1.85 (m, 2H), 1.48 (s, 6H), 0.86 (t, 3H) | 122-124 |
| G6 | 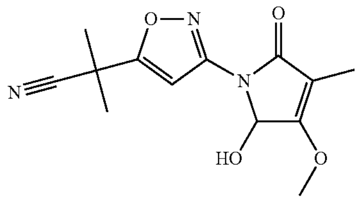 [SMILES: COC1=C(C)C(=O)N(c2cc(C(C)(C)C#N)on2)C1O] | 7.04 (s, 1H), 5.97 (s, 1H), 4.24 (s, 1H), 4.14 (s, 3H), 1.88 (s, 3H), 1.78 (s, 6H) | 121-123 |
| G7 | 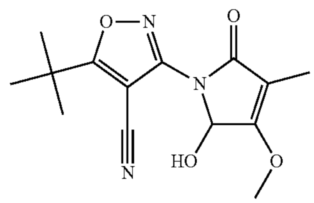 [SMILES: COC1=C(C)C(=O)N(c2noc(C(C)(C)C)c2C#N)C1O] | 5.98 (d, 1H), 4.14 (s, 3H), 3.84 (d, 1H), 1.92 (s, 3H), 1.51 (s, 9H) | |

Example 15

Herbicidal Action

Example 15a

Pre-Emergence Herbicidal Activity

Seeds of a variety of test species were sown in standard soil in pots. After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 8.

TABLE 8

Application pre-emergence

| Compound Number | Rate (g/Ha) | AMARE | ABUTH | SETFA | ECHCG | ALOMY | ZEAMX |
|---|---|---|---|---|---|---|---|
| A1 | 1000 | 5 | 5 | 5 | 4 | 2 | 1 |
| A2 | 1000 | 5 | 5 | 5 | 5 | 3 | 3 |
| A3 | 1000 | 5 | 5 | 5 | 3 | 3 | 2 |
| A4 | 1000 | 5 | 5 | 5 | 4 | 3 | 2 |
| A6 | 1000 | 0 | 0 | 1 | 1 | 1 | 0 |
| A7 | 1000 | 5 | 5 | 4 | 4 | 3 | 2 |
| A8 | 1000 | 5 | 5 | 4 | 4 | 3 | 1 |
| A11 | 1000 | 5 | 5 | 5 | 5 | 4 | 2 |
| A12 | 1000 | 4 | 5 | 5 | 5 | 4 | 1 |
| A13 | 1000 | 5 | 3 | 3 | 3 | 3 | 1 |
| A14 | 1000 | 5 | 5 | 5 | 4 | 3 | 2 |

TABLE 8-continued

Application pre-emergence

| Compound Number | Rate (g/Ha) | AMARE | ABUTH | SETFA | ECHCG | ALOMY | ZEAMX |
|---|---|---|---|---|---|---|---|
| A15 | 1000 | 5 | 5 | 3 | 4 | 2 | 2 |
| A16 | 1000 | 5 | 5 | 5 | 5 | 4 | 3 |
| A17 | 1000 | 5 | 3 | 3 | 5 | 2 | 2 |
| A18 | 1000 | 1 | 4 | 3 | 2 | 4 | 1 |
| A19 | 1000 | 5 | | 5 | 5 | 4 | |
| A20 | 1000 | 1 | | 5 | 5 | 4 | |
| A21 | 1000 | 5 | | 3 | 5 | 3 | |
| A22 | 1000 | 4 | 5 | 5 | 5 | 4 | 1 |
| A23 | 1000 | 5 | 5 | 3 | 5 | 4 | 3 |
| A24 | 1000 | 4 | 5 | 4 | 5 | 4 | 2 |
| A25 | 1000 | 5 | 3 | 0 | 2 | 2 | 0 |
| A26 | 1000 | 5 | 5 | 5 | 5 | 4 | 3 |
| A27 | 1000 | 5 | 5 | 4 | 5 | 4 | 4 |
| A28 | 1000 | 5 | 5 | 4 | 5 | 4 | 2 |
| A29 | 1000 | 5 | 5 | 4 | 5 | 3 | 1 |
| A30 | 1000 | 4 | 2 | 1 | 1 | 2 | 1 |
| A31 | 1000 | 5 | 5 | 5 | 5 | 3 | 3 |
| A32 | 1000 | 1 | 4 | 1 | 3 | 2 | 1 |
| A33 | 1000 | 5 | 3 | 3 | 4 | 2 | 3 |
| A34 | 1000 | 5 | 5 | 4 | 5 | 3 | 2 |
| A35 | 1000 | 3 | 1 | 0 | 0 | 1 | 0 |
| A36 | 1000 | 5 | 5 | 1 | 4 | 3 | 1 |
| A37 | 1000 | 5 | 5 | 4 | 5 | 4 | 1 |
| A38 | 1000 | 5 | 1 | 2 | 5 | 3 | 1 |
| A39 | 1000 | 4 | 1 | 0 | 3 | 1 | 1 |
| A40 | 1000 | 5 | 4 | 5 | 5 | 3 | 2 |
| A41 | 1000 | 5 | 5 | 5 | 4 | 4 | 3 |
| A42 | 1000 | 5 | 5 | 5 | 4 | 4 | 2 |
| A43 | 1000 | 5 | 4 | 5 | 4 | 4 | 2 |
| A44 | 1000 | 5 | 5 | 5 | 4 | 4 | 3 |
| A45 | 1000 | 5 | 4 | 4 | 3 | 3 | 2 |
| A46 | 1000 | 5 | 2 | 4 | 4 | 4 | 3 |
| A47 | 1000 | 5 | 0 | 1 | 2 | 2 | 2 |
| A49 | 1000 | 5 | 5 | 5 | 4 | 3 | 1 |
| A50 | 1000 | 5 | 5 | 5 | 4 | 3 | 3 |
| A51 | 1000 | 5 | 4 | 4 | 4 | 3 | 3 |
| A52 | 1000 | 5 | 5 | 5 | 5 | 4 | 4 |
| A53 | 1000 | 5 | 5 | 5 | 5 | 4 | 4 |
| A54 | 1000 | 5 | 5 | 5 | 5 | 4 | 4 |
| A55 | 1000 | 5 | 5 | 5 | 5 | 4 | 3 |
| A58 | 1000 | 5 | 5 | 5 | 5 | 4 | 4 |
| A59 | 1000 | 5 | 5 | 5 | 5 | 5 | 5 |
| A60 | 1000 | 5 | 5 | 5 | 4 | 3 | 3 |
| A61 | 1000 | 5 | 5 | 5 | 5 | 4 | 3 |
| A62 | 1000 | 5 | 5 | 5 | 4 | 3 | 3 |
| A63 | 1000 | 5 | 5 | 5 | 5 | 3 | 3 |
| A64 | 1000 | 5 | 4 | 5 | 5 | 3 | 1 |
| A65 | 1000 | 5 | 5 | 5 | 5 | 3 | 2 |
| A66 | 1000 | 5 | 5 | 4 | 5 | 3 | 1 |
| A68 | 1000 | 3 | 4 | 5 | 5 | 3 | 1 |
| A69 | 1000 | 2 | 0 | 1 | 1 | 0 | 0 |
| A70 | 1000 | 5 | 0 | 3 | 4 | 1 | 1 |
| A71 | 1000 | 5 | 4 | 5 | 4 | 3 | 2 |
| A72 | 1000 | 5 | 5 | 5 | 5 | 4 | 4 |
| A73 | 1000 | 5 | 5 | 5 | 4 | 3 | 3 |
| A74 | 1000 | 5 | 5 | 5 | 5 | 4 | 4 |
| A75 | 1000 | 5 | 5 | 4 | 4 | 4 | 3 |
| A76 | 1000 | 5 | 5 | 4 | 4 | 4 | 3 |
| A77 | 1000 | 4 | 1 | 2 | 1 | 1 | 1 |
| A78 | 1000 | 5 | 5 | 5 | 5 | 2 | 2 |
| A80 | 1000 | 5 | 5 | 5 | 5 | 4 | 3 |
| A81 | 1000 | 5 | 5 | 5 | 5 | 4 | 3 |
| A82 | 1000 | 3 | 1 | 1 | 1 | 0 | 0 |
| A83 | 1000 | 5 | 5 | 5 | 5 | 4 | 4 |
| A84 | 1000 | 5 | 5 | 5 | 5 | 4 | 3 |
| A85 | 1000 | 5 | 5 | 5 | 5 | 4 | 3 |
| A86 | 1000 | 5 | 3 | 2 | 2 | 3 | 1 |
| A87 | 1000 | 3 | 2 | 1 | 1 | 2 | 0 |
| A88 | 1000 | 5 | 5 | 5 | 5 | 4 | 3 |
| A90 | 1000 | 5 | 4 | 2 | 1 | 2 | 1 |
| A91 | 1000 | 4 | 1 | 0 | 0 | 2 | 0 |
| A92 | 1000 | 5 | 5 | 4 | 5 | 4 | 3 |
| A93 | 1000 | 5 | 5 | 5 | 4 | 4 | 3 |
| A94 | 1000 | 5 | 5 | 5 | 5 | 4 | 3 |
| A95 | 1000 | 5 | 4 | 5 | 5 | 4 | 3 |

TABLE 8-continued

Application pre-emergence

| Compound Number | Rate (g/Ha) | AMARE | ABUTH | SETFA | ECHCG | ALOMY | ZEAMX |
|---|---|---|---|---|---|---|---|
| A96 | 1000 | 5 | 5 | 5 | 5 | 4 | 3 |
| A97 | 1000 | 5 | 5 | 5 | 4 | 4 | 3 |
| A98 | 1000 | 5 | 5 | 5 | 5 | 3 | 3 |
| A99 | 1000 | 5 | 5 | 5 | 5 | 4 | 3 |
| A100 | 1000 | 5 | 5 | 5 | 5 | 4 | 3 |
| A101 | 1000 | 5 | 5 | 4 | 5 | 4 | 3 |
| A102 | 1000 | 5 | 5 | 5 | 4 | 4 | 3 |
| A103 | 1000 | 5 | 5 | 5 | 5 | 4 | 2 |
| A104 | 1000 | 5 | 5 | 5 | 5 | 4 | 2 |
| B1 | 1000 | 5 | 5 | 3 | 5 | 4 | 4 |
| B2 | 1000 | 5 | 5 | 4 | 5 | 4 | 1 |
| C1 | 1000 | 5 | 3 | 4 | 4 | 2 | 1 |
| C2 | 1000 |   | 1 | 1 | 2 | 1 | 1 |
| C3 | 1000 | 5 | 5 | 3 | 4 | 3 | 2 |
| C4 | 1000 | 5 | 5 | 4 | 5 | 2 | 3 |
| C5 | 1000 | 5 | 5 | 4 | 5 | 3 | 3 |
| C6 | 1000 | 5 | 5 | 4 | 5 | 4 | 4 |
| C7 | 1000 | 5 | 5 | 3 | 5 | 3 | 2 |
| C8 | 1000 | 5 | 5 | 3 | 5 | 3 | 2 |
| C9 | 1000 | 3 | 0 | 0 | 0 | 0 | 0 |
| C10 | 1000 | 2 | 0 | 0 | 0 | 0 | 0 |
| C11 | 1000 | 5 | 4 | 4 | 4 | 3 | 2 |
| C12 | 1000 | 4 | 4 | 3 | 2 | 1 | 0 |
| C13 | 1000 | 5 | 5 | 4 | 5 | 4 | 4 |
| D1 | 1000 | 5 | 5 | 5 | 4 | 4 | 2 |
| D2 | 1000 | 5 | 5 | 5 | 4 | 3 | 3 |
| D3 | 1000 | 5 | 4 | 5 | 5 | 3 | 2 |
| D4 | 1000 | 5 | 5 | 5 | 5 | 4 | 3 |
| D5 | 1000 | 5 | 5 | 5 | 5 | 4 | 2 |
| D6 | 1000 | 5 | 5 | 4 | 5 | 4 | 3 |
| D7 | 1000 | 5 | 5 | 5 | 4 | 3 | 2 |
| D8 | 1000 | 4 | 3 | 4 | 3 | 2 | 2 |
| D9 | 1000 | 5 |   | 4 | 4 | 4 |   |
| D10 | 1000 |   | 4 | 5 | 5 | 3 | 2 |
| D11 | 1000 | 5 | 4 | 5 | 5 | 4 | 3 |
| D12 | 1000 | 5 | 5 | 4 | 5 | 4 | 2 |
| D13 | 1000 | 5 | 2 | 2 | 4 | 2 | 2 |
| E1 | 1000 | 5 | 4 | 3 | 3 | 2 | 2 |
| E2 | 1000 | 5 | 5 | 3 | 4 | 3 | 1 |
| E3 | 1000 | 5 | 2 | 3 | 3 | 1 | 1 |
| F1 | 1000 | 5 | 5 | 4 | 4 | 3 | 2 |
| G1 | 1000 | 5 | 5 | 4 | 5 | 3 | 1 |
| G2 | 1000 | 5 | 5 | 3 | 3 | 1 | 1 |
| G3 | 1000 | 5 | 5 | 5 | 5 | 3 | 4 |
| G4 | 1000 | 5 | 4 | 5 | 5 | 3 | 2 |
| G5 | 1000 | 5 | 5 | 5 | 5 | 3 | 2 |
| G6 | 1000 | 5 | 5 | 5 | 4 | 4 | 4 |
| G7 | 1000 | 5 | 5 | 5 | 5 | 4 | 4 |

Example 15b

Post-Emergence Herbicidal Activity

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 9.

TABLE 9

Application post-emergence

| ID | Rate (g/Ha) | AMARE | ABUTH | ECHCG | SETFA | ALOMY | ZEAMX |
|---|---|---|---|---|---|---|---|
| A1 | 1000 | 5 | 5 | 5 | 5 | 5 | 4 |
| A2 | 1000 | 5 | 5 | 5 | 5 | 5 | 5 |
| A3 | 1000 | 5 | 5 | 5 | 5 | 4 | 3 |
| A4 | 1000 | 5 | 5 | 5 | 5 | 4 | 3 |
| A6 | 1000 | 4 | 4 | 3 | 2 | 2 | 0 |

TABLE 9-continued

| | | Application post-emergence | | | | | |
|---|---|---|---|---|---|---|---|
| ID | Rate (g/Ha) | AMARE | ABUTH | ECHCG | SETFA | ALOMY | ZEAMX |
| A7 | 1000 | 4 | 5 | 5 | 5 | 5 | 5 |
| A8 | 1000 | 3 | 5 | 5 | 5 | 5 | 3 |
| A9 | 1000 | 5 | 5 | 5 | 5 | 4 | 5 |
| A10 | 1000 | 5 | 5 | 5 | 5 | 4 | 5 |
| A11 | 1000 | 5 | 5 | 5 | 5 | 5 | 5 |
| A12 | 1000 | 5 | 5 | 5 | 5 | 5 | 4 |
| A13 | 1000 | 5 | 5 | 5 | 5 | 5 | 2 |
| A14 | 1000 | 4 | 5 | 5 | 5 | 5 | 4 |
| A15 | 1000 | 5 | 5 | 5 | 5 | 4 | 3 |
| A16 | 1000 | 5 | 5 | 5 | 5 | 5 | 5 |
| A17 | 1000 | 5 | 5 | 5 | 5 | 5 | 4 |
| A18 | 1000 | 4 | 5 | 5 | 5 | 5 | 3 |
| A19 | 1000 | 5 | | 5 | 5 | 5 | |
| A20 | 1000 | 4 | | 5 | 5 | 5 | |
| A21 | 1000 | 5 | | 5 | 5 | 5 | |
| A22 | 1000 | 5 | 5 | 5 | 5 | 5 | 4 |
| A23 | 1000 | 5 | 5 | 5 | 5 | 5 | 4 |
| A24 | 1000 | 5 | 5 | 5 | 5 | 5 | 4 |
| A25 | 1000 | 4 | 5 | 4 | 5 | 3 | 1 |
| A26 | 1000 | 5 | 5 | 5 | 5 | 4 | 5 |
| A27 | 1000 | 5 | 5 | 5 | 5 | 5 | 4 |
| A28 | 1000 | 5 | 5 | 5 | 5 | 5 | 4 |
| A29 | 1000 | 5 | 5 | 5 | 4 | 4 | 3 |
| A30 | 1000 | 5 | 5 | 5 | 4 | 3 | 2 |
| A31 | 1000 | 5 | 5 | 5 | 5 | 5 | 4 |
| A32 | 1000 | 2 | 5 | 5 | 2 | 2 | 2 |
| A33 | 1000 | 5 | 5 | 5 | 4 | 4 | 5 |
| A34 | 1000 | 5 | 5 | 5 | 4 | 4 | 5 |
| A35 | 1000 | 5 | 4 | 2 | 0 | 1 | 1 |
| A36 | 1000 | 5 | 5 | 5 | 2 | 4 | 1 |
| A37 | 1000 | 5 | 5 | 5 | 5 | 5 | 3 |
| A38 | 1000 | 5 | 5 | 5 | 5 | 5 | 2 |
| A39 | 1000 | 5 | 4 | 5 | 1 | 3 | 1 |
| A40 | 1000 | 5 | 5 | 5 | 5 | 4 | 3 |
| A41 | 1000 | 5 | 5 | 5 | 5 | 5 | 4 |
| A42 | 1000 | 5 | 5 | 5 | 5 | 5 | 4 |
| A43 | 1000 | 5 | 5 | 5 | 5 | 5 | 2 |
| A44 | 1000 | 5 | 5 | 5 | 5 | 5 | 4 |
| A45 | 1000 | 5 | 5 | 5 | 5 | 5 | 3 |
| A46 | 1000 | 5 | 5 | 5 | 5 | 5 | 3 |
| A47 | 1000 | 5 | 5 | 5 | 5 | 5 | 2 |
| A49 | 1000 | 5 | 5 | 5 | 5 | 4 | 2 |
| A50 | 1000 | 5 | 5 | 5 | 5 | 4 | 3 |
| A51 | 1000 | 5 | 5 | 5 | 5 | 4 | 3 |
| A52 | 1000 | 5 | 5 | 5 | 5 | 5 | 5 |
| A53 | 1000 | 5 | 5 | 5 | 5 | 5 | 5 |
| A54 | 1000 | 5 | 5 | 5 | 5 | 5 | 5 |
| A55 | 1000 | 5 | 5 | 5 | 5 | 5 | 4 |
| A58 | 1000 | 5 | 5 | 5 | 5 | 5 | 5 |
| A59 | 1000 | 5 | 5 | 5 | 5 | 5 | 5 |
| A60 | 1000 | 5 | 5 | 5 | 5 | 4 | 2 |
| A61 | 1000 | 5 | 5 | 5 | 5 | 5 | 3 |
| A62 | 1000 | 5 | 5 | 5 | 5 | 4 | 3 |
| A63 | 1000 | 5 | 5 | 5 | 5 | 4 | 3 |
| A64 | 1000 | 5 | 5 | 5 | 5 | 5 | 4 |
| A65 | 1000 | 5 | 5 | 5 | 5 | 5 | 4 |
| A66 | 1000 | 5 | 5 | 5 | 5 | 5 | 3 |
| A68 | 1000 | 5 | 5 | 5 | 5 | 5 | 1 |
| A69 | 1000 | 5 | 4 | 5 | 5 | 2 | 1 |
| A70 | 1000 | 5 | 2 | 5 | 5 | 3 | 1 |
| A71 | 1000 | 5 | 5 | 5 | 5 | 4 | 2 |
| A72 | 1000 | 5 | 5 | 5 | 5 | 5 | 5 |
| A73 | 1000 | 5 | 5 | 5 | 5 | 4 | 2 |
| A74 | 1000 | 5 | 5 | 5 | 5 | 5 | 5 |
| A75 | 1000 | 5 | 5 | 5 | 5 | 5 | 5 |
| A76 | 1000 | 5 | 5 | 5 | 5 | 5 | 4 |
| A77 | 1000 | 3 | 1 | 3 | 2 | 2 | 1 |
| A78 | 1000 | 5 | 5 | 5 | 5 | 5 | 4 |
| A79 | 1000 | 5 | 2 | 3 | 3 | 2 | 1 |
| A80 | 1000 | 5 | 5 | 5 | 5 | 5 | 3 |
| A81 | 1000 | 5 | 5 | 5 | 5 | 5 | 4 |
| A82 | 1000 | 2 | | 2 | 2 | | 1 |
| A83 | 1000 | 5 | 5 | 5 | 5 | 5 | 4 |
| A84 | 1000 | 5 | 5 | 5 | 5 | 5 | 3 |
| A85 | 1000 | 5 | 5 | 5 | 5 | 5 | 4 |

TABLE 9-continued

| | | Application post-emergence | | | | | |
|---|---|---|---|---|---|---|---|
| ID | Rate (g/Ha) | AMARE | ABUTH | ECHCG | SETFA | ALOMY | ZEAMX |
| A86 | 1000 | 5 | 2 | 2 | 3 | 3 | 0 |
| A87 | 1000 | 4 | 2 | 3 | 2 | 2 | 0 |
| A88 | 1000 | 5 | 5 | 5 | 5 | 5 | 5 |
| A90 | 1000 | 5 | 4 | 2 | 3 | 4 | 1 |
| A91 | 1000 | 5 | 2 | 1 | 1 | 2 | 0 |
| A92 | 1000 | 5 | 5 | 5 | 5 | 5 | 1 |
| A93 | 1000 | 5 | 5 | 5 | 5 | 5 | 4 |
| A94 | 1000 | 5 | 5 | 5 | 5 | 5 | 4 |
| A95 | 1000 | 5 | 5 | 5 | 5 | 5 | 3 |
| A96 | 1000 | 5 | 5 | 5 | 5 | 5 | 5 |
| A97 | 1000 | 5 | 5 | 5 | 5 | 5 | 3 |
| A98 | 1000 | 5 | 5 | 5 | 5 | 5 | 4 |
| A99 | 1000 | 5 | 5 | 5 | 5 | 5 | 5 |
| A100 | 1000 | 5 | 5 | 5 | 5 | 5 | 5 |
| A101 | 1000 | 5 | 5 | 5 | 5 | 5 | 4 |
| A102 | 1000 | 5 | 5 | 5 | 5 | 5 | 4 |
| A103 | 1000 | 5 | 5 | 5 | 5 | 4 | 3 |
| A104 | 1000 | 5 | 5 | 5 | 5 | 5 | 5 |
| B1 | 1000 | 5 | 5 | 5 | 5 | 5 | 5 |
| B2 | 1000 | 5 | 5 | 5 | 4 | 4 | 5 |
| C1 | 1000 | 5 | 5 | 5 | 4 | 4 | 1 |
| C2 | 1000 | 5 | 5 | 5 | 4 | 4 | 3 |
| C3 | 1000 | 5 | 5 | 5 | 5 | 4 | 2 |
| C4 | 1000 | 5 | 5 | 5 | 5 | 5 | 4 |
| C5 | 1000 | 5 | 5 | 5 | 5 | 5 | 5 |
| C6 | 1000 | 5 | 3 | 5 | 5 | 5 | 5 |
| C7 | 1000 | 5 | 5 | 5 | 5 | 4 | 3 |
| C8 | 1000 | 5 | 5 | 5 | 5 | 4 | 4 |
| C9 | 1000 | 2 | 0 | 0 | 0 | 0 | 0 |
| C10 | 1000 | 0 | 0 | 0 | 0 | 0 | 0 |
| C11 | 1000 | 5 | 5 | 5 | 5 | 4 | 1 |
| C12 | 1000 | 4 | 5 | 4 | 4 | 3 | 0 |
| C13 | 1000 | 5 | 5 | 5 | 5 | 5 | 5 |
| D1 | 1000 | 5 | 5 | 5 | 5 | 4 | 4 |
| D2 | 1000 | 5 | 5 | 5 | 5 | 5 | 4 |
| D3 | 1000 | 5 | 5 | 5 | 5 | 5 | 4 |
| D4 | 1000 | 5 | 5 | 5 | 5 | 5 | 5 |
| D5 | 1000 | 5 | 5 | 5 | 5 | 5 | 5 |
| D6 | 1000 | 5 | 5 | 5 | 5 | 4 | 2 |
| D7 | 1000 | 5 | 5 | 5 | 5 | 4 | 3 |
| D8 | 1000 | 5 | 4 | 4 | 3 | 3 | 0 |
| D9 | 1000 | 5 | | 5 | 5 | 5 | |
| D10 | 1000 | 5 | 4 | 5 | 5 | 5 | 2 |
| D11 | 1000 | 5 | 5 | 5 | 5 | 5 | 4 |
| D12 | 1000 | 5 | 4 | 5 | 5 | 4 | 2 |
| D13 | 1000 | 5 | 4 | 5 | 5 | 5 | 2 |
| E1 | 1000 | 5 | 5 | 5 | 5 | 3 | 0 |
| E2 | 1000 | 5 | 5 | 5 | 5 | 3 | 0 |
| E3 | 1000 | 2 | 1 | 2 | 4 | 0 | 0 |
| F1 | 1000 | 5 | 5 | 5 | 5 | 4 | 5 |
| G1 | 1000 | 5 | 5 | 5 | 5 | 5 | 5 |
| G2 | 1000 | 5 | 3 | 2 | 1 | 2 | 1 |
| G3 | 1000 | 3 | 5 | 5 | 5 | 4 | 5 |
| G4 | 1000 | 5 | 5 | 5 | 5 | 5 | 4 |
| G5 | 1000 | 5 | 5 | 5 | 5 | 5 | 3 |
| G6 | 1000 | 5 | 5 | 5 | 5 | 5 | 5 |
| G7 | 1000 | 5 | 5 | 5 | 5 | 5 | 5 |

ABUTH = *Abutilon theophrasti*;; AMARE = *Amaranthus retroflexus*; SETFA = *Setaria faberi*; ALOMY = *Alopecurus myosuroides*; ECHCG = *Echinochloa crus-galli*; ZEAMX = *Zea mays*.

The invention claimed is:
1. A herbicidal compound of formula (I)

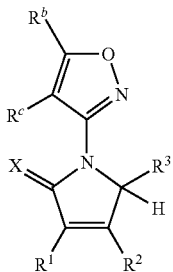

wherein
X is selected from S and O;
$R^b$ is selected from hydrogen, formyl, hydroxyl, halogen, nitro, cyano, $C_1$-$C_8$alkyl, $C_1$-$C_6$ cyanoalkyl, $C_1$-$C_6$ haloalkyl, $C_1$-$C_6$ hydroxyalkyl, $C_2$-$C_6$alkenyloxy $C_1$-$C_6$ alkyl, $C_1$-$C_6$ alkylthio, $C_1$-$C_6$ alkoxy, $C_1$-$C_6$ alkoxy $C_1$-$C_6$ alkyl, $C_1$-$C_6$ alkylthio $C_1$-$C_6$ alkyl, $C_1$-$C_6$ cyanoalkoxy, $C_1$-$C_6$ haloalkoxy, $C_1$-$C_6$ alkoxy $C_1$-$C_6$ alkoxy, $C_2$-$C_8$ alkenyl, $C_2$-$C_8$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, tri $C_1$-$C_6$ alkylsilyl $C_2$-$C_6$ alkynyl, $C_1$-$C_6$ alkylamido, a group $R^5R^6N$—, a group $R^5C(O)N(R^6)$—, a group $R^5S(O_2)N(R^6)$—, a group $R^5R^6NSO_2$—, a group $R^5R^6NC(O)$ $C_1$-$C_6$ alkyl, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryl $C_1$-$C_3$ alkyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heterocyclyl group optionally substituted by from 1 to 3 groups independently selected from $C_1C_4$ alkyl, a $C_3$-$C_6$ cycloalkyl group optionally substituted with from 1 to 3 groups independently selected from halogen, cyano, $C_1$-$C_6$ alkoxy and $C_1$-$C_6$ alkyl and a $C_3$-$C_6$ cycloalkenyl group optionally substituted with from 1 to 3 groups independently selected from halogen, cyano, $C_1$-$C_6$ alkoxy and $C_1$-$C_6$ alkyl;
$R^c$ is selected from hydrogen, halogen, cyano, $C_1$-$C_6$ alkyl and $C_1$-$C_6$ haloalkyl;
or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

$R^1$ is halogen and $R^2$ is $C_1$-$C_3$ alkyl, $C_1$-$C_3$ alkoxy or —$NR^{10}R_{11}$ or $R^1$ is $C_1$-$C_3$ alkoxy and $R^2$ is halogen, $C_1$-$C_3$ alkyl or $C_1$-$C_3$ alkoxy, or $R^1$ is $C_1$-$C_3$ alkyl and $R^2$ is $C_1$-$C_3$ alkoxy;
$R^3$ is selected from halogen, hydroxyl, or any one of the following groups

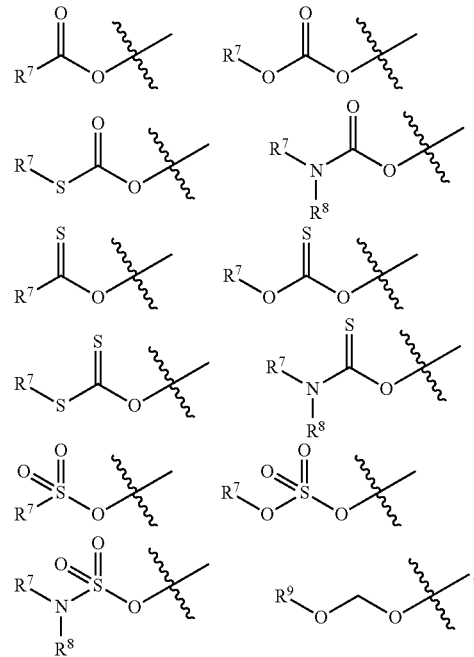

$R^5$ and $R^6$ are independently selected from hydrogen, $C_1$-$C_6$ alkyl, $C_1$-$C_6$ haloalkyl, $C_2$-$C_6$ alkenyl and $C_2$-$C_6$ alkynyl;
$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;
$R^9$ is selected from $C_1$-$C_6$ alkyl or benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;
$R^{10}$ is selected from H, $C_1$-$C_6$ alkyl, $C_1$-$C_6$ alkoxy-$C_1$-$C_6$ alkyl, $C_3$-$C_6$ cycloalkyl, $C_3$-$C_6$ cycloalkyl-$C_1$-$C_6$ alkyl, $C_2$-$C_6$ alkenyl and $C_2$-$C_6$ alkynyl; and
$R^{11}$ is selected from H and $C_1$-$C_6$ alkyl;
or an N-oxide or salt form thereof.
2. The compound of claim 1, wherein X is O.
3. The compound of claim 1, wherein $R^b$ is selected from $C_1$-$C_8$ alkyl, $C_1$-$C_6$ haloalkyl, $C_2$-$C_8$ alkenyl, $C_1$-$C_6$ cyanoalkyl, $C_1$-$C_6$ alkoxy, $C_1$-$C_6$ hydroxyalkyl, $C_2$-$C_6$ alkenyloxy $C_1$-$C_6$ alkyl, a group $R^5R^6NC(O)$ $C_1$-$C_6$ alkyl, $C_1$-$C_6$ alkoxy $C_1$-$C_6$ alkyl and $C_3$-$C_6$ cycloalkyl optionally substituted by from 1 to 3 groups independently selected from cyano, $C_1$-$C_3$ alkyl and $C_1$-$C_3$ alkoxy.

4. The compound of claim 3, wherein $R^b$ is selected from $C_1$-$C_8$ alkyl, $C_1$-$C_6$ haloalkyl, $C_2$-$C_8$ alkenyl, $C_1$-$C_6$ cyanoalkyl, $C_1$-$C_6$ alkoxy $C_1$-$C_6$ alkyl and $C_3$-$C_6$ cycloalkyl optionally substituted by from 1 to 3 groups independently selected from cyano and $C_1$-$C_3$ alkyl.

5. The compound of claim 4, wherein $R^b$ is selected from $C_1$-$C_6$ alkyl, $C_2$-$C_8$ alkenyl, $C_1$-$C_6$ cyanoalkyl, $C_1$-$C_6$ alkoxy $C_1$-$C_6$ alkyl and $C_3$-$C_6$ cycloalkyl optionally substituted by from 1 to 3 groups independently selected from cyano and $C_1$-$C_3$ alkyl.

6. The compound of claim 1, wherein $R^c$ is selected from hydrogen, halogen, cyano and $C_1$-$C_3$ alkyl.

7. The compound of claim 6, wherein $R^c$ is selected from hydrogen, fluorine, chlorine, bromine, methyl and cyano.

8. The compound of claim 7, wherein $R^c$ is selected from hydrogen, fluorine and cyano.

9. The compound of claim 1, wherein $R^1$ is chloro and $R^2$ is methyl, $R^1$ is bromo and $R^2$ is methyl, $R^1$ is chloro and $R^2$ is methoxy, $R^1$ is bromo and $R^2$ is methoxy, $R^1$ is chloro and $R^2$ is amino, $R^1$ is chloro and $R^2$ is N-allylamino, $R^1$ is chloro and $R^2$ is N-propargylamino, $R^1$ is bromo and $R^2$ is amino, $R^1$ is bromo and $R^2$ is N-allylamino, $R^1$ is bromo and $R^2$ is N-propargylamino, $R^1$ is methoxy and $R^2$ is methyl, $R^1$ is methoxy and $R^2$ is methoxy, $R^1$ is methyl and $R^2$ is methoxy, $R^1$ is methoxy and $R^2$ is chloro or $R^1$ is methoxy and $R^2$ is bromo.

10. The compound of claim 9, wherein $R^1$ is chloro and $R^2$ is methyl, $R^1$ is bromo and $R^2$ is methyl or $R^1$ is methoxy and $R^2$ is methyl.

11. The compound of claim 10, wherein $R^1$ is methoxy and $R^2$ is methyl.

12. The compound of claim 1, wherein $R^3$ is selected from halogen, hydroxyl, or any one of the following groups

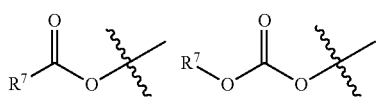

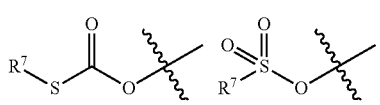

13. The compound of claim 12, wherein $R^3$ is selected from hydroxyl, halogen, $C_1$-$C_6$ alkylcarbonyloxy, $C_1$-$C_6$ alkoxycarbonyloxy or $C_6C_{10}$ aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

14. The compound of claim 13, wherein $R^3$ is selected from hydroxyl and halogen.

15. The compound of claim 14, wherein $R^3$ is hydroxyl.

16. A compound of formula (III)

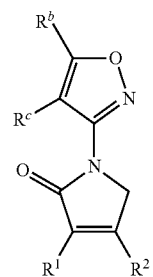

(III)

wherein $R^b$, $R^c$, $R^1$ and $R^2$ are as defined in claim 1.

17. A compound of formula (IV)

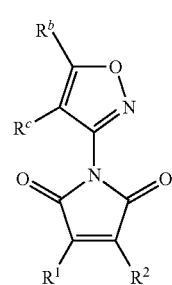

(IV)

wherein
$R^b$ is selected from hydrogen, formyl, hydroxyl, halogen, nitro, cyano, $C_1$-$C_8$ alkyl, $C_1$-$C_6$ cyanoalkyl, $C_1$-$C_6$ haloalkyl, $C_1$-$C_6$ hydroxyalkyl, $C_2$-$C_6$ alkenyloxy $C_1$-$C_6$ alkyl, $C_1$-$C_6$ alkylthio, $C_1$-$C_6$ alkoxy, $C_1$-$C_6$ alkoxy $C_1$-$C_6$ alkyl, $C_1$-$C_6$ alkylthio $C_1$-$C_6$ alkyl, $C_1$-$C_6$ cyanoalkoxy, $C_1$-$C_6$ haloalkoxy, $C_1$-$C_6$ alkoxy $C_1$-$C_6$ alkoxy, $C_2$-$C_8$ alkenyl, $C_2$-$C_8$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, $C_2$-$C_6$ alkenylcarbonyl, $C_2$-$C_6$ alkynylcarbonyl, $C_2$-$C_6$ haloalkenylcarbonyl, $C_2$-C6 haloalkynylcarbonyl, tri $C_1$-$C_6$ alkylsilyl $C_2$-$C_6$ alkynyl, $C_1$-$C_6$ alkylamido, a group $R^5R^6N$—, a group $R^5C(O)N(R^6)$—, a group $R^5S(O_2)N(R^6)$—, a group $R^5R^6NSO_2$—, a group $R^5R^6NC(O)$ $C_1$-$C_6$ alkyl, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$aryl $C_1$-$C_3$ alkyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heterocyclyl group optionally substituted by from 1 to 3 groups independently selected from $C_1$-$C_4$ alkyl, a $C_3$-$C_6$ cycloalkyl group optionally substituted with from 1 to 3 groups independently selected from halogen, cyano, $C_1$-$C_6$ alkoxy and $C_1$-$C_6$ alkyl and a $C_3$-$C_6$ cycloalkenyl group optionally substituted with from 1 to 3 groups independently selected from halogen, cyano, $C_1$-$C_6$ alkoxy and $C_1$-$C_6$ alkyl;

$R^c$ is selected from hydrogen, halogen, cyano, $C_1$-$C_6$ alkyl and $C_1$-$C_6$ haloalkyl;

or $R^b$ and $R^c$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

$R^1$ is halogen and $R^2$ is $C_1$-$C_3$ alkyl, $C_1$-$C_3$ alkoxy or —$NR^{10}R^{11}$ or $R^1$ is $C_1$-$C_3$ alkoxy and $R^2$ is halogen, $C_1$-$C_3$ alkyl or $C_1$-$C_3$ alkoxy, or $R^1$ is $C_1$-$C_3$ alkyl and $R^2$ is $C_1$-$C_3$ alkoxy;

$R^5$ and $R^6$ are independently selected from hydrogen, $C_1$-$C_6$ alkyl, $C_1$-$C_6$ haloalkyl, $C_2$-$C_6$ alkenyl and $C_2$-$C_6$ alkynyl; and $R^{11}$ is selected from H and $C_1$-$C_6$ alkyl.

18. A herbicidal composition comprising a compound of formula I as defined in claim 1 together with at least one agriculturally acceptable adjuvant or diluent.

19. A composition according to claim 18 which comprises a further herbicide in addition to the compound of formula I.

20. A method of controlling weeds in crops of useful plants, comprising applying to said weeds or to the locus of said weeds, or to said useful plants or to the locus of said useful plants, a compound of formula I as defined in claim 1.

\* \* \* \* \*